United States Patent
Schmiedel et al.

(10) Patent No.: US 10,724,008 B2
(45) Date of Patent: *Jul. 28, 2020

(54) KETOREDUCTASES

(71) Applicant: C-LEcta GmbH, Leipzig (DE)

(72) Inventors: Ramona Schmiedel, Leipzig (DE); Andreas Vogel, Leipzig (DE); Sabrina Koepke, Leipzig (DE); Rico Czaja, Leipzig (DE); Claudia Feller, Leipzig (DE); Hedda Merkens, Hamburg (DE); Kamila Rzeznicka, Leipzig (DE); Daniel Schwarze, Jena (DE); Thomas Greiner-Stoeffele, Soemmerda (DE); Andreas Petri, Leipzig (DE); Marc Struhalla, Leipzig (DE)

(73) Assignee: C-LEcta GmbH, Leipzig (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,296

(22) Filed: Aug. 30, 2018

(65) Prior Publication Data

US 2019/0062714 A1    Feb. 28, 2019

Related U.S. Application Data

(63) Continuation of application No. 15/305,870, filed as application No. PCT/EP2015/058411 on Apr. 17, 2015, now Pat. No. 10,093,905.

(30) Foreign Application Priority Data

Apr. 22, 2014  (EP) .................................... 14165444

(51) Int. Cl.
| | | |
|---|---|---|
| *C12P 7/26* | (2006.01) | |
| *C12P 7/02* | (2006.01) | |
| *C12P 7/40* | (2006.01) | |
| *C12N 9/04* | (2006.01) | |
| *C12P 7/24* | (2006.01) | |

(52) U.S. Cl.
CPC .............. *C12N 9/0006* (2013.01); *C12P 7/02* (2013.01); *C12P 7/24* (2013.01); *C12P 7/26* (2013.01); *C12P 7/40* (2013.01); *C12Y 101/01001* (2013.01); *C12Y 101/01184* (2013.01)

(58) Field of Classification Search
CPC ...... C12P 7/02; C12P 7/22; C12P 7/42; C12N 9/004; C12N 9/10; C12Y 101/01001
USPC .................. 435/148, 189, 69.1, 320.1, 252.2
See application file for complete search history.

(56) References Cited

U.S. PATENT DOCUMENTS

| 6,645,746 B1 | 11/2003 | Kizaki et al. |
|---|---|---|
| 7,393,667 B2 | 7/2008 | Patel et al. |
| 7,629,157 B2 | 12/2009 | Davis et al. |
| 7,977,078 B2 | 7/2011 | Liang et al. |
| 8,257,952 B2 | 9/2012 | Campopiano et al. |
| 8,273,554 B2 | 9/2012 | Mundorff et al. |
| 8,288,131 B2 | 10/2012 | Voladri et al. |
| 8,426,178 B2 | 4/2013 | Savile et al. |
| 8,512,973 B2 | 8/2013 | Liang et al. |
| 8,617,853 B2 | 12/2013 | Liang et al. |
| 2006/0035357 A1 | 2/2006 | Kizaki et al. |
| 2008/0220518 A1 | 9/2008 | Greiner-Stoffele et al. |
| 2016/0194647 A1 | 7/2016 | Greiner-Stoeffele et al. |

FOREIGN PATENT DOCUMENTS

| CN | 101889081 B | 6/2014 |
|---|---|---|
| EP | 1553170 | 5/2006 |
| WO | 2005040376 A2 | 5/2005 |
| WO | 2009029554 A2 | 3/2009 |
| WO | 2009042984 A1 | 4/2009 |
| WO | 2010075956 A1 | 7/2010 |
| WO | 2011022548 A2 | 2/2011 |
| WO | 2012007965 A1 | 1/2012 |
| WO | 2012046254 A2 | 4/2012 |
| WO | 2013061052 A1 | 5/2013 |

OTHER PUBLICATIONS

Altschul et al., Gapped BLAST and PSI-BLAST: a new generation of protein database search programs, FEBS J, Oct. 2005, 272(20): 5101-5109.
Altschul et al., Protein Database Searches Using Compositionally Adjusted Substitution Matrices, Nucleic Acid Research, Jul. 1997, vol. 25, No. 17, 3389-3402.
Devos et al., Practical Limits of Function Prediction, Proteins: Structure, Function and Genetics, 2000, vol. 41: 98-107.
Kisselev L., Polypeptide Release Factors in Prokaryotes and Eukaryotes: Same Function, Different Structure, Structure, 2002, vol. 10: 8-9.
Lountos et al., Crystallization and preliminary analysis of a water-forming NADH oxidase from Lactobacillus sanfranciscensis, Acta Cryst., Aug. 2004, D60, 2044-2047.
NCBI, XP002731083, "Short chain dehyrdogenase [Glaciibacter superstes]," Oct. 22, 2013.
Punta et al., The Pfam protein families database, Nucleic Acid Research, Nov. 2013, vol. 40, D290-D301.
Studier, Protein production by auto-induction in high-density shaking cultures, Protein Expression and Purification 41, Mar. 2005, 207-234.
Whisstock et al., Prediction of protein function from protein sequence and structure, Quarterly Reviews of Biophysics 2003, vol. 36 (3): 307-340.

(Continued)

*Primary Examiner* — Robert B Mondesi
*Assistant Examiner* — Mohammad Y Meah
(74) *Attorney, Agent, or Firm* — Agris & Von Natzmer, LLP; Joyce Von Natzmer

(57) ABSTRACT

The invention relates to ketoreductases and the use thereof. The ketoreductases of the invention are particularly useful for enzymatically catalyzing the reduction of ketones to chiral secondary alcohols.

22 Claims, No Drawings
Specification includes a Sequence Listing.

(56) References Cited

OTHER PUBLICATIONS

Witkowski et al., Conversion of beta-Ketoacyl Synthase to a Malonyl Decarboxylase by Replacement of the Active-Site Cysteine with Glutamine, Biochemistry 38:11643-11650, 1999.

Search report issued in corresponding Chinese application 201580021991.4 dated Jul. 29, 2019.

White et al., "First draft genome sequence from a member of the genus *Agrococcus*, isolated from modern microbialities," U1LT01_9MICO, sequence derived from EMBL/GenBank/DDBJ whole genome shotgun (WGS) entry; Genome Announc. 1:eD0391-13 (Nov. 13, 2013).

Search report issued by the Indian Patent Office in corresponding patent application 201617034442 on Jan. 30, 2020.

```
                          SEQUENCE LISTING

<160> NUMBER OF SEQ ID NOS: 93

<210> SEQ ID NO 1
<211> LENGTH: 765
<212> TYPE: DNA
<213> ORGANISM: unknown
<220> FEATURE:
<223> OTHER INFORMATION: isolated from library

<400> SEQUENCE: 1
atggctacac aattcgacgg taagaccgct ctcatcaccg agggggcttc cggcatcggc      60
tatgccgtcg ccctcgagct cgccgcggag ggtgccagcg tcgtcgtgca ggacctgcgc     120
ctcgaagcag cacagcaggt ggcagatgag atcaccgccg ccggcggcac ggcgatcgcc     180
gtagccggcg acgtcggcaa gccggaagac gtcaaagccg ccgtcgacgc cgccgtggcc     240
gcctatggcg ccctgcacct tgccgtcaac aacgccggca tcggcggccc caccgggctc     300
atcggcgact acgacgactc cgatggcttc gccgcctacc gcaagctcat cgatgtgaac     360
cttaactccg tctactacgg cctgcgctat gagatccctg ccatcatcag cgcgggcggc     420
ggttccattg tgaacacctc gtccatcctc gggctggtat ccgagccgac cgccgccccg     480
tacacgacgg ccaagcacgg tgttgccggt ctgaccaagg ccgctgccgc gggctacgcg     540
tcccagggtg tccgcatcaa ctccgtccac cccggataca tcgacacccc cctgctcgcc     600
gcgatgccca agaggccta cgacgccctc gtgtccaagc cccgatcgg ccgcctgggt     660 accgcggaag aagtcgccca cctcgtgact ttcctcctca gtgataaggc cagcttcatc     720
accggctcgc aacacgtcgt tgacggcgga tacgtcgcgg tctag                    765

<210> SEQ ID NO 2
<211> LENGTH: 254
<212> TYPE: PRT
<213> ORGANISM: unknown
<220> FEATURE:
<223> OTHER INFORMATION: isolated from library

<400> SEQUENCE: 2

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
```

```
                100                 105                 110
Tyr Arg Lys Leu Ile Asp Val Asn Leu Asn Ser Val Tyr Tyr Gly Leu
                115                 120                 125

Arg Tyr Glu Ile Pro Ala Ile Ile Ser Ala Gly Gly Ser Ile Val
        130                 135                 140

Asn Thr Ser Ser Ile Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
        180                 185                 190

Tyr Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
                210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 3
<211> LENGTH: 765
<212> TYPE: DNA
<213> ORGANISM: artificial
<220> FEATURE:
<223> OTHER INFORMATION: codon optimized artificial synthetic sequence

<400> SEQUENCE: 3

```
atggcaaccc agtttgatgg taaaaccgca ctgattaccg gtggtgcaag cggtattggt      60
tatgcagttg cactggaact ggcagcagaa ggtgccagcg ttgttgttca ggatctgcgt     120
ctggaagcag cacagcaggt tgcagatgaa attaccgcag ccggtggcac cgcaattgca     180
gttgccggtg atgttggtaa accggaagat gttaaagcag cagttgatgc agccgttgca     240
gcatatggtg cactgcatct ggcagttaat aatgcaggta ttggtggtcc gaccggtctg     300
attggtgatt atgatgatag tgatggtttt gcagcctatc gcaaactgat tgatgttaat     360
ctgaacagcg tgtattatgg cctgcgttat gaaattccgg caattattag tgccggtggt     420
ggtagcattg ttaataccag cagcattctg gtctggttag cgaaccgac cgcagcaccg     480
tataccaccg caaaacatgg tgttgcaggt ctgaccaaag cagccgcagc gggttatgca     540
agccagggtg ttcgtattaa tagcgttcat ccgggttata ttgatacacc gctgctggca     600
gcaatgccga agaagcata cgacgcactg gttagcaaac atccgattgg tcgtctgggc     660
accgcagaag aagttgcaca tctggttacc tttctgctga gcgataaagc aagctttatt     720
accggtagcc agcatgttgt tgatggtggt tatgttgcag tttaa                    765
```

<210> SEQ ID NO 4
<211> LENGTH: 254
<212> TYPE: PRT
<213> ORGANISM: artificial
<220> FEATURE:
<223> OTHER INFORMATION: isolated from library

<400> SEQUENCE: 4

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
```

```
            20                  25                  30
Ser Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Phe Asn Asn Ala Gly Ile Gly Gly
                85                  90                  95

Pro Thr Gly Leu Ile Gly Asp Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Ile Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
                180                 185                 190

Tyr Ile Asp Thr Pro Leu Leu Ala Ala Met Pro Lys Glu Ala Tyr Asp
            195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 5
<211> LENGTH: 254
<212> TYPE: PRT
<213> ORGANISM: artificial
<220> FEATURE:
<223> OTHER INFORMATION: isolated from library

<400> SEQUENCE: 5

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
                100                 105                 110

Tyr Arg Lys Leu Ile Asp Val Asn Leu Asn Ser Val Phe Tyr Gly Leu
            115                 120                 125

Arg Tyr Glu Ile Pro Ala Ile Ile Ser Ala Gly Gly Gly Ser Ile Val
```

```
            130                 135                 140
Asn Thr Ser Ser Ile Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Tyr Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
            210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 6
<211> LENGTH: 254
<212> TYPE: PRT
<213> ORGANISM: artificial
<220> FEATURE:
<223> OTHER INFORMATION: isolated from library

<400> SEQUENCE: 6

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Tyr Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
            210                 215                 220

Val Ala His Leu Ile Thr Phe Leu Leu Ser Asp Lys Ala Ser Phe Ile
225                 230                 235                 240

Thr Gly Ser Gln His Val Val Asp Gly Gly Tyr Val Ala Val
```

-continued 245                   250

<210> SEQ ID NO 7
<211> LENGTH: 254
<212> TYPE: PRT
<213> ORGANISM: artificial
<220> FEATURE:
<223> OTHER INFORMATION: isolated from library

<400> SEQUENCE: 7

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gln Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Phe Gly Leu Val Ser Ser Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Tyr Ile Asp Thr Pro Leu Thr Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 8
<211> LENGTH: 254
<212> TYPE: PRT
<213> ORGANISM: artificial
<220> FEATURE:
<223> OTHER INFORMATION: isolated from library

<400> SEQUENCE: 8

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Ser Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Ala Gly Leu Val Ser Ser Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Val Ile Asp Thr Pro Leu Ala Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 9
<211> LENGTH: 254
<212> TYPE: PRT
<213> ORGANISM: artificial
<220> FEATURE:
<223> OTHER INFORMATION: isolated from library

<400> SEQUENCE: 9

Met Ala Thr Gln Phe Asp Gly Lys Thr Ala Leu Ile Thr Gly Gly Ala
 1               5                  10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Glu Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile His Gly Leu Val Ser Glu Pro Thr Leu Ala Pro
145                 150                 155                 160

```
Tyr Thr Thr Ala Lys His Gly Val Ala Gly Leu Thr Lys Ala Ala Ala
            165                 170                 175

Ala Gly Tyr Ala Ser Gln Gly Val Arg Ile Asn Ser Val His Pro Gly
        180                 185                 190

Tyr Ile Asp Thr Pro Leu Leu Ala Ala Met Pro Lys Glu Ala Tyr Asp
    195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250
```

<210> SEQ ID NO 10
<211> LENGTH: 254
<212> TYPE: PRT
<213> ORGANISM: artificial
<220> FEATURE:
<223> OTHER INFORMATION: isolated from library

<400> SEQUENCE: 10

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gln Gly
                85                  90                  95

Ala Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Tyr Ile Asp Thr Pro Leu Thr Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 11
<211> LENGTH: 254

```
<212> TYPE: PRT
<213> ORGANISM: artificial
<220> FEATURE:
<223> OTHER INFORMATION: isolated from library

<400> SEQUENCE: 11

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Val Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Phe Gly Leu Val Ser Ser Pro Thr Val Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Pro Ile Asp Thr Pro Leu Thr Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 12
<211> LENGTH: 254
<212> TYPE: PRT
<213> ORGANISM: artificial
<220> FEATURE:
<223> OTHER INFORMATION: isolated from library

<400> SEQUENCE: 12

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80
```

```
Ala Tyr Gly Ala Leu His Leu Ala Val Asn Asn Ala Gly Ile Ser Gly
                85                  90                  95

Tyr Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Tyr Ile Asp Thr Pro Leu Ile Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 13
<211> LENGTH: 254
<212> TYPE: PRT
<213> ORGANISM: artificial
<220> FEATURE:
<223> OTHER INFORMATION: isolated from library

<400> SEQUENCE: 13

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gln Gly
                85                  90                  95

Lys Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Phe Gly Leu Val Ser Ser Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190
```

```
Ala Ile Asp Thr Pro Leu Thr Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 14
<211> LENGTH: 254
<212> TYPE: PRT
<213> ORGANISM: artificial
<220> FEATURE:
<223> OTHER INFORMATION: isolated from library

<400> SEQUENCE: 14

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Lys Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Phe Gly Leu Val Ser Leu Pro Thr Ser Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Ala Ile Asp Thr Pro Leu Ala Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 15
<211> LENGTH: 254
<212> TYPE: PRT
<213> ORGANISM: artificial
<220> FEATURE:
<223> OTHER INFORMATION: isolated from library -continued

<400> SEQUENCE: 15

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Tyr Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Ala Gly Leu Val Ser Ala Pro Thr Gly Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Ala Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 16
<211> LENGTH: 254
<212> TYPE: PRT
<213> ORGANISM: artificial
<220> FEATURE:
<223> OTHER INFORMATION: isolated from library

<400> SEQUENCE: 16

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Cys Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Ala Thr Gly Leu Ile Gly Asp Tyr Asp Asp Ser Asp Gly Phe Ala Ala
```

```
                    100                 105                 110
Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
        130                 135                 140

Asn Thr Ser Ser Ile Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Tyr Ile Asp Thr Pro Leu Ile Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Tyr Val Ala Val
                245                 250

<210> SEQ ID NO 17
<211> LENGTH: 254
<212> TYPE: PRT
<213> ORGANISM: artificial
<220> FEATURE:
<223> OTHER INFORMATION: isolated from library

<400> SEQUENCE: 17

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Asn Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Ala Gly Leu Val Ser Glu Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Ala Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
```

```
                210                 215                 220
Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 18
<211> LENGTH: 254
<212> TYPE: PRT
<213> ORGANISM: artificial
<220> FEATURE:
<223> OTHER INFORMATION: isolated from library

<400> SEQUENCE: 18

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Ser Gly
                85                  90                  95

Pro Thr Gly Leu Ile Gly Asp Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Ile Phe Gly Leu Val Ser Phe Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
                180                 185                 190

Phe Ile Asp Thr Pro Leu Thr Ala Ala Met Pro Lys Glu Ala Tyr Asp
            195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 19
<211> LENGTH: 254
<212> TYPE: PRT
<213> ORGANISM: artificial
<220> FEATURE:
<223> OTHER INFORMATION: isolated from library

<400> SEQUENCE: 19

```
Met Ala Thr Gln Phe Asp Gly Lys Thr Ala Leu Ile Thr Gly Gly Ala
1               5                   10                  15
```

-continued

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Val Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Ala Gly Leu Val Ser Leu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Phe Ile Asp Thr Pro Leu Ala Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 20
<211> LENGTH: 254
<212> TYPE: PRT
<213> ORGANISM: artificial
<220> FEATURE:
<223> OTHER INFORMATION: isolated from library

<400> SEQUENCE: 20

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gln Gly
                85                  90                  95

Ala Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
130                 135                 140

Asn Thr Ser Ser Ile Phe Gly Leu Val Ser Pro Thr Val Ala Pro
145                 150                 155                 160

Tyr Thr Thr Ala Lys His Gly Val Ala Gly Leu Thr Lys Ala Ala
                165                 170                 175

Ala Gly Tyr Ala Ser Gln Gly Val Arg Ile Asn Ser Val His Pro Gly
                180                 185                 190

Val Ile Asp Thr Pro Leu Ile Ala Ala Met Pro Lys Glu Ala Tyr Asp
                195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 21
<211> LENGTH: 254
<212> TYPE: PRT
<213> ORGANISM: artificial
<220> FEATURE:
<223> OTHER INFORMATION: isolated from library

<400> SEQUENCE: 21

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Ser Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Tyr Thr Gly Leu Ile Gly Asp Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
        130                 135                 140

Asn Thr Ser Ser Ile Leu Gly Leu Val Ser Phe Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
                180                 185                 190

Ala Ile Asp Thr Pro Leu Leu Ala Ala Met Pro Lys Glu Ala Tyr Asp
                195                 200                 205

Ala Leu Val Ser Lys His Pro Ile Gly Arg Leu Gly Thr Ala Glu Glu
            210                 215                 220

Val Ala His Leu Val Thr Phe Leu Leu Ser Asp Lys Ala Ser Phe Ile
225                 230                 235                 240

-continued

Thr Gly Ser Gln His Val Val Asp Gly Gly Tyr Val Ala Val
            245                 250

<210> SEQ ID NO 22
<211> LENGTH: 254
<212> TYPE: PRT
<213> ORGANISM: artificial
<220> FEATURE:
<223> OTHER INFORMATION: isolated from library

<400> SEQUENCE: 22

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Leu Gly Leu Val Ser Lys Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Thr Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 23
<211> LENGTH: 254
<212> TYPE: PRT
<213> ORGANISM: artificial
<220> FEATURE:
<223> OTHER INFORMATION: isolated from library

<400> SEQUENCE: 23

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

```
Asp Glu Ile Thr Ala Ala Gly Gly Thr Ala Ile Ala Val Ala Gly Asp
 50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Met Gly
                 85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Leu Gly Leu Val Ser Ser Pro Thr Val Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Phe Ile Asp Thr Pro Leu Thr Ala Ala Met Pro Lys Glu Ala Tyr Asp
        195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250
```

<210> SEQ ID NO 24
<211> LENGTH: 254
<212> TYPE: PRT
<213> ORGANISM: artificial
<220> FEATURE:
<223> OTHER INFORMATION: isolated from library

<400> SEQUENCE: 24

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
 50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Ala Gly
                 85                  90                  95

Asn Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Ala Gly Leu Val Ser Leu Pro Thr Leu Ala Pro
145                 150                 155                 160
```

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Pro Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250

<210> SEQ ID NO 25
<211> LENGTH: 254
<212> TYPE: PRT
<213> ORGANISM: artificial
<220> FEATURE:
<223> OTHER INFORMATION: isolated from library

<400> SEQUENCE: 25

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Asp Ala Ala Val Ala
65                  70                  75                  80

Ala Tyr Gly Ala Leu His Leu Ala Val Asn Asn Ala Gly Ile Gln Gly
                85                  90                  95

Val Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Ser Gly Leu Val Ser Gly Pro Thr Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Val Ile Asp Thr Pro Leu Thr Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250

<210> SEQ ID NO 26

<211> LENGTH: 254
<212> TYPE: PRT
<213> ORGANISM: artificial
<220> FEATURE:
<223> OTHER INFORMATION: isolated from library

<400> SEQUENCE: 26

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Met Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Ala Gly Leu Val Ser Phe Pro Thr Ser Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Ala Ile Asp Thr Pro Leu Thr Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 27
<211> LENGTH: 254
<212> TYPE: PRT
<213> ORGANISM: artificial
<220> FEATURE:
<223> OTHER INFORMATION: isolated from library

<400> SEQUENCE: 27

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala

```
            65                  70                  75                  80
Ala Tyr Gly Ala Leu His Leu Ala Val Asn Asn Ala Gly Ile Ser Gly
                85                  90                  95

Glu Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
        130                 135                 140

Asn Thr Ser Ser Ile Ala Gly Leu Val Ser Leu Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Val Ile Asp Thr Pro Leu Thr Ala Ala Met Pro Lys Glu Ala Tyr Asp
            195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 28
<211> LENGTH: 254
<212> TYPE: PRT
<213> ORGANISM: artificial
<220> FEATURE:
<223> OTHER INFORMATION: isolated from library

<400> SEQUENCE: 28

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Ser Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
        130                 135                 140

Asn Thr Ser Ser Ile Leu Gly Leu Val Ser Glu Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
```

```
            180                 185                 190
Val Ile Asp Thr Pro Leu Ala Ala Met Pro Lys Glu Ala Tyr Asp
        195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 29
<211> LENGTH: 254
<212> TYPE: PRT
<213> ORGANISM: artificial
<220> FEATURE:
<223> OTHER INFORMATION: isolated from library

<400> SEQUENCE: 29

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Phe Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Pro Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 30
<211> LENGTH: 254
<212> TYPE: PRT
<213> ORGANISM: artificial
<220> FEATURE:
<223> OTHER INFORMATION: isolated from library
```

<400> SEQUENCE: 30

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Ser Gly
                85                  90                  95

Ala Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Ile Ala Gly Leu Val Ser Leu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Phe Ile Asp Thr Pro Leu Ala Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 31
<211> LENGTH: 254
<212> TYPE: PRT
<213> ORGANISM: artificial
<220> FEATURE:
<223> OTHER INFORMATION: isolated from library

<400> SEQUENCE: 31

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Ser Gly
                85                  90                  95

```
Pro Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Ile Leu Gly Leu Val Ser Glu Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Thr Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 32
<211> LENGTH: 254
<212> TYPE: PRT
<213> ORGANISM: artificial
<220> FEATURE:
<223> OTHER INFORMATION: isolated from library

<400> SEQUENCE: 32

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
            85                  90                  95

Pro Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Ile Phe Gly Leu Val Ser Lys Pro Thr Ser Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Pro Ile Asp Thr Pro Leu Phe Ala Ala Met Pro Lys Glu Ala Tyr Asp
        195                 200                 205
```

```
Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 33
<211> LENGTH: 254
<212> TYPE: PRT
<213> ORGANISM: artificial
<220> FEATURE:
<223> OTHER INFORMATION: isolated from library

<400> SEQUENCE: 33

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Glu Gly
                85                  90                  95

Pro Thr Gly Leu Ile Gly Asp Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Ile Ala Gly Leu Val Ser Ser Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
                180                 185                 190

Val Ile Asp Thr Pro Leu Thr Ala Ala Met Pro Lys Glu Ala Tyr Asp
            195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 34
<211> LENGTH: 254
<212> TYPE: PRT
<213> ORGANISM: artificial
<220> FEATURE:
<223> OTHER INFORMATION: isolated from library

<400> SEQUENCE: 34

```
Met Ala Thr Gln Phe Asp Gly Lys Thr Ala Leu Ile Thr Gly Gly Ala
1               5                   10                  15
```

Ser Gly Ile Gly Tyr Ala Val Ala Leu Glu Leu Ala Ala Glu Gly Ala
            20                  25                  30

Ser Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
 50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Met Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
130                 135                 140

Asn Thr Ser Ser Ile Ala Gly Leu Val Ser Glu Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Val Ile Asp Thr Pro Leu Leu Ala Ala Met Pro Lys Glu Ala Tyr Asp
            195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 35
<211> LENGTH: 254
<212> TYPE: PRT
<213> ORGANISM: artificial
<220> FEATURE:
<223> OTHER INFORMATION: isolated from library

<400> SEQUENCE: 35

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
 50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Ala Gly
                85                  90                  95

Ala Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

```
Arg Tyr Glu Ile Pro Ala Ile Ile Ser Ala Gly Gly Ser Ile Val
        130                 135                 140

Asn Thr Ser Ser Ile Phe Gly Leu Val Ser Ala Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Pro Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

```
<210> SEQ ID NO 36
<211> LENGTH: 254
<212> TYPE: PRT
<213> ORGANISM: artificial
<220> FEATURE:
<223> OTHER INFORMATION: isolated from library

<400> SEQUENCE: 36
```

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Ala Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Ala Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240
```

Thr Gly Ser Gln His Val Val Asp Gly Gly Tyr Val Ala Val
            245                 250

<210> SEQ ID NO 37
<211> LENGTH: 254
<212> TYPE: PRT
<213> ORGANISM: artificial
<220> FEATURE:
<223> OTHER INFORMATION: isolated from library

<400> SEQUENCE: 37

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Ala Gly
                85                  90                  95

Val Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Leu Gly Leu Val Ser Glu Pro Thr Ser Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Ala Ile Asp Thr Pro Leu Ile Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250

<210> SEQ ID NO 38
<211> LENGTH: 254
<212> TYPE: PRT
<213> ORGANISM: artificial
<220> FEATURE:
<223> OTHER INFORMATION: isolated from library

<400> SEQUENCE: 38

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala

```
            35                  40                  45
Asp Glu Ile Thr Ala Ala Gly Gly Thr Ala Ile Ala Val Ala Gly Asp
         50                  55                  60
Val Gly Lys Pro Glu Asp Val Lys Ala Ala Val Asp Ala Ala Val Ala
 65                  70                  75                  80
Ala Tyr Gly Ala Leu His Leu Ala Val Asn Asn Ala Gly Ile Val Gly
                 85                  90                  95
Pro Thr Gly Leu Ile Gly Asp Tyr Asp Ser Asp Gly Phe Ala Ala
            100                 105                 110
Tyr Arg Lys Leu Ile Asp Val Asn Leu Asn Ser Val Tyr Tyr Gly Leu
            115                 120                 125
Arg Tyr Glu Ile Pro Ala Ile Ile Ser Ala Gly Gly Ser Ile Val
            130                 135                 140
Asn Thr Ser Ser Ile Leu Gly Leu Val Ser Glu Pro Thr Gln Ala Pro
145                 150                 155                 160
Tyr Thr Thr Ala Lys His Gly Val Ala Gly Leu Thr Lys Ala Ala Ala
                165                 170                 175
Ala Gly Tyr Ala Ser Gln Gly Val Arg Ile Asn Ser Val His Pro Gly
            180                 185                 190
Ala Ile Asp Thr Pro Leu Leu Ala Ala Met Pro Lys Glu Ala Tyr Asp
            195                 200                 205
Ala Leu Val Ser Lys His Pro Ile Gly Arg Leu Gly Thr Ala Glu Glu
            210                 215                 220
Val Ala His Leu Val Thr Phe Leu Leu Ser Asp Lys Ala Ser Phe Ile
225                 230                 235                 240
Thr Gly Ser Gln His Val Val Asp Gly Gly Tyr Val Ala Val
                245                 250

<210> SEQ ID NO 39
<211> LENGTH: 254
<212> TYPE: PRT
<213> ORGANISM: artificial
<220> FEATURE:
<223> OTHER INFORMATION: isolated from library

<400> SEQUENCE: 39

Met Ala Thr Gln Phe Asp Gly Lys Thr Ala Leu Ile Thr Gly Gly Ala
 1               5                  10                  15
Ser Gly Ile Gly Tyr Ala Val Ala Leu Glu Leu Ala Ala Glu Gly Ala
                20                  25                  30
Ser Val Val Val Gln Asp Leu Arg Leu Glu Ala Ala Gln Gln Val Ala
            35                  40                  45
Asp Glu Ile Thr Ala Ala Gly Gly Thr Ala Ile Ala Val Ala Gly Asp
         50                  55                  60
Val Gly Lys Pro Glu Asp Val Lys Ala Ala Val Asp Ala Ala Val Ala
 65                  70                  75                  80
Ala Tyr Gly Ala Leu His Leu Ala Val Asn Asn Ala Gly Ile Gly Gly
                85                  90                  95
Pro Thr Gly Leu Ile Gly Asp Tyr Asp Asp Ser Asp Gly Phe Ala Ala
            100                 105                 110
Tyr Arg Lys Leu Ile Asp Val Asn Leu Asn Ser Val Tyr Tyr Gly Leu
            115                 120                 125
Arg Tyr Glu Ile Pro Ala Ile Ile Ser Ala Gly Gly Gly Ser Ile Val
            130                 135                 140
Asn Thr Ser Ser Ile Phe Gly Leu Val Ser Ser Pro Thr Gln Ala Pro
```

```
            145                 150                 155                 160

Tyr Thr Thr Ala Lys His Gly Val Ala Gly Leu Thr Lys Ala Ala Ala
                        165                 170                 175

Ala Gly Tyr Ala Ser Gln Gly Val Arg Ile Asn Ser Val His Pro Gly
                        180                 185                 190

Gly Ile Asp Thr Pro Leu Leu Ala Ala Met Pro Lys Glu Ala Tyr Asp
                        195                 200                 205

Ala Leu Val Ser Lys His Pro Ile Gly Arg Leu Gly Thr Ala Glu Glu
                        210                 215                 220

Val Ala His Leu Val Thr Phe Leu Leu Ser Asp Lys Ala Ser Phe Ile
        225                 230                 235                 240

Thr Gly Ser Gln His Val Val Asp Gly Gly Tyr Val Ala Val
                        245                 250

<210> SEQ ID NO 40
<211> LENGTH: 254
<212> TYPE: PRT
<213> ORGANISM: artificial
<220> FEATURE:
<223> OTHER INFORMATION: isolated from library

<400> SEQUENCE: 40

Met Ala Thr Gln Phe Asp Gly Lys Thr Ala Leu Ile Thr Gly Gly Ala
        1               5                   10                  15

Ser Gly Ile Gly Tyr Ala Val Ala Leu Glu Leu Ala Ala Glu Gly Ala
                        20                  25                  30

Ser Val Val Val Gln Asp Leu Arg Leu Glu Ala Ala Gln Gln Val Ala
                        35                  40                  45

Asp Glu Ile Thr Ala Ala Gly Gly Thr Ala Ile Ala Val Ala Gly Asp
                        50                  55                  60

Val Gly Lys Pro Glu Asp Val Lys Ala Ala Val Asp Ala Ala Val Ala
        65                  70                  75                  80

Ala Tyr Gly Ala Leu His Leu Ala Val Asn Asn Ala Gly Ile Gly Gly
                        85                  90                  95

Pro Thr Gly Leu Ile Gly Asp Tyr Asp Asp Ser Asp Gly Phe Ala Ala
                        100                 105                 110

Tyr Arg Lys Leu Ile Asp Val Asn Leu Asn Ser Val Tyr Tyr Gly Leu
                        115                 120                 125

Arg Tyr Glu Ile Pro Ala Ile Ile Ser Ala Gly Gly Gly Ser Ile Val
                        130                 135                 140

Asn Thr Ser Ser Ile Leu Gly Leu Val Ser Asp Pro Thr Gln Ala Pro
        145                 150                 155                 160

Tyr Thr Thr Ala Lys His Gly Val Ala Gly Leu Thr Lys Ala Ala Ala
                        165                 170                 175

Ala Gly Tyr Ala Ser Gln Gly Val Arg Ile Asn Ser Val His Pro Gly
                        180                 185                 190

Gly Ile Asp Thr Pro Leu Leu Ala Ala Met Pro Lys Glu Ala Tyr Asp
                        195                 200                 205

Ala Leu Val Ser Lys His Pro Ile Gly Arg Leu Gly Thr Ala Glu Glu
                        210                 215                 220

Val Ala His Leu Val Thr Phe Leu Leu Ser Asp Lys Ala Ser Phe Ile
        225                 230                 235                 240

Thr Gly Ser Gln His Val Val Asp Gly Gly Tyr Val Ala Val
                        245                 250
```

-continued

```
<210> SEQ ID NO 41
<211> LENGTH: 254
<212> TYPE: PRT
<213> ORGANISM: artificial
<220> FEATURE:
<223> OTHER INFORMATION: isolated from library

<400> SEQUENCE: 41

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Leu Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 42
<211> LENGTH: 254
<212> TYPE: PRT
<213> ORGANISM: artificial
<220> FEATURE:
<223> OTHER INFORMATION: isolated from library

<400> SEQUENCE: 42

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60
```

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Met Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 43
<211> LENGTH: 254
<212> TYPE: PRT
<213> ORGANISM: artificial
<220> FEATURE:
<223> OTHER INFORMATION: isolated from library

<400> SEQUENCE: 43

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Gly Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

```
Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 44
<211> LENGTH: 254
<212> TYPE: PRT
<213> ORGANISM: artificial
<220> FEATURE:
<223> OTHER INFORMATION: isolated from library

<400> SEQUENCE: 44

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Thr Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 45
<211> LENGTH: 254
<212> TYPE: PRT
<213> ORGANISM: artificial
<220> FEATURE:

<223> OTHER INFORMATION: isolated from library

<400> SEQUENCE: 45

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Gln Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 46
<211> LENGTH: 254
<212> TYPE: PRT
<213> ORGANISM: artificial
<220> FEATURE:
<223> OTHER INFORMATION: isolated from library

<400> SEQUENCE: 46

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
130                 135                 140

Asn Thr Ser Ser Ala Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
            195                 200                 205

Ala Leu Val Ser Lys His Pro Ile Gly Arg Leu Gly Thr Ala Glu Glu
            210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250

<210> SEQ ID NO 47
<211> LENGTH: 254
<212> TYPE: PRT
<213> ORGANISM: artificial
<220> FEATURE:
<223> OTHER INFORMATION: isolated from library

<400> SEQUENCE: 47

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
130                 135                 140

Asn Thr Ser Ser Val Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
            195                 200                 205

```
Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 48
<211> LENGTH: 254
<212> TYPE: PRT
<213> ORGANISM: artificial
<220> FEATURE:
<223> OTHER INFORMATION: isolated from library

<400> SEQUENCE: 48

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Glu Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Ile Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 49
<211> LENGTH: 254
<212> TYPE: PRT
<213> ORGANISM: artificial
<220> FEATURE:
<223> OTHER INFORMATION: isolated from library

<400> SEQUENCE: 49

Met Ala Thr Gln Phe Asp Gly Lys Thr Ala Leu Ile Thr Gly Gly Ala
```

```
            1               5                  10                 15
        Ser Gly Ile Gly Tyr Ala Val Ala Leu Glu Leu Ala Ala Glu Gly Ala
                        20                 25                 30

Ser Val Val Gln Asp Leu Arg Leu Glu Ala Ala Gln Gln Val Ala
                    35                 40                 45

Asp Glu Ile Thr Ala Ala Gly Gly Thr Ala Ile Ala Val Ala Gly Asp
                    50                 55                 60

Val Gly Lys Pro Glu Asp Val Lys Ala Ala Val Asp Ala Ala Val Ala
        65                  70                 75                 80

Ala Tyr Gly Ala Leu His Leu Ala Val Asn Asn Ala Gly Ile Gly Gly
                        85                 90                 95

Pro Thr Gly Leu Ile Gly Asp Tyr Asp Asp Ser Asp Gly Phe Ala Ala
                        100                105                110

Tyr Arg Lys Leu Ile Asp Val Asn Leu Asn Ser Val Tyr Tyr Gly Leu
                        115                120                125

Arg Tyr Glu Ile Pro Ala Ile Ile Ser Ala Gly Gly Ser Ile Val
                    130                135                140

Asn Thr Ser Ser Ile Phe Gly Leu Val Ser Ser Pro Thr Gln Ala Pro
        145                 150                155                160

Tyr Thr Thr Ala Lys His Gly Val Ala Gly Leu Thr Lys Ala Ala Ala
                        165                170                175

Ala Gly Tyr Ala Ser Gln Gly Val Arg Ile Asn Ser Val His Pro Gly
                    180                185                190

Gly Ile Asp Thr Pro Met Leu Ala Ala Met Pro Lys Glu Ala Tyr Asp
                    195                200                205

Ala Leu Val Ser Lys His Pro Ile Gly Arg Leu Gly Thr Ala Glu Glu
                    210                215                220

Val Ala His Leu Val Thr Phe Leu Leu Ser Asp Lys Ala Ser Phe Ile
        225                 230                235                240

Thr Gly Ser Gln His Val Val Asp Gly Gly Tyr Val Ala Val
                        245                250

<210> SEQ ID NO 50
<211> LENGTH: 254
<212> TYPE: PRT
<213> ORGANISM: artificial
<220> FEATURE:
<223> OTHER INFORMATION: isolated from library

<400> SEQUENCE: 50

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
```

```
            115                 120                 125
Arg Tyr Glu Ile Pro Ala Ile Ile Ser Ala Gly Gly Gly Ser Ile Val
        130                 135                 140
Asn Thr Ser Ser Ile Phe Gly Leu Val Ser Ser Pro Thr Gln Ala Pro
145                 150                 155                 160
Tyr Thr Thr Ala Lys His Gly Val Ala Gly Leu Thr Lys Ala Ala Ala
                165                 170                 175
Ala Gly Tyr Ala Ser Gln Gly Val Arg Ile Asn Ser Val His Pro Gly
            180                 185                 190
Gly Ile Asp Thr Pro Leu Leu Ala Gly Met Pro Lys Glu Ala Tyr Asp
        195                 200                 205
Ala Leu Val Ser Lys His Pro Ile Gly Arg Leu Gly Thr Ala Glu Glu
    210                 215                 220
Val Ala His Leu Val Thr Phe Leu Leu Ser Asp Lys Ala Ser Phe Ile
225                 230                 235                 240
Thr Gly Ser Gln His Val Val Asp Gly Gly Tyr Val Ala Val
                245                 250

<210> SEQ ID NO 51
<211> LENGTH: 254
<212> TYPE: PRT
<213> ORGANISM: artificial
<220> FEATURE:
<223> OTHER INFORMATION: isolated from library

<400> SEQUENCE: 51

Met Ala Thr Gln Phe Asp Gly Lys Thr Ala Leu Ile Thr Gly Gly Ala
1               5                   10                  15
Ser Gly Ile Gly Tyr Ala Val Ala Leu Glu Leu Ala Ala Glu Gly Ala
            20                  25                  30
Ser Val Val Val Gln Asp Leu Arg Leu Glu Ala Ala Gln Gln Val Ala
        35                  40                  45
Asp Glu Ile Thr Ala Ala Gly Gly Thr Ala Ile Ala Val Ala Gly Asp
    50                  55                  60
Val Gly Lys Pro Glu Asp Val Lys Ala Ala Val Asp Ala Ala Val Ala
65                  70                  75                  80
Ala Tyr Gly Ala Leu His Leu Ala Val Asn Asn Ala Gly Ile Gly Gly
                85                  90                  95
Pro Thr Gly Leu Ile Gly Asp Tyr Asp Asp Ser Asp Gly Phe Ala Ala
            100                 105                 110
Tyr Arg Lys Leu Ile Asp Val Asn Leu Asn Ser Val Tyr Tyr Gly Leu
        115                 120                 125
Arg Tyr Glu Ile Pro Ala Ile Ile Ser Ala Gly Gly Gly Ser Ile Val
    130                 135                 140
Asn Thr Ser Ser Ile Phe Gly Leu Val Ser Ser Pro Thr Gln Ala Pro
145                 150                 155                 160
Tyr Thr Thr Ala Lys His Gly Val Ala Gly Leu Thr Lys Ala Ala Ala
                165                 170                 175
Ala Gly Tyr Ala Ser Gln Gly Val Arg Ile Asn Ser Val His Pro Gly
            180                 185                 190
Gly Ile Asp Thr Pro Leu Leu Ala Met Pro Lys Glu Ala Arg Asp
        195                 200                 205
Ala Leu Val Ser Lys His Pro Ile Gly Arg Leu Gly Thr Ala Glu Glu
    210                 215                 220
Val Ala His Leu Val Thr Phe Leu Leu Ser Asp Lys Ala Ser Phe Ile
```

-continued

```
                225                 230                 235                 240
Thr Gly Ser Gln His Val Val Asp Gly Gly Tyr Val Ala Val
                    245                 250

<210> SEQ ID NO 52
<211> LENGTH: 254
<212> TYPE: PRT
<213> ORGANISM: artificial
<220> FEATURE:
<223> OTHER INFORMATION: isolated from library

<400> SEQUENCE: 52

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
        130                 135                 140

Asn Thr Ser Ser Ile Phe Gly Leu Val Ser Ser Pro Tyr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                    245                 250

<210> SEQ ID NO 53
<211> LENGTH: 254
<212> TYPE: PRT
<213> ORGANISM: artificial
<220> FEATURE:
<223> OTHER INFORMATION: isolated from library

<400> SEQUENCE: 53

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30
```

```
Ser Val Val Val Gln Asp Val Arg Leu Glu Ala Ala Gln Gln Val Ala
         35                  40                  45

Asp Glu Ile Thr Ala Ala Gly Gly Thr Ala Ile Ala Val Ala Gly Asp
 50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Gly Gly
                 85                  90                  95

Pro Thr Gly Leu Ile Gly Asp Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Ile Phe Gly Leu Val Ser Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 54
<211> LENGTH: 254
<212> TYPE: PRT
<213> ORGANISM: artificial
<220> FEATURE:
<223> OTHER INFORMATION: isolated from library

<400> SEQUENCE: 54

Met Ala Thr Gln Phe Asp Gly Lys Thr Ala Leu Ile Thr Gly Gly Ala
 1               5                  10                  15

Ser Gly Ile Gly Tyr Ala Val Ala Leu Glu Leu Ala Ala Glu Gly Ala
                 20                  25                  30

Ser Val Val Val Gln Asp Leu Arg Leu Glu Ala Ala Gln Gln Val Ala
         35                  40                  45

Asp Glu Ile Thr Ala Ala Gly Gly Thr Ala Ile Ala Val Ala Gly Asp
 50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Gly Gly
                 85                  90                  95

Pro Thr Gly Leu Ile Gly Asp Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140
```

Asn Thr Ser Ser Ile Phe Gly Leu Val Gly Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 55
<211> LENGTH: 254
<212> TYPE: PRT
<213> ORGANISM: artificial
<220> FEATURE:
<223> OTHER INFORMATION: isolated from library

<400> SEQUENCE: 55

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Val Arg Leu Glu Gly Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Val Phe Gly Leu Val Gly Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Gly Met Pro Lys Glu Ala Leu Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

```
<210> SEQ ID NO 56
<211> LENGTH: 254
<212> TYPE: PRT
<213> ORGANISM: artificial
<220> FEATURE:
<223> OTHER INFORMATION: isolated from library

<400> SEQUENCE: 56

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Val Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Phe Gly Leu Val Gly Ser Pro Tyr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Gly Met Pro Lys Glu Ala Arg Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Tyr Val Ala Val
                245                 250

<210> SEQ ID NO 57
<211> LENGTH: 254
<212> TYPE: PRT
<213> ORGANISM: artificial
<220> FEATURE:
<223> OTHER INFORMATION: isolated from library

<400> SEQUENCE: 57

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Val Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60
```

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Phe Gly Leu Val Gly Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Gly Met Pro Lys Glu Ala Leu Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 58
<211> LENGTH: 254
<212> TYPE: PRT
<213> ORGANISM: artificial
<220> FEATURE:
<223> OTHER INFORMATION: isolated from library

<400> SEQUENCE: 58

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Val Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Phe Gly Leu Val Gly Ser Pro Thr Gln Ala Pro
145                 150                 155                 160

Tyr Thr Thr Ala Lys His Gly Val Ala Gly Leu Thr Lys Ala Ala Ala
                165                 170                 175

```
Ala Gly Tyr Ala Ser Gln Gly Val Arg Ile Asn Ser Val His Pro Gly
            180                 185                 190

Gly Ile Asp Thr Pro Met Leu Ala Gly Met Pro Lys Glu Ala Arg Asp
            195                 200                 205

Ala Leu Val Ser Lys His Pro Ile Gly Arg Leu Gly Thr Ala Glu Glu
            210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 59
<211> LENGTH: 254
<212> TYPE: PRT
<213> ORGANISM: artificial
<220> FEATURE:
<223> OTHER INFORMATION: isolated from library

<400> SEQUENCE: 59

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Val Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Val Phe Gly Leu Val Gly Ser Pro Thr Trp Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Gly Met Pro Lys Glu Ala Arg Asp
            195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 60
<211> LENGTH: 254
<212> TYPE: PRT
<213> ORGANISM: artificial

<220> FEATURE:
<223> OTHER INFORMATION: isolated from library

<400> SEQUENCE: 60

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ile Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 61
<211> LENGTH: 254
<212> TYPE: PRT
<213> ORGANISM: artificial
<220> FEATURE:
<223> OTHER INFORMATION: isolated from library

<400> SEQUENCE: 61

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly

```
                  85                  90                  95
Pro Thr Gly Leu Ile Gly Asp Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
        130                 135                 140

Asn Thr Ser Ser Val Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Lys Ala Ser Phe Ile
225                 230                 235                 240

Thr Gly Ser Gln His Val Val Asp Gly Gly Tyr Val Ala Val
                245                 250
```

<210> SEQ ID NO 62
<211> LENGTH: 254
<212> TYPE: PRT
<213> ORGANISM: artificial
<220> FEATURE:
<223> OTHER INFORMATION: isolated from library

<400> SEQUENCE: 62

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Gly Gly Leu Ile Gly Asp Tyr Asp Asp Ser Asp Gly Phe Ala Ala
                100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
        130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Ala Met Pro Lys Glu Ala Tyr Asp
```

```
                195                 200                 205
Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 63
<211> LENGTH: 254
<212> TYPE: PRT
<213> ORGANISM: artificial
<220> FEATURE:
<223> OTHER INFORMATION: isolated from library

<400> SEQUENCE: 63

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
                20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Ala Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Tyr Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 64
<211> LENGTH: 254
<212> TYPE: PRT
<213> ORGANISM: artificial
<220> FEATURE:
<223> OTHER INFORMATION: isolated from library

<400> SEQUENCE: 64

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
    130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
            195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250

<210> SEQ ID NO 65
<211> LENGTH: 254
<212> TYPE: PRT
<213> ORGANISM: artificial
<220> FEATURE:
<223> OTHER INFORMATION: isolated from library

<400> SEQUENCE: 65

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Gly Leu
            115                 120                 125

Arg Tyr Glu Ile Pro Ala Ile Ile Ser Ala Gly Gly Ser Ile Val
        130                 135                 140

Asn Thr Ser Ser Val Leu Gly Leu Val Ser Glu Pro Thr Ala Pro
145                 150                 155                 160

Tyr Thr Ala Ala Lys His Gly Val Ala Gly Leu Thr Lys Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 66
<211> LENGTH: 254
<212> TYPE: PRT
<213> ORGANISM: artificial
<220> FEATURE:
<223> OTHER INFORMATION: isolated from library

<400> SEQUENCE: 66

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Gly Leu
            115                 120                 125

Arg Tyr Glu Ile Pro Ala Ile Ile Ser Ala Gly Gly Ser Ile Val
        130                 135                 140

Asn Thr Ser Ser Val Leu Gly Leu Val Ser Glu Pro Thr Ala Pro
145                 150                 155                 160

Tyr Thr Ser Ala Lys His Gly Val Ala Gly Leu Thr Lys Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 67
<211> LENGTH: 254
<212> TYPE: PRT
<213> ORGANISM: artificial
<220> FEATURE:
<223> OTHER INFORMATION: isolated from library

<400> SEQUENCE: 67

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Val Leu Gly Leu Val Ser Glu Pro Thr Gln Ala Pro
145                 150                 155                 160

Tyr Thr Ala Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 68
<211> LENGTH: 254
<212> TYPE: PRT
<213> ORGANISM: artificial
<220> FEATURE:
<223> OTHER INFORMATION: isolated from library

<400> SEQUENCE: 68

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

```
Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Val Leu Gly Leu Val Ser Glu Pro Thr Gln Ala Pro
145                 150                 155                 160

Tyr Thr Ser Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
            195                 200                 205

Ala Leu Val Ser Lys His Pro Ile Gly Arg Leu Gly Thr Ala Glu Glu
        210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 69
<211> LENGTH: 254
<212> TYPE: PRT
<213> ORGANISM: artificial
<220> FEATURE:
<223> OTHER INFORMATION: isolated from library

<400> SEQUENCE: 69

Met Ala Thr Gln Phe Asp Gly Lys Thr Ala Leu Ile Thr Gly Gly Ala
 1               5                  10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
            35                  40                  45

Asp Glu Ile Thr Ala Ala Gly Gly Thr Ala Ile Ala Val Ala Gly Asp
        50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
        130                 135                 140
```

Asn Thr Ser Ser Val Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val Cys Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 70
<211> LENGTH: 254
<212> TYPE: PRT
<213> ORGANISM: artificial
<220> FEATURE:
<223> OTHER INFORMATION: isolated from library

<400> SEQUENCE: 70

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Gly Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Val Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 71
<211> LENGTH: 254
<212> TYPE: PRT
<213> ORGANISM: artificial
<220> FEATURE:
<223> OTHER INFORMATION: isolated from library

<400> SEQUENCE: 71

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Gly Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Val Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 72
<211> LENGTH: 254
<212> TYPE: PRT
<213> ORGANISM: artificial
<220> FEATURE:
<223> OTHER INFORMATION: isolated from library

<400> SEQUENCE: 72

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp

```
            50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Gly Gly
                     85                  90                  95

Pro Thr Gly Leu Ile Gly Asp Tyr Asp Ser Asp Gly Phe Ala Ala
                    100                 105                 110

Tyr Arg Lys Leu Ile Asp Val Asn Leu Asn Ser Val Tyr Tyr Gly Leu
                    115                 120                 125

Arg Tyr Glu Ile Pro Ala Ile Ile Ser Ala Gly Gly Ser Ile Val
                130                 135                 140

Asn Thr Ser Ser Val Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                    165                 170                 175

Ala Gly Tyr Ala Ser Gln Gly Val Arg Ile Asn Ser Val His Pro Gly
                180                 185                 190

Gly Ile Asp Thr Pro Met Leu Ala Ala Met Pro Lys Glu Ala Tyr Asp
                195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                    245                 250
```

<210> SEQ ID NO 73
<211> LENGTH: 254
<212> TYPE: PRT
<213> ORGANISM: artificial
<220> FEATURE:
<223> OTHER INFORMATION: isolated from library

<400> SEQUENCE: 73

```
Met Ala Thr Gln Phe Asp Gly Lys Thr Ala Leu Ile Thr Gly Gly Ala
  1               5                  10                  15

Ser Gly Ile Gly Tyr Ala Val Ala Leu Glu Leu Ala Ala Glu Gly Ala
                 20                  25                  30

Ser Val Val Val Gln Asp Leu Arg Leu Glu Ala Ala Gln Gln Val Ala
                 35                  40                  45

Asp Glu Ile Thr Ala Ala Gly Gly Thr Ala Ile Ala Val Ala Gly Asp
 50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Gly Gly
                     85                  90                  95

Pro Thr Gly Leu Ile Gly Asp Tyr Asp Ser Asp Gly Phe Ala Ala
                    100                 105                 110

Tyr Arg Lys Leu Ile Asp Val Asn Leu Asn Ser Val Tyr Tyr Gly Leu
                    115                 120                 125

Arg Tyr Glu Ile Pro Ala Ile Ile Ser Ala Gly Gly Ser Ile Val
                130                 135                 140

Asn Thr Ser Ser Val Ser Gly Leu Val Ser Leu Pro Thr Gln Ala Pro
145                 150                 155                 160

Tyr Thr Thr Ala Lys His Gly Val Ala Gly Leu Thr Lys Ala Ala Ala
```

```
                165                 170                 175
Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 74
<211> LENGTH: 254
<212> TYPE: PRT
<213> ORGANISM: artificial
<220> FEATURE:
<223> OTHER INFORMATION: isolated from library

<400> SEQUENCE: 74

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Ser Gly Leu Val Ser Asp Pro Thr Ser Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 75
<211> LENGTH: 254
<212> TYPE: PRT
```

<213> ORGANISM: artificial
<220> FEATURE:
<223> OTHER INFORMATION: isolated from library

<400> SEQUENCE: 75

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Leu Gly Leu Val Ser Leu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 76
<211> LENGTH: 254
<212> TYPE: PRT
<213> ORGANISM: artificial
<220> FEATURE:
<223> OTHER INFORMATION: isolated from library

<400> SEQUENCE: 76

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80
```

```
Ala Tyr Gly Ala Leu His Leu Ala Val Asn Asn Ala Gly Ile Gly Gly
                 85                  90                  95

Pro Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
            130                 135                 140

Asn Thr Ser Ser Val Leu Gly Leu Val Ser Glu Pro Thr Ser Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
            195                 200                 205

Ala Leu Val Ser Lys His Pro Ile Gly Arg Leu Gly Thr Ala Glu Glu
            210                 215                 220

Val Ala His Leu Val Thr Phe Leu Leu Ser Asp Lys Ala Ser Phe Ile
225                 230                 235                 240

Thr Gly Ser Gln His Val Val Asp Gly Tyr Val Ala Val
                245                 250
```

```
<210> SEQ ID NO 77
<211> LENGTH: 254
<212> TYPE: PRT
<213> ORGANISM: artificial
<220> FEATURE:
<223> OTHER INFORMATION: isolated from library

<400> SEQUENCE: 77

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
            130                 135                 140

Asn Thr Ser Ser Val Leu Gly Leu Val Ser Ala Pro Thr Ser Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190
```

```
Gly Ile Asp Thr Pro Leu Leu Ala Ala Met Pro Lys Glu Ala Tyr Asp
            195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250
```

```
<210> SEQ ID NO 78
<211> LENGTH: 254
<212> TYPE: PRT
<213> ORGANISM: artificial
<220> FEATURE:
<223> OTHER INFORMATION: isolated from library

<400> SEQUENCE: 78

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Leu Gly Leu Val Ser Asp Pro Thr Ser Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
            195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
            245                 250
```

```
<210> SEQ ID NO 79
<211> LENGTH: 254
<212> TYPE: PRT
<213> ORGANISM: artificial
<220> FEATURE:
<223> OTHER INFORMATION: isolated from library

<400> SEQUENCE: 79
```

```
Met Ala Thr Gln Phe Asp Gly Lys Thr Ala Leu Ile Thr Gly Gly Ala
1               5                  10                 15

Ser Gly Ile Gly Tyr Ala Thr Ala Leu Glu Leu Ala Ala Glu Gly Ala
            20                  25                  30

Ser Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
            85                  90                  95

Pro Gly Gly Leu Ile Gly Asp Tyr Asp Asp Ser Asp Gly Phe Ala Ala
                100                 105                 110

Tyr Arg Lys Leu Ile Asp Tyr Asn Leu Asn Ser Ile Tyr Tyr Gly Leu
            115                 120                 125

Arg Tyr Glu Ile Pro Ala Ile Ile Ser Ala Gly Gly Ser Ile Val
    130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Met Pro Lys Glu Ala Tyr Asp
        195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 80
<211> LENGTH: 254
<212> TYPE: PRT
<213> ORGANISM: artificial
<220> FEATURE:
<223> OTHER INFORMATION: isolated from library

<400> SEQUENCE: 80

Met Ala Thr Gln Phe Asp Gly Lys Thr Ala Leu Ile Thr Gly Gly Ala
1               5                  10                 15

Ser Gly Ile Gly Tyr Ala Val Ala Leu Glu Leu Ala Ala Glu Gly Ala
            20                  25                  30

Ser Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
            85                  90                  95

Pro Gly Gly Leu Ile Gly Asp Tyr Asp Asp Ser Asp Tyr Phe Ala Ala
                100                 105                 110
```

```
Tyr Arg Lys Leu Ile Asp Val Asn Gln Asn Ser Ile Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Ala Met Pro Lys Glu Gly Tyr Asp
        195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

```
<210> SEQ ID NO 81
<211> LENGTH: 254
<212> TYPE: PRT
<213> ORGANISM: artificial
<220> FEATURE:
<223> OTHER INFORMATION: isolated from library

<400> SEQUENCE: 81

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Gly Gly Leu Ile Gly Asp Tyr Asp Asp Ser Asp Tyr Phe Ala Ala
            100                 105                 110

Tyr Arg Lys Leu Ile Asp Val Asn Leu Asn Ser Ile Tyr Tyr Gly Leu
            115                 120                 125

Arg Tyr Glu Ile Pro Ala Ile Ile Ser Ala Gly Gly Gly Ser Ile Val
        130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Ala Met Pro Lys Glu Gly Tyr Asp
        195                 200                 205

Ala Leu Val Ser Lys His Pro Ile Gly Arg Leu Gly Thr Ala Glu Glu
210                 215                 220
```

Val Ala His Leu Val Thr Phe Leu Leu Ser Asp Lys Ala Ser Phe Ile
225                 230                 235                 240

Thr Gly Ser Gln His Val Ile Asp Gly Gly Tyr Val Ala Val
                245                 250

<210> SEQ ID NO 82
<211> LENGTH: 254
<212> TYPE: PRT
<213> ORGANISM: artificial
<220> FEATURE:
<223> OTHER INFORMATION: isolated from library

<400> SEQUENCE: 82

Met Ala Thr Gln Phe Asp Gly Lys Thr Ala Leu Ile Thr Gly Gly Ala
1               5                   10                  15

Ser Gly Ile Gly Tyr Ala Thr Ala Leu Glu Leu Ala Ala Glu Gly Ala
            20                  25                  30

Ala Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Gly Gly Leu Ile Gly Asp Tyr Asp Asp Ser Asp Tyr Phe Ala Ala
            100                 105                 110

Tyr Arg Lys Leu Ile Asp Val Asn Leu Asn Ser Ile Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Ala Met Pro Lys Glu Gly Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Ile Asp Gly Gly Tyr Val Ala Val
                245                 250

<210> SEQ ID NO 83
<211> LENGTH: 254
<212> TYPE: PRT
<213> ORGANISM: artificial
<220> FEATURE:
<223> OTHER INFORMATION: isolated from library

<400> SEQUENCE: 83

Met Ala Thr Gln Phe Asp Gly Lys Thr Ala Leu Ile Thr Gly Gly Ala
1               5                   10                  15

Ser Gly Ile Gly Tyr Ala Thr Ala Leu Glu Leu Ala Ala Glu Gly Ala

```
            20                  25                  30
Ala Val Val Gln Asp Leu Arg Leu Glu Ala Ala Gln Gln Val Ala
        35                  40                  45
Asp Glu Ile Thr Ala Ala Gly Gly Thr Ala Ile Ala Val Ala Gly Asp
    50                  55                  60
Val Gly Lys Pro Glu Asp Val Lys Ala Ala Val Asp Ala Ala Val Ala
65                  70                  75                  80
Ala Tyr Gly Ala Leu His Leu Ala Val Asn Asn Ala Gly Ile Gly Gly
                85                  90                  95
Pro Gly Gly Leu Ile Gly Asp Tyr Asp Asp Ser Asp Gly Phe Ala Ala
                100                 105                 110
Tyr Arg Lys Leu Ile Asp Val Asn Leu Asn Ser Ile Tyr Tyr Gly Leu
            115                 120                 125
Arg Tyr Glu Ile Pro Ala Ile Ile Ser Ala Gly Gly Ser Ile Val
        130                 135                 140
Asn Thr Ser Ser Val Leu Gly Leu Val Ser Glu Pro Thr Gln Ala Pro
145                 150                 155                 160
Tyr Thr Thr Ala Lys His Gly Val Ala Gly Leu Thr Lys Ala Ala Ala
                165                 170                 175
Ala Gly Tyr Ala Ser Gln Gly Val Arg Ile Asn Ser Val His Pro Gly
                180                 185                 190
Gly Ile Asp Thr Pro Met Leu Ala Ala Met Pro Lys Glu Gly Tyr Asp
            195                 200                 205
Ala Leu Val Ser Lys His Pro Ile Gly Arg Leu Gly Thr Ala Glu Glu
        210                 215                 220
Val Ala His Leu Val Thr Phe Leu Leu Ser Asp Lys Ala Ser Phe Ile
225                 230                 235                 240
Thr Gly Ser Gln His Val Ile Asp Gly Gly Tyr Val Ala Val
                245                 250

<210> SEQ ID NO 84
<211> LENGTH: 254
<212> TYPE: PRT
<213> ORGANISM: artificial
<220> FEATURE:
<223> OTHER INFORMATION: isolated from library

<400> SEQUENCE: 84

Met Ala Thr Gln Phe Asp Gly Lys Thr Ala Leu Ile Thr Gly Gly Ala
1               5                   10                  15
Ser Gly Ile Gly Tyr Ala Val Ala Leu Glu Leu Ala Ala Glu Gly Ala
                20                  25                  30
Ser Val Val Gln Asp Leu Arg Leu Glu Ala Ala Gln Gln Val Ala
        35                  40                  45
Asp Glu Ile Thr Ala Ala Gly Gly Thr Ala Ile Ala Val Ala Gly Asp
    50                  55                  60
Val Gly Lys Pro Glu Asp Val Lys Ala Ala Val Asp Ala Ala Val Ala
65                  70                  75                  80
Ala Tyr Gly Ala Leu His Leu Ala Val Asn Asn Ala Gly Ile Met Gly
                85                  90                  95
Pro Thr Gly Leu Ile Gly Asp Tyr Asp Asp Ser Asp Gly Phe Ala Ala
                100                 105                 110
Tyr Arg Lys Leu Ile Asp Val Asn Leu Asn Ser Val Tyr Tyr Gly Leu
            115                 120                 125
Arg Tyr Glu Ile Pro Ala Ile Ile Ser Ala Gly Gly Gly Ser Ile Val
```

```
            130                 135                 140

Asn Thr Ser Ser Ile Ala Gly Leu Val Ser Glu Pro Thr Leu Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Thr Ile Asp Thr Pro Leu Ile Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

<210> SEQ ID NO 85
<211> LENGTH: 254
<212> TYPE: PRT
<213> ORGANISM: artificial
<220> FEATURE:
<223> OTHER INFORMATION: isolated from library

<400> SEQUENCE: 85

```
Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Phe Gly Leu Val Gly Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Gly Met Pro Lys Glu Ala Arg Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
```

```
<210> SEQ ID NO 86
<211> LENGTH: 254
<212> TYPE: PRT
<213> ORGANISM: artificial
<220> FEATURE:
<223> OTHER INFORMATION: isolated from library

<400> SEQUENCE: 86
```

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Val Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Ser Ile Val
    130                 135                 140

Asn Thr Ser Ser Val Leu Gly Leu Val Gly Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Gly Met Pro Lys Glu Ala Arg Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

```
<210> SEQ ID NO 87
<211> LENGTH: 254
<212> TYPE: PRT
<213> ORGANISM: artificial
<220> FEATURE:
<223> OTHER INFORMATION: isolated from library

<400> SEQUENCE: 87
```

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Val Arg Leu Glu Ala Ala Gln Gln Val Ala
        35                  40                  45

Asp Glu Ile Thr Ala Ala Gly Gly Thr Ala Ile Ala Val Ala Gly Asp
            50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
            130                 135                 140

Asn Thr Ser Ser Val Phe Gly Leu Val Gly Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Gly Met Pro Lys Glu Ala Arg Asp
            195                 200                 205

Ala Leu Val Ser Lys His Pro Ile Gly Arg Leu Gly Thr Ala Glu Glu
            210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 88
<211> LENGTH: 254
<212> TYPE: PRT
<213> ORGANISM: artificial
<220> FEATURE:
<223> OTHER INFORMATION: isolated from library

<400> SEQUENCE: 88

Met Ala Thr Gln Phe Asp Gly Lys Thr Ala Leu Ile Thr Gly Gly Ala
 1                   5                  10                  15

Ser Gly Ile Gly Tyr Ala Val Ala Leu Glu Leu Ala Ala Glu Gly Ala
                20                  25                  30

Ser Val Val Val Gln Asp Val Arg Leu Glu Ala Ala Gln Gln Val Ala
            35                  40                  45

Asp Glu Ile Thr Ala Ala Gly Gly Thr Ala Ile Ala Val Ala Gly Asp
            50                  55                  60

Val Gly Lys Pro Glu Asp Val Lys Ala Ala Val Asp Ala Ala Val Ala
 65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Gly Ser Ile Val
            130                 135                 140

Asn Thr Ser Ser Val Phe Gly Leu Val Gly Ser Pro Thr Gln Ala Pro
145                 150                 155                 160

-continued

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Gly Met Pro Lys Glu Ala Arg Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 89
<211> LENGTH: 254
<212> TYPE: PRT
<213> ORGANISM: artificial
<220> FEATURE:
<223> OTHER INFORMATION: isolated from library

<400> SEQUENCE: 89

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Val Arg Leu Glu Ala Ala Gln Gln Val Ala
        35                  40                  45

Asp Glu Ile Thr Ala Ala Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Val Phe Gly Leu Val Gly Ser Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Ala Met Pro Lys Glu Ala Arg Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 90
<211> LENGTH: 254

```
<212> TYPE: PRT
<213> ORGANISM: artificial
<220> FEATURE:
<223> OTHER INFORMATION: isolated from library

<400> SEQUENCE: 90

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Ala Gly
                85                  90                  95

Pro Thr Gly Leu Ile Gly Asp Tyr Asp Asp Ser Asp Gly Phe Ala Ala
            100                 105                 110

Tyr Arg Lys Leu Ile Asp Val Asn Leu Asn Ser Val Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Thr Leu Gly Leu Val Ser Glu Pro Thr Ala Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Leu Leu Ala Ala Met Pro Lys Glu Ala Tyr Asp
        195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 91
<211> LENGTH: 254
<212> TYPE: PRT
<213> ORGANISM: artificial
<220> FEATURE:
<223> OTHER INFORMATION: isolated from library

<400> SEQUENCE: 91

Met Ala Thr Gln Phe Asp Gly Lys Thr Ala Leu Ile Thr Gly Gly Ala
1               5                   10                  15

Ser Gly Ile Gly Tyr Ala Val Ala Leu Glu Leu Ala Ala Glu Gly Ala
            20                  25                  30

Ser Val Val Val Gln Asp Leu Arg Leu Glu Glu Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80
```

```
Ala Tyr Gly Ala Leu His Leu Ala Val Asn Asn Ala Gly Ile Gly Gly
                 85                  90                  95

Pro Ala Gly Leu Ile Gly Asp Tyr Asp Ser Asp Gly Phe Ala Ala
            100                 105                 110

Tyr Arg Lys Leu Ile Asp Val Asn Leu Asn Ser Val Tyr Tyr Gly Leu
            115                 120                 125

Arg Tyr Glu Ile Pro Ala Ile Ile Ser Ala Gly Gly Ser Ile Val
130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Ala Met Pro Lys Glu Ala Tyr Asp
            195                 200                 205

Ala Leu Val Ser Lys His Pro Ile Gly Arg Leu Gly Thr Ala Glu Glu
210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 92
<211> LENGTH: 254
<212> TYPE: PRT
<213> ORGANISM: artificial
<220> FEATURE:
<223> OTHER INFORMATION: isolated from library

<400> SEQUENCE: 92

Met Ala Thr Gln Phe Asp Gly Lys Thr Ala Leu Ile Thr Gly Gly Ala
1               5                   10                  15

Ser Gly Ile Gly Tyr Ala Thr Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Gly Gly Leu Ile Gly Asp Tyr Asp Asp Ser Asp Tyr Phe Ala Ala
            100                 105                 110

Tyr Arg Lys Leu Ile Asp Val Asn Leu Asn Ser Ile Tyr Tyr Gly Leu
            115                 120                 125

Arg Tyr Glu Ile Pro Ala Ile Ile Ser Ala Gly Gly Ser Ile Val
130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190
```

```
Gly Ile Asp Thr Pro Met Leu Ala Ala Met Pro Lys Glu Ala Tyr Asp
            195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250

<210> SEQ ID NO 93
<211> LENGTH: 254
<212> TYPE: PRT
<213> ORGANISM: artificial
<220> FEATURE:
<223> OTHER INFORMATION: isolated from library

<400> SEQUENCE: 93

Met Ala Thr Gln Phe Asp Gly Lys Thr Ala Leu Ile Thr Gly Gly Ala
1               5                   10                  15

Ser Gly Ile Gly Gln Ala Val Ala Leu Glu Leu Ala Ala Glu Gly Ala
            20                  25                  30

Ser Val Val Val Gln Asp Leu Arg Leu Glu Ala Ala Gln Gln Val Ala
        35                  40                  45

Asp Glu Ile Thr Ala Ala Gly Gly Thr Ala Ile Ala Val Ala Gly Asp
    50                  55                  60

Val Gly Lys Pro Glu Asp Val Lys Ala Ala Val Asp Ala Ala Val Ala
65                  70                  75                  80

Ala Tyr Gly Ala Leu His Leu Ala Val Asn Asn Ala Gly Ile Gly Gly
                85                  90                  95

Pro Gly Gly Leu Ile Gly Asp Tyr Asp Asp Ser Asp Tyr Phe Ala Ala
            100                 105                 110

Tyr Arg Lys Leu Ile Asp Val Asn Leu Asn Ser Ile Tyr Tyr Gly Leu
        115                 120                 125

Arg Tyr Glu Ile Pro Ala Ile Ile Ser Ala Gly Gly Gly Ser Ile Val
    130                 135                 140

Asn Thr Ser Ser Val Leu Gly Leu Val Ser Glu Pro Thr Gln Ala Pro
145                 150                 155                 160

Tyr Thr Thr Ala Lys His Gly Val Ala Gly Leu Thr Lys Ala Ala Ala
                165                 170                 175

Ala Gly Tyr Ala Ser Gln Gly Val Arg Ile Asn Ser Val His Pro Gly
            180                 185                 190

Gly Ile Asp Thr Pro Met Leu Ala Ala Met Pro Lys Glu Gly Tyr Asp
            195                 200                 205

Ala Leu Val Ser Lys His Pro Ile Gly Arg Leu Gly Thr Ala Glu Glu
    210                 215                 220

Val Ala His Leu Val Thr Phe Leu Leu Ser Asp Lys Ala Ser Phe Ile
225                 230                 235                 240

Thr Gly Ser Gln His Val Val Asp Gly Gly Tyr Val Ala Val
                245                 250
```

KETOREDUCTASES

CROSS-REFERENCE TO RELATED APPLICATIONS

This is the continuation of U.S. patent application Ser. No. 15/305,870, Now U.S. patent Ser. No. 10/093,905, which is the U.S. national stage of International application PCT/EP2015/058411, filed Apr. 17, 2015 designating the United States and claiming priority to EP 14165444.2, filed Apr. 22, 2014

INCORPORATION OF SEQUENCE LISTING

The sequence listing which was filed as a text file as part of International application PCT/EP2015/058411, filed Apr. 17, 2015, is hereby incorporated by reference. An extra copy of this text file named "eolf-seql.txt", which is 208.8 kilobytes (measured in MS-WINDOWS), dated Apr. 29, 2015 was downloaded from WIPO and was submitted in U.S. patent application Ser. No. 15/305,870 on Oct. 20, 2016 via the USPTO EFS system.

Ketoreductases (KREDs, also called 'alcohol dehydrogenases' ADHs, or 'carbonyl reductases') catalyze the reduction of aldehydes and ketones to the corresponding primary and secondary alcohols, respectively. These enzymes are also capable of catalyzing the reverse reaction, i.e. the oxidation of primary and secondary alcohols to the corresponding aldehydes and ketones, respectively.

For industrial applications the reduction of ketones to secondary alcohols is of great interest, since prochiral carbonyl compounds are stereoselectively reduced to chiral alcohols. In some industrial applications, also the stereoselective conversion of secondary alcohols to ketones for chiral resolution of racemic compounds is desired, e.g. allowing the isolation of enantiomers. The enzymatic oxidation of primary alcohols to aldehydes and the enzymatic reduction of aldehydes to primary alcohols are often considered of lower relevance in industrial applications, but are also catalyzed by KREDs. The use of a same KRED for oxidation or reduction reaction, respectively, can be influenced through adjustment of the chemical equilibrium of the enzyme reaction.

The reduction catalyzed by KREDs requires a reduced cofactor as electron donor. Some KREDs use reduced nicotinamide adenine dinucleotide (NADH) as a cofactor, other KREDs use reduced nicotinamide adenine dinucleotide phosphate (NADPH) and some ketoreductases accept both, NADH and NADPH. The oxidation catalyzed by KREDs accordingly requires an oxidized cofactor as electron acceptor. For this reaction KREDs use oxidized nicotinamide adenine dinucleotide ($NAD^+$) or oxidized nicotinamide adenine dinucleotide phosphate ($NADP^+$) or both, $NAD^+$ and $NADP^+$.

KREDs are ubiquitous enzymes found in all kingdoms of life. Well-known, commercially available KREDs are derived from horse liver (HLADH), baker's yeast (YADH) and from bacteria, such as *Thermoanaerobium brockii* (TBADH) and *Lactobacillus kefir* (LKADH).

Based on their sequence identity and biochemical properties, KREDs can be classified into different protein families. Members of the SDR-family (Short-Chain-Dehydrogenase/Reductase) exhibit short-chain enzymes, which do not contain any metal ions. In contrast, members of the MDR-family (Medium-Chain-Dehydrogenase/Reductase) exhibit medium-chain enzymes, which are dependent on $Zn^{2+}$. Another group of KREDs exhibits long-chain enzymes dependent on $Fe^{2+}$ (for review: K. Drauz, H. Gröger, O. May, Enzyme Catalysis in Organic Synthesis, Wiley VCH, Weinheim, 2012).

For industrial applications it is desirable to employ KREDs with a high specific activity and stereoselectivity. Another important criterion in the industrial use of KREDs is a long process stability, which often correlates with a high stability at elevated temperatures and a high solvent stability. If the substrates are chiral already, it is further desirable to employ KREDs with a high stereospecificity.

The improvement of enzymes can be achieved by enzyme engineering. This technique involves the development of variants of a starting enzyme with improved properties (for review: S. Lutz, U. T. Bornscheuer, Protein Engineering Handbook, Wiley VCH, Weinheim, 2009).

The in vitro use of KREDs in reduction processes requires a regeneration system for NAD(P)H. Common regeneration systems are glucose dehydrogenase (GDH) or formate dehydrogenase, which are used in conjunction with KREDs. Cofactor regeneration can also be done by the KRED itself by concomitant oxidation of a cosubstrate (often primary or secondary alcohols, e.g. oxidation of isopropanol to acetone). The concomitant use of KREDs as reduction catalysts and cofactor regeneration systems requires concurrent acceptance of a keto substrate and the cosubstrate for cofactor regeneration. The selection of a specific cosubstrate may depend on the specific activity of the KRED for such cosubstrate and the KRED stability under the specific cofactor regeneration conditions.

Besides the reversible reduction of aldehydes, there are a few reports about ketoreductases catalyzing the oxidation of aldehydes to the corresponding acids. However, this reaction is considered to be rather a side reaction and not the main function (for review: K. Drauz, H. Gröger, O. May, Enzyme Catalysis in Organic Synthesis, Wiley VCH, Weinheim, 2012).

Examples for the industrial use of KREDs to generate valuable compounds are the reduction of 1-phenyl-2-propanone by *Rhodococcus erythroplis* KRED, the reduction of ethyl acetoacetate by *Lactobacillus brevis* KRED or the reduction of 6-benzyloxy-3,5-dioxo-hexanoic acid ethyl ester by an KRED derived from *Acinetobacter calcoaceticus* (for review: A. Liese, K. Seelbach, C. Wandrey, Industrial Biotransformations, WileyVCH, Weinheim, 2006).

Even though a large number of KREDs catalyzing asymmetric reductions is described in the literature, only a few KREDs are used in patented processes. Many processes contain ketoreductase from *Lactobacillus kefir* (LKADH) or rather variants thereof. U.S. Pat. No. 8,426,178 discloses a process for the stereoselective reduction of N,N-dimethyl-3-keto-3-(2-thienyl)-1-ketopropanamine to (S)—N,N-dimethyl-3-hydroxy-3-(2-thienyl)-1-propanamine by variants of LKADH. U.S. Pat. No. 8,512,973 describes a process for the stereoselective reduction of a 2',6'-substituted acetophenone to the corresponding substituted (S)-1-phenethanol by KRED variants of *Lactobacillus kefir*, *Lactobacillus brevis* or *Lactobacillus minor*. In U.S. Pat. No. 7,977,078 a method for stereoselectively reducing 3-ketothiolane to (R)-3-hydroxythiolane by LKADH variants is disclosed. U.S. Pat. No. 8,617,853 describes a process for stereoselectively reducing the substrate 2-[3-[3-[2-(7-chloro-2-quinoliny) ethenyl]phenyl]-3-oxopropyl]benzoic acid methyl ester to (S,E)-methyl 2-(3-(3-(2-(7-chloroquinolin-2-yl)viny)lphenyl)-3-hydroxypropyl)benzoate by variants of KREDs from *Lactobacillus brevis*, *Lactobacillus kefir* or *Lactobacillus minor*. U.S. Pat. No. 8,273,554 discloses a process for the stereoselective reduction of 5-((4S)-2-oxo-4-phenyl (1,3- oxazolidin-3-yl))-1-(4-fluorophenyl) pentane-1,5-dione to (4S)-3[(5S)-5-(4fluorophenyl)-5-hydroxypentanoyl]-4-phenyl-1,3-oxazolidin-2-one by LKADH variants. In U.S. Pat. No. 6,645,746 a method for asymmetrically reducing tert-butyl (S)-6-chloro-5-hydroxy-3-oxohexanoate to tert-butyl (3R,5S)-6-chloro-3,5-dihydroxyhexanoate by ketoreductase of *Candida magnolia* is described. U.S. Pat. No. 7,393,667 discloses the preparation of propan-2-ols such as 1-[4-(4-halo-2-methyl-1H-indol-5-yloxy)-5-methyl-pyrrolo[2,1-f][1,2,4]triazin-6-yloxy]-propan-2-ol by stereo-selective reduction of a corresponding oxo compound using ketoreductase of *Pichia angusta*. U.S. Pat. No. 8,288,131 relates to a method for the stereoselective reduction of 2-methylpentanal to (R)-2-methylpentanol by variants of LKADH. WO 2011/022548 discloses a method for the stereoselective conversion of 1-(3-hydroxyphenyl)-2-(methylamino)ethanone to (R)-phenylephrine by LKADH variants. In WO 2012/046254 a stereoselective enzymatic reduction process of 4-oxo-4-[3-(trifluoromethyl)-5,6-dihydro[1,2,4]triazolo[4,3-a]pyrazin-7(8H-yl)-1-(2,4,5-trifluoro-phenyl)butan-2-one for the preparation of (S) or (R)-3-hydroxy-1-(3-(trifluoromethyl)-5,6-dihydro-[1,2,4]triazolo[4,3-a]pyrazin-7(8H)-yl)-4-(2,4,5-trifluorophenyl)butan-1- one with KREDs from *Saccharomyces cerevisiae, Rhodotorula rubra, Pichia methanolica* or *E. coli* is disclosed. U.S. Pat. No. 8,257,952 discloses LKADH variants capable of stereoselectively reducing methyl-2-benzamidomethyl-3-oxobutyrate to 2R,3R-methyl-2-benzamidomethyl-3-hydroxy-butyrate. U.S. Pat. No. 7,629,157 describes variants of ketoreductases from *Candidae magnolia* capable of stereoselectively converting ethyl 4-chloroacetoacetate to ethyl (S)-4-chloro-3-hydroxybutyrate.

EP 1 553 170 relates to a polypeptide forming (R)—N-benzyl-3-pyrrolidinol, a polynucleotide coding for said polypeptide, and use of the same. The polypeptide is said to have the following physical and chemical properties (1) to (4): (1) activity: acting on N-benzyl-3-pyrrolidinone with NADH or NADPH as a coenzyme, to form (R)—N-benzyl-3-pyrrolidinol; (2) optimum pH for activity: 5.5 to 6.0; (3) optimum temperature for activity: 50° C. to 55° C.; (4) molecular weight: about 55,000 as determined by gel filtration analysis, about 28,000 as determined by SDS polyacrylamide gel electrophoresis analysis.

Database Protein online, accession no. WP_022887115, relates to a short-chain dehydrogenase of *Glaciibacter superstes*.

The ketoreductases of the prior art, however, are not satisfactory in every respect and there is a demand for ketoreductases having advantages compared to conventional ketoreductases, particularly with respect to high process stabilities for the industrial production of chiral alcohol compounds and good cofactor regeneration activities, respectively. In this regard, high process stabilities in industrial applications may encompass chemical and physical stability and enzymatic activity in aqueous, non-aqueous environments and/or at biphasic systems, and/or at high substrate concentrations and/or at elevated temperatures and/or with the addition of water miscible solvents and/or at a broad pH-range from 4-11 and/or on solid supports (i.e. when being immobilized) and/or under high shear forces (e.g. produced by stirring, pumping, membrane filtration). Other factors, such as substrate selectivity, $K_M$, specific activity, stereoselectivity, stereospecificity, diastereoselectivity, regioselectivity, substrate inhibition, product inhibition, inhibition by other factors e. g. crude extract components, substrate contaminants or side products, and recombinant soluble expressability in suitable hosts may play an important role. When the substrate is a chiral substrate, i.e. already contains one or more chiral centers and/or axes itself, it may be desirable that the stereoselectivity of the enzymatic reduction of a prochiral carbonyl group contained in said chiral substrate is not substantially influenced by said one or more chiral centers and/or axes.

It is an object of the invention to provide improved ketoreductases.

This problem has been solved by the subject-matter of the patent claims.

The invention provides new ketoreductases, particularly engineered ketoreductases exhibiting improved properties as compared to the wild type enzyme, preferably the wild type ketoreductase of SEQ ID NO:2.

A first aspect of the invention relates to a ketoreductase comprising an amino acid sequence with a homology of at least 72% to the amino acid sequence of SEQ ID NO:2.

The ketoreductase according to the invention comprises such an amino acid sequence with a defined homology to the amino acid sequence of SEQ ID NO:2. This means that the ketoreductase according to the invention may comprise said amino acid sequence as a subsequence of its overall amino acid sequence, or that the ketoreductase according to the invention may essentially consist of said amino acid sequence. When the ketoreductase according to the invention comprises said amino acid sequence as a subsequence of its overall amino acid sequence, said overall amino acid sequence may be extended, i.e. may comprise additional amino acid residues, at the N-terminus and/or at the C-terminus of said subsequence. Such extension may be advantageous, for example, when the ketoreductase is to be immobilized on a solid support, e.g. for purification purposes.

In the meaning of this invention, the homology is preferably calculated as identity using BLASTP (Stephen F. Altschul, Thomas L. Madden, Alejandro A. Schäffer, Jinghui Zhang, Zheng Zhang, Webb Miller, and David J. Lipman (1997) "Gapped BLAST and PSI-BLAST: a new generation of protein database search programs", Nucleic Acids Res. 25:3389-3402; Stephen F. Altschul, John C. Wootton, E. Michael Gertz, Richa Agarwala, Aleksandr Morgulis, Alejandro A. Schäffer, and Yi-Kuo Yu (2005) "Protein database searches using compositionally adjusted substitution matrices." FEBS J. 272:5101-5109), preferably using version BLASTP 2.2.29+ (http://blast.ncbi.nlm.nih.gov/Blast.cgi), preferably using the following settings:

Field "Enter Query Sequence": Query subrange: none

Field "Choose Search Set": Database: non-redundant protein sequences (nr); optional parameters: none Field "Program Selection": Algorithm: blastp (protein-protein BLAST)

Algorithm parameters: Field "General parameters": Max target sequences: 100; Short queries: Automatically adjust parameters for short input sequences; Expect threshold: 10; Word size: 3; Max matches in a query range: 0

Algorithm parameters: Field "Scoring parameters": Matrix: BLOSUM62; Gap Costs: Existence: 11 Extension: 1; Compositional adjustments: Conditional compositional score matrix adjustment Algorithm parameters: Field "Filters and Masking": Filter: none; Mask: none Preferably, the ketoreductase according to the invention is capable of stereoselectively reducing keto substrates to secondary alcohols and/or capable of stereoselectively oxidizing secondary alcohols to keto products.

Preferably, the ketoreductases according to the invention are capable of oxidizing primary alcohols to aldehydes and/or capable of reducing aldehydes to primary alcohols.

In some embodiments, the ketoreductases according to the invention are capable of oxidizing an aldehyde compound to a carboxylic acid.

Preferably, the ketoreductase comprises an amino acid sequence with a homology of at least 72%, preferably at least 75%, or at least 80%, or at least 82%, or at least 84%, more preferably at least 86%, or at least 88%, still more preferably at least 90%, or at least 91%, yet more preferably at least 92%, or at least 93%, even more preferably at least 94%, or at least 95%, most preferably at least 96%, or at least 97%, and in particular at least 98%, or at least 99% to the amino acid sequence of SEQ ID NO:2.

It has been surprisingly found that the ketoreductases according to the invention exhibit a high activity a broad substrate tolerance a high stereoselectivity, a high stereospecificity, and/or a high stability in various solvents optionally containing cosubstrates such as isopropanol.

For the purpose of the specification, stereoselectivity is the property of a chemical reaction in which a single reactant forms an unequal mixture of stereoisomers during the non-stereospecific creation of a new stereocenter or during the non-stereospecific transformation of a pre-existing one. The selectivity typically arises from differences in steric effects and electronic effects in the mechanistic pathways leading to the different products. Preferably, the conversion of a substrate into a chiral product under catalysis of the ketoreductase according to the invention provides the desired chiral product with an enantiomeric excess of at least 50% ee, more preferably at least 75% ee, still more preferably at least 90% ee, yet more preferably at least 95% ee, even more preferably at least 97% ee, most preferably at least 98% ee, and in particular at least 99% ee.

For the purpose of the specification, stereospecificity is the property of a reaction mechanism that leads to different stereoisomeric reaction products from different stereoisomeric reactants, or which operates on only one (or a subset) of the stereoisomers. Preferably, the conversion of a chiral substrate into another chiral product under catalysis of the ketoreductase according to the invention provides the desired chiral product with an diastereomeric excess of at least 50% de, more preferably at least 75% de, still more preferably at least 90% de, yet more preferably at least 95% de, even more preferably at least 97% de, most preferably at least 98% de, and in particular at least 99% de.

In a preferred embodiment, the ketoreductase according to the invention is capable of preferably stereoselectively reducing a keto substrate of general formula (I)

(I)

to a secondary alcohol; or the ketoreductase according to the invention is capable of preferably stereospecifically reducing an aldehyde substrate of general formula (I')

to a primary alcohol;

wherein X and Y are each independently selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged to the CO-moiety through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged to the CO-moiety through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;

wherein mono- or polysubstituted means independently substituted with one or more functional groups selected from -halo, —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —$S(=O)_{1-2}OH$, —NO, —$NO_2$, —$N_3$, —$NH_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —$CO_2H$, CO—$C_{1-2}$- alkyl, —CO—$C_{6-10}$-aryl and —CO-heteroaryl.

Preferably, X and Y are each independently selected from unsubstituted or mono- or polysubstituted $C_{1-12}$-alkyl; unsubstituted or mono- or polysubstituted $C_{6-10}$-aryl, optionally being bridged to the CO-moiety through a unsubstituted or mono- or polysubstituted $C_{1-12}$-alkylene residue; unsubstituted or mono- or polysubstituted heteroaryl, optionally being bridged to the CO-moiety through a unsubstituted or mono- or polysubstituted aliphatic $C_{1-12}$-alkylene residue; and sugar residues or desoxysugar residues in each case comprising mono-, di- or oligosaccharides;

wherein mono- or polysubstituted means independently substituted with one or more functional groups selected from -halo, —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —$S(=O)_{1-2}OH$, —NO, —$NO_2$, —$N_3$, —$NH_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —$CO_2H$, CO—$C_{1-2}$- alkyl, —CO—$C_{6-10}$-aryl and —CO-heteroaryl.

For the purpose of the description, capable of preferably stereoselectively reducing a keto substrate means that in the presence of a suitable cofactor under suitable conditions (preferably in water at pH 7.0 and 37° C.) the ketoreductase exhibits at least some activity against at least one keto substrate thereby yielding a secondary alcohol.

For the purpose of the description, saturated or unsaturated aliphatic $C_{1-12}$-hydrocarbon residues include but are not limited to alkyl, alkenyl and alkynyl residues, such as —$CH_3$, —$CH_2CH_3$, —$CH_2CH_2CH_3$, —CH($CH_3$)$_2$, —$CH_2CH_2CH_2CH_3$, —CH($CH_3$)$CH_2CH_3$, —$CH_2CH$($CH_3$)$_2$, —C($CH_3$)$_3$, —CH=$CH_2$, —CH=CHCH=$CH_2$, —C≡CH, and —CH=CHC≡CH, For the purpose of the description, saturated or unsaturated alicyclic $C_{1-12}$-hydrocarbon residues include but are not limited to $C_{3-12}$-cycloalkyl, wherein 1 or 2 carbon ring atoms may optionally be replaced by heteroatoms selected from N, O and S ($C_{1-12}$-heterocycloalkyl).

For the purpose of the description, $C_{6-10}$-aromatic hydrocarbon residues (=$C_{6-10}$-aryl) include but are not limited to phenyl and naphthyl.

For the purpose of the description, heteroaromatic hydrocarbon residues (=heteroaryl) include but are not limited to monocyclic ring systems, bicyclic ring systems and tricyclic ring systems. Examples of monocyclic heteroaryls include but are not limited to azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Examples of bicyclic heteroaryls include but are not limited to benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Examples of tricyclic heteroaryls include but are not limited to acridinyl, carbazolyl, carbolinyl, dibenzo(b,d)furanyl, dibenzo(b,d)thienyl, naphtho(2,3-b)furan, naphtho(2,3-b)thienyl, phenazinyl, phenothiazinyl, phenoxazinyl, thianthrenyl, thioxanthenyl and xanthenyl.

For the purpose of the description, mono- or polysubstituted with regard to alkyl (e.g. —$C_{1-12}$-alkyl), cycloalkyl (e.g. —$C_{3-8}$-cycloalkyl), aryl (e.g. —$C_{6-10}$-aryl) and heteroaryl, respectively, preferably independently means replacement of a hydrogen from the core by one or more functional groups selected from -halo (preferably —F, —Cl, —Br, —I), —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —$S(=O)_{1-2}OH$, —NO, —$NO_2$, —$N_3$, —$NH_2$, —$NH(C_{1-12}$-alkyl), —$N(C_{1-12}$-alkyl$)_2$, —$NH(C_{6-10}$-aryl), —$N(C_{6-10}$-aryl$)_2$, —NH(heteroaryl), —N(heteroaryl$)_2$, —CN, —CHO, —$CO_2H$, CO—$C_{1-2}$-alkyl, —CO—$C_{6-10}$-aryl and —CO-heteroaryl.

For the purpose of the description, sugar residues or desoxysugar residues in each case comprising mono-, di- or oligosaccharides means that the keto substrate of general formula (I) or the aldehyde substrate of general formula (I') may be a polyhydroxycarbonyl compound, optionally linked to other polyhydroxycarbonyl compounds through acetal and/or ketal bonds. For example, when X is $C_1$ alkyl monosubstituted with —OH and Y is $C_2$ alkyl polysubstituted with —OH, wherein every carbon atom bears a single —OH substituent, the keto substrate of general formula (I) is a ketotetrose encompassing both enantiomers, D-erythrulose as well as L-erythrulose. Analogously, the keto substrate of general formula (I) may be a ketopentose or a ketohexose which in turn may be linked to other sugar residues thus forming disaccharides or oligosaccharides. Correspondingly, when X is $C_2$ alkyl polysubstituted with —OH, wherein every carbon atom bears a single —OH substituent, the aldehyde substrate of general formula (I') is an aldotriose encompassing both enantiomers, D-glycerinaldehyde as well as L-glycerinaldehyde. Analogously, the aldehyde substrate of general formula (I') may be a aldotetrose, aldopentose or a aldohexose which in turn may be linked to other sugar residues thus forming disaccharides or oligosaccharides.

In a preferred embodiment, the ketoreductase according to the invention is capable of stereoselectively reducing a keto substrate selected from the group consisting of (i) 3-aryl-3-ketopropanamine-derivatives according to general formula (II)

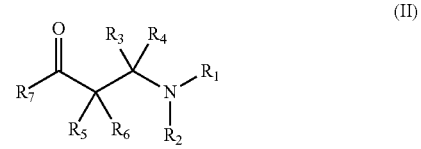

(II)

wherein $R_1$ and $R_2$ are each independently selected from the group consisting of —H; unsubstituted or mono- or polysubstituted —$C_{1-12}$-alkyl; unsubstituted or mono- or polysubstituted —$C_{3-8}$-cycloalkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; or unsubstituted or mono- or polysubstituted heteroaryl, optionally being bridged through a saturated or unsaturated, unsubstituted or mono- or polysubstituted aliphatic $C_{1-12}$-hydrocarbon residue; or alternatively, wherein $R_1$ and $R_2$ together with the nitrogen atom to which they are attached form an unsubstituted or mono- or polysubstituted $C_{2-8}$-heterocycloalkyl ring or an unsubstituted or mono- or polysubstituted heteroaryl ring;

preferably, $R_1$ and $R_2$ are —$C_{1-12}$-alkyl; more preferably —$CH_3$;

$R_3$, $R_4$, $R_5$, and $R_6$ are each independently selected from —H; unsubstituted or mono- or polysubstituted —$C_{1-12}$-alkyl; or wherein $R_3$ and $R_4$ together are =O;

preferably, $R_3$ and $R_4$ together are =O, and $R_5$ and $R_6$ are —H; and $R_7$ is unsubstituted or mono- or polysubstituted —$C_{6-10}$-aryl; or unsubstituted or mono- or polysubstituted-heteroaryl;

preferably, $R_7$ is unsubstituted, mono- or polysubstituted heteroaryl; more preferably unsubstituted heteroaryl; most preferably thienyl; in particular 2-thienyl;

wherein a particularly preferred keto substrate of this type is N,N-dimethyl-3-keto-3-(2-thienyl)-1-ketopropanamine

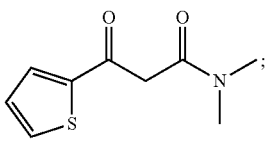

wherein another particularly preferred keto substrate of this type is N-monomethyl-3-keto-3-(2-thienyl)-1-ketopropanamine

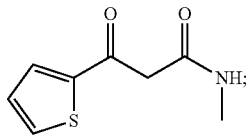

(ii) 5-hydroxy-3-oxo-hexanoate-derivatives according to general formula (III)

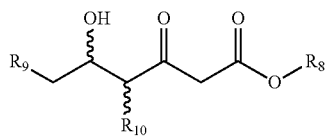

wherein
- $R_8$ is unsubstituted or mono- or polysubstituted —$C_{1-12}$-alkyl; or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; preferably, $R_8$ is —$C_{1-12}$-alkyl; more preferably —$C(CH_3)_3$;
- $R_9$ is —H; -halo (preferably chloro, bromo, iodo); —CN; or —$OR_{11}$, wherein $R_{11}$ is hydrogen or a protecting group (like benzyloxy); preferably, $R_9$ is -halo or —CN; more preferably —Cl or —CN;
- $R_{10}$ is —H; unsubstituted or mono- or polysubstituted —$C_{1-12}$-alkyl; or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; preferably, $R_{10}$ is —H;
- wherein a particularly preferred keto substrate of this type is tert-butyl (5S)-6-chloro-5-hydroxy-3-oxo-hexanoate

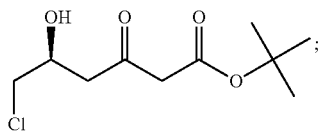

wherein a particularly preferred keto substrate of this type is tert-butyl (5R)-6-cyano-5-hydroxy-3-oxo-hexanoate

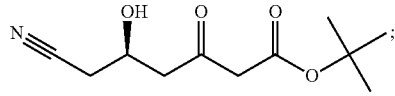 [SMILES: CC(C)(C)OC(=O)CC(=O)C[C@H](O)CC#N]

(iii) acetophenone-derivatives according to general formula (IV)

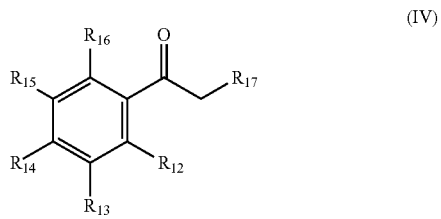

wherein
- $R_{12}$, $R_{13}$, $R_{14}$, $R_{15}$, and $R_{16}$ are each independently selected from the group consisting of —H; -halo (preferably chloro, bromo and iodo); unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; unsubstituted or mono- or polysubstituted -heteroaryl, optionally being bridged through a saturated or unsaturated, unsubstituted or mono- or polysubstituted aliphatic $C_{1-12}$-hydrocarbon residue; and —$OR_{18}$, wherein $R_{18}$ is —H, unsubstituted or mono- or polysubstituted —$C_{1-12}$-alkyl, or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue;
  preferably, $R_{12}$, $R_{13}$, $R_{14}$, $R_{15}$, and $R_{16}$ are independently —H, -halo, or $OR_{18}$; more preferably —H, —Cl, or $OCH_3$;
- $R_{17}$ is —H; -halo (preferably chloro, bromo and iodo); unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; unsubstituted or mono- or polysubstituted -heteroaryl, optionally being bridged through a saturated or unsaturated, unsubstituted or mono- or polysubstituted aliphatic $C_{1-12}$-hydrocarbon residue; —$OR_{19}$, —$NH_2$, —$NHR_{19}$, or —$NR_{19}R_{20}$, wherein $R_{19}$ and $R_{20}$ are each independently selected from unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; or unsubstituted or mono- or polysubstituted -heteroaryl, optionally being bridged through a saturated or unsaturated, unsubstituted or mono- or polysubstituted aliphatic $C_{1-12}$-hydrocarbon residue;

preferably, $R_{17}$ is —H;

wherein a particularly preferred keto substrate of this type is 1-(4-chlorophenyl)ethanone,

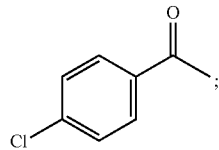

or wherein a particularly preferred keto substrate of this type is 1-(2-methoxyphenyl)ethanone

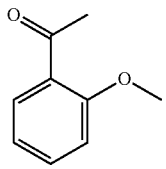

(iv) benzoyl-derivatives according to general formula (V)

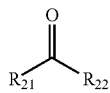

(V)

wherein
  $R_{21}$ and $R_{22}$ are each independently selected from unsubstituted or mono- or polysubstituted $C_{6-10}$-aryl and unsubstituted or mono- or polysubstituted heteroaryl;
    preferably $R_{21}$ is unsubstituted or mono- or polysubstituted $C_{6-10}$-aryl and $R_{22}$ is unsubstituted or mono- or polysubstituted heteroaryl; more preferably $R_{21}$ is unsubstituted $C_{6-10}$-aryl and $R_{22}$ is unsubstituted heteroaryl;
    wherein a particularly preferred keto substrate of this type is phenyl-(2-pyridyl)-methanone

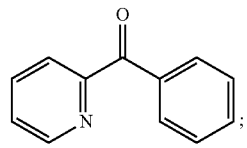 [SMILES: O=C(c1ccccc1)c1ccccn1]

(v) secodione-derivatives according to general formula (VI)

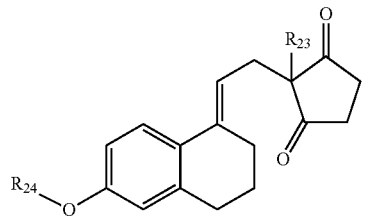

(VI)

wherein
  $R_{23}$ and $R_{24}$ are each independently selected from the group consisting of —H and —$C_{1-12}$-alkyl; and preferably $R_{23}$ is —$CH_2CH_3$ and $R_{24}$ is —$C_{1-12}$-alkyl; more preferably $R_{23}$ is —$CH_2CH_3$ and $R_{24}$ is —$CH_3$;
    wherein a particularly preferred keto substrate of this type is ethylsecodion (ethyl-3-methoxy-8,14-seco-gona-1,3,5(10),9(11)-tetraen-14,17-dione)

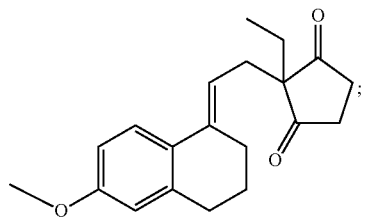 [SMILES: CCC1(C/C=C2\CCCc3cc(OC)ccc32)C(=O)CCC1=O]

(vi) 3-quinuclidone (i.e., 1-azabicyclo[2.2.2]octan-3-one);
(vii) ethyl-4-chloro-3-oxo-butanoate;
(viii) ethyl-3-oxo-3-phenyl-propanoate; and
(ix) ketose, preferably ketotetrose, ketopentose or ketohexose;
or the ketoreductase according to the invention is capable of preferably stereospecifically reducing a an aldehyde substrate selected from the group consisting of
(x) 2-butanal (synonymous to isobutyraldehyde) (as this keto substrate is a non-prochiral aldehyde, the reduction does not proceed stereoselectively); and
(xi) 1-heptanal (as this keto substrate is a non-prochiral aldehyde, the reduction does not proceed stereoselectively);
wherein in each case mono- or polysubstituted means independently substituted with one or more functional groups selected from -halo, —OH, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —$S(=O)_{1-2}OH$, —NO, —$NO_2$, —$N_3$, —$NH_2$, —NH($C_{1-12}$-lkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —$CO_2H$, CO—$C_{1-2}$- alkyl, —CO—$C_{6-10}$-aryl and —CO-heteroaryl.

In some embodiments of the invention, the ketoreductases according to the invention are capable of reducing aldehyde substrates or capable of preferably stereoselectively reducing keto substrates according to general formulas (I) to (VI), or 3-quinuclidone, or ethyl-4-chloro-3-oxo-butanoate, ethyl-3-oxo-3-phenyl-propanoate, 2-butanal or 1-heptanal, as defined above, to the respective primary or secondary alcohols. In some embodiments of the invention, the ketoreductases according to the invention are capable of oxidizing aldehyde substrates such as 2-butanal or 1-heptanal to the corresponding carboxylic acids.

In some embodiments the ketoreductases according to the invention are capable of stereoselectively reducing 3-aryl-3-ketopropanamine-derivatives according to general formula (II), preferably N,N-dimethyl-3-keto-3-(2-thienyl)-1-ketopropanamine to preferably (1S)-3-(dimethylamino)-1-(2-thienyl)-propan-1-ol. Examples for such ketoreductases comprise an amino acid sequence according to SEQ ID NO:47, 49, 50, 51, 52, 53, 54, 55, 56, 57, 58, 59, 62, 72, 85, 86, 87, 88, or 89; preferably SEQ ID NO:55, 58, or 87; and most preferably SEQ ID NO:58.

In some embodiments the ketoreductases according to the invention are capable of stereoselectively reducing 3-aryl-3-ketopropanamine-derivatives according to general formula (II), preferably N-monomethyl-3-keto-3-(2-thienyl)-1-ketopropanamine to preferably (1S)-3-(methylamino)-1-(2-thienyl)-propan-1-ol. Examples for such ketoreductases comprise an amino acid sequence according to SEQ ID NO:19, 28, 40, 46, 47, 49, 50, 55, 56, 57, 58, 59, 62, 64, 67, 72, 81, 82, 83, 85, 86, 87, 88, 89, 92, or 93, preferably SEQ ID NO:58, 87, or 92, and most preferably SEQ ID NO:87.

In some embodiments the ketoreductases according to the invention are capable of stereoselectively reducing 5-hydroxy-3-oxo-hexanoate-derivatives according to general formula (III), preferably tert-butyl (5S)-6-chloro-5-hydroxy-3-oxohexanoate to preferably tert-butyl (3R,5S)-6-chloro-3,5-dihydroxy-hexanoate. Examples for such ketoreductases comprise an amino acid sequence according to SEQ ID NO:34, 36, 40, 49, 53, 54, 55, 60, 61, 62, 64, 65, 66, 67, 68, 70, 72, 73, 74, 75, 76, 77, 78, 81, 82, 83, 92, or 93, preferably SEQ ID NO:62, 91, or 92, and most preferably SEQ ID NO:91.

In some embodiments the ketoreductases according to the invention are capable of stereoselectively reducing 5-hydroxy-3-oxo-hexanoate-derivatives according to general formula (III), preferably tert-butyl (5R)-6-cyano-5-hydroxy-3-oxo-hexanoate to preferably tert-butyl (3R,5R)-6-cyano-3,5-dihydroxy-hexanoate. Examples for such ketoreductases comprise an amino acid sequence according to SEQ ID NO:34, 36, 40, 49, 55, 60, 61, 62, 64, 65, 66, 67, 68, 69, 70, 71, 72, 73, 74, 75, 76, 77, 78, 81, 82, 83, 84, 92, or 93, preferably SEQ ID NO:62, 91, or 92, and most preferably SEQ ID NO:91.

In some embodiments the ketoreductases according to the invention are capable of stereoselectively reducing acetophenone-derivatives according to general formula (IV), preferably 1-(4-chlorophenyl)ethanone to 1-(4-chlorophenyl)ethanol. Examples for such ketoreductases comprise an amino acid sequence according to SEQ ID NO: 7, 9, 12, 15, 17, 18, 23, 24, 28, 31, 36, 38, 39, 47, 48, 49, 50, 51, 52, 53, 54, 55, 58, 62, 72, 81, 82, 83, 87, or 92, preferably SEQ ID NO:7, 15, or 28, and most preferably SEQ ID NO:28.

In some embodiments the ketoreductases according to the invention are capable of stereoselectively reducing acetophenone-derivatives according to general formula (IV), preferably 1-(2-methoxyphenyl)ethanone to 1-(2-methoxyphenyl)ethanol. Examples for such ketoreductases comprise an amino acid sequence according to SEQ ID NO:15, 17, 22, 24, 26, 36, 38, 40, 58, 60, 61, 62, 64, 65, 66, 67, 68, 69, 70, 71, 72, 73, 75, 76, 77, 78, 81, 82, 83, 86, 92, or 93, preferably SEQ ID NO:17, 72, or 92, and most preferably SEQ ID NO:72.

In some embodiments the ketoreductases according to the invention are capable of stereoselectively reducing benzoyl-derivatives according to general formula (V), preferably phenyl-(2-pyridyl)-methanone to phenyl-(2-pyridyl)-methanol. Examples for such ketoreductases comprise an amino acid sequence according to SEQ ID NO:21, 24, 28, 36, 38, 39, 40, 44, 46, 47, 48, 49, 50, 51, 52, 53, 54, 55, 56, 57, 58, 59, 60, 61, 62, 64, 65, 66, 67, 68, 69, 70, 71, 72, 73, 74, 75, 76, 77, 78, 81, 82, 83, 85, 86, 87, 88, 89, 92, or 93, preferably SEQ ID NO:72, 82, or 92, and most preferably SEQ ID NO:72.

In some embodiments the ketoreductases according to the invention are capable of stereoselectively reducing secodione-derivatives according to general formula (VI), preferably ethylsecodion (ethyl-3-methoxy-8,14-seco-gona-1,3,5(10),9(11)-tetraen-14,17-dione) to preferably ethylseconol (ethyl-3-methoxy-8,14-seco-gona-1,3,5(10),9(11)-tetraen-14-on-17-β-ol). Examples for such ketoreductases comprise an amino acid sequence according to SEQ ID NO:61, 62, 65, 66, 69, 70, 71, 75, 78, 82, 83, 86, 92, or 93, preferably SEQ ID NO:69, 70 or 71, and most preferably SEQ ID NO:70.

In some embodiments the ketoreductases according to the invention are capable of stereoselectively reducing the keto substrate ethyl 3-oxo-3-phenyl-propanoate to ethyl 3-hydroxy-3-phenyl-propanoate. Examples for such ketoreductases comprise an amino acid sequence according to SEQ ID NO: 17, 34, 36, 40, 46, 47, 52, 60, 61, 62, 64, 65, 66, 67, 68, 70, 71, 72, 73, 74, 75, 76, 77, 78, 81, 82, 83, 84, 92, or 93, preferably SEQ ID NO:46, 76, or 78, and most preferably SEQ ID NO:76.

In some embodiments the ketoreductases according to the invention are capable of stereoselectively reducing the keto substrate ethyl-4-chloro-3-oxo-butanoate to preferably ethyl (3S)-4-chloro-3-hydroxy-butanoate. Examples for such ketoreductases comprise an amino acid sequence according to SEQ ID NO:2, 63 or 90.

In some embodiments the ketoreductases according to the invention are capable of stereoselectively reducing the keto substrate 3-Quinuclidone (synonymous to 1-azabicyclo[2.2.2]octan-3-one hydrochloride) to 3-Quinuclidinol (synonymous to 1-azabicyclo[2.2.2]octan-3-ol). Examples for such ketoreductases comprise an amino acid sequence according to SEQ ID NO:17, 21, 26, 38, 40, 62, 72, 73, 81, 83, 86, 92, or 93, preferably SEQ ID NO:17, 21, or 73, and most preferably SEQ ID NO:17.

In some embodiments, the ketoreductases according to the invention are capable of oxidizing a secondary alcohol to the corresponding ketone, e.g. oxidizing 2-butanol to 2-butanal.

In some embodiments, the ketoreductases according to the invention are capable of oxidizing a primary alcohol to an aldehyde compound, e. g. oxidizing 1-heptanol to 1-heptanal.

In some embodiments, the ketoreductases according to the invention are capable of oxidizing an aldehyde compound to a carboxylic acid.

Preferably, the ketoreductase according to the invention is capable of oxidizing a cosubstrate for cofactor regeneration at a high specific activity, preferably at a specific activity of 0.1-100 U/mg, more preferably, 1-50 U/mg, and most preferably of 10-12 U/mg lyophilisate of ketoreductase. Cosubstrates in the meaning of the invention are primary or secondary alcohols that are converted (preferably oxidized) by a ketoreductase according to the invention concomitantly to the conversion (preferably reduction) of a keto substrate.

Suitable cosubstrates established for cofactor regeneration may be selected according their specific activity, preferably from the group consisting of isopropyl alcohol, 2-butanol, 2-pentanol, 2-hexanol and 2-heptanol. Preferably, a ketoreductase according to the invention converts isopropyl alcohol to acetone at a high specific activity. An ketoreductase lyophilisate may be obtained e.g. by disruption of the cells as described in example 2 (see below) and subsequent lyophilisation of the crude extract.

For determination of oxidation activity with respect to a given cosubstrate, the ketoreductase according to the invention is preferably incubated in a buffer containing 20% the cosubstrate, for example isopropyl alcohol, and a cofactor, for example 0.25 mM of NAD(P) at 30° C. The oxidation activity is determined by measuring the decrease of absorbance at 340 nm resulting from NAD(P) reduction. Under the specified conditions the ketoreductase having the amino acid sequence of SEQ ID NO:2 exhibits a specific activity of 10.6 U/mg ketoreductase lyophilisate for isopropyl alcohol oxidation.

Preferably, the ketoreductases according to the invention exhibit a high stability in cosubstrates, preferably in isopropyl alcohol, 2-butanol, 2-pentanol, 2-hexanol and/or 2-heptanol. Preferably, after 48 h pre-incubation of the ketoreductase at 30° C. in 50% aqueous cosubstrate, preferably isopropyl alcohol, the ketoreductase exhibits a residual activity of at least 1%, more preferably at least 10% or at least 20%, still more preferably at least 30% or at least 40%, yet more preferably at least 50% or at least 60%, even more preferably at least 70% or at least 80%, most preferably at least 85% or at least 90%, in particular at least 95% or at least 99%, relative to its activity before pre-incubation. In this regard, residual activity in the meaning of this invention describes the remaining ketoreductase activity of an enzyme after pre-incubation with a cosubstrate compared to the activity after pre-incubation without the cosubstrate. For determination of stability in cosubstrate, including e.g. isopropyl alcohol, the ketoreductase according to the invention is pre-incubated in a buffer, preferably at pH 9, containing 50% cosubstrate, e.g. isopropyl alcohol, at 30° C. for 48 h, and the enzyme activity of the ketoreductase is compared to an enzyme pre-incubated without cosubstrate. The residual activity of the ketoreductase according the invention is 100%, when both enzyme activities are identical; i.e. when there is no loss of activity as compared to the activity under pre-incubation without cosubstrate. Under the described conditions the ketoreductase having the amino acid sequence of SEQ ID NO:2 exhibits a residual activity of 100%.

An efficient conversion of cosubstrates by the ketoreductase and the ketoreductase stability in cosubstrate are of particular relevance for the setup of efficient industrial processes for the reduction of keto or aldehyde substrates to secondary or primary alcohols. The stability of the ketoreductases of the invention in cosubstrate and their capability of conversion of cosubstrates according the invention is also of relevance for the reverse conversion of primary and secondary alcohols to aldehyde and keto substrates.

In some embodiments the ketoreductases according to the invention exhibit an improved specific activity, temperature stability, and/or stereoselectivity upon engineering of the SEQ ID NO:2.

An improved specific activity according to the invention relates to a specific activity of an engineered ketoreductase which is higher than the specific activity of the non-engineered ketoreductase. Preferably, the specific activity is at least 10%, at least 50%, at least 100%, at least 1.5 times, at least 2 times, at least 3 times, at least 5 times, at least 10 times, at least 20 times, at least 50 times, at least 100 times, at least 200 times, at least 300 times, at least 500 times, at least 700 times, at least 1000 times, at least 10.000 times, or at least 100.000 times higher than the specific activity of the non-engineered ketoreductase. The improved specific activity may also mean that the engineered ketoreductase does exhibit a certain activity towards the desired substrate, whereas the non-engineered ketoreductase has no significant activity towards said substrate.

An improved temperature stability according to the invention relates to a higher residual specific activity of an engineered ketoreductase after 48 h incubation at 30° C. in comparison with the non-engineered ketoreductase of SEQ ID NO:2. Alternatively, an improved temperature stability according to this invention can relate to the same residual specific activity of an engineered ketoreductase in comparison with the non-engineered ketoreductase after incubation for the same at a higher temperature, or for a longer time at the same temperature.

An improved stereoselectivity according to the invention relates to an enantiomeric excess of the product provided by means of an engineered ketoreductase which is higher than the enantiomeric excess of the product provided by means of the non-engineered ketoreductase of SEQ ID NO:2. Preferably, the enantiomeric excess provided by an engineered ketoreductase is increased by at least 0.1% ee, at least 0.5% ee, at least 1% ee, at least 2% ee, at least 3% ee, at least 5% ee, at least 7% ee, at least 10% ee, at least 20% ee, at least 30% ee, at least 40% ee, at least 50% ee, at least 60% ee, at least 70% ee, at least 80% ee, at least 90% ee, at least 95% ee, at least 97% ee, at least 98% ee, or at least 99% ee compared to the non-engineered ketoreductase. The improved stereoselectivity may also mean that the engineered ketoreductase does have a certain stereoselectivity towards the desired chiral product, whereas the non-engineered ketoreductase has no significant stereoselectivity towards said chiral product.

Improved specific activity of the engineered ketoreductase compared to the non-engineered ketoreductase of SEQ ID NO:2 is preferably determined under standardized reaction conditions, typically at 30° C. in buffered aqueous solution, containing substrate, cofactor, optional supplements and ketoreductase. The buffer is preferably selected from the group consisting of 10-200 mM Tris/HCl at pH 7-9 containing 2 mM $MgCl_2$, 10-200 mM sodium phosphate/NaOH at pH 6-8, or 10-200 mM triethanoleamine/HCl at pH 7-9. The cofactor NADH is preferably added to a final concentration ranging from 0.05 to 10 mM. The substrate, which is preferably added to a final concentration ranging from 5 mM to 1 M, is preferably selected from the group consisting of ethyl-4-chloro-3-oxo-butanoate, 1-(4-chlorophenyl)ethanone, 1-(2-methoxyphenyl)ethanol, tert-butyl (5R)-6-cyano-5-hydroxy-3-oxo-hexanoate, N,N-dimethyl-3-keto-3-(2-thienyl)-1-ketopropanamine, ethylsecodion (ethyl-3-methoxy-8,14-seco-gona-1,3,5(10),9(11)-tetraen-14,17- dione), tert-butyl (5S)-6-chloro-5-hydroxy-3-oxo-hexanoate, and N-monomethyl-3-keto-3-(2-thienyl)-1-ketopropanamine, phenyl-(2-pyridyl)-methanone, ethyl 3-oxo-3-phenyl-propanoate, 3-quinuclidone, 2-butanal and 1-heptanal. Optional other supplements are preferably selected from the group consisting of 1-5% Triton™ X-100 (v/v), and 0.5 to 10% DMSO (v/v). The ketoreductase is preferably added as crude extract supernatant. The crude extract is obtained by disruption of the expression host containing the ketoreductase and subsequent centrifugation to separate the cell debris and the ketoreductase containing supernatant of the crude extract. The specific activity is preferably determined by measuring product formation, depletion of the reduced cofactor NADH, and/or substrate depletion. In case the specific activity is determined by measuring product formation or substrate depletion, a cofactor regeneration system (isopropanol or GDH/glucose) may be applied in the standard reaction. No cofactor regeneration system is applied, in case the specific activity is determined by measuring depletion of the reduced cofactor NADH. In case a cofactor regeneration system is applied the reduced cofactor NADH can be substituted by the oxidized cofactor NAD$^+$, which is reduced by the cofactor regeneration system.

Improved stereoselectivity of the engineered ketoreductase compared to the non-engineered ketoreductase of SEQ ID NO:2 is preferably determined under standardized reaction conditions as described above for the determination of the improved specific activity. A chiral analytic is applied to analyze the product formed in the reaction.

Improved temperature stability of the engineered ketoreductase compared to the non-engineered ketoreductase of SEQ ID NO:2 is preferably determined by incubation of the ketoreductase containing crude extract for 15 minutes at a given temperature (preferably the temperature, at which the non-engineered ketoreductase of SEQ ID NO:2 exhibits a residual activity of 10%) in a PCR cycler. Afterwards the crude extract is incubated on ice for 30 minutes. Insoluble proteins are separated by centrifugation and the supernatant is analyzed regarding its remaining ketoreductase activity in a standard ketoreductase assay. In this standard assay a suitable substrate for the ketoreductase, e.g. isopropyl alcohol is oxidized e.g. to acetone, by the ketoreductase with concomitant reduction of NAD$^+$ to NADH (since no other ketoreductase substrate is present in this standard assay, isopropyl alcohol functions as substrate for the ketoreductase and is not applied for cofactor regeneration). The increase of NADH is monitored by measuring the absorption at 340 nm in a standard photometer. The assay is carried out under standardized reaction conditions, i. e. typically at 30° C. in buffered aqueous solution, containing substrate (e.g. isopropyl alcohol), cofactor and ketoreducase. The ketoreductase is preferably added as crude extract supernatant. The crude extract is obtained by disruption of the expression host containing the ketoreductase and subsequent centrifugation to separate the cell debris and the ketoreductase containing supernatant of the crude extract. The buffer is preferably selected from the group consisting of 10-200 mM Tris/HCl at pH 7-9 containing 2 mM MgCl$_2$, 10-200 mM sodium phosphate/NaOH at pH 6-8, or 10-200 mM triethanoleamine/HCl at pH 7-9. The cofactor NAD$^+$ is preferably added to a final concentration ranging from 0.05 to 10 mM. The ketoreductase is preferably added as crude extract supernatant. The crude extract is obtained by disruption of the expression host containing the ketoreductase and subsequent centrifugation to separate the cell debris and the ketoreductase containing supernatant of the crude extract.

In a preferred embodiment, the engineered ketoreductase according to the invention differs from the wild type ketoreductase of SEQ ID NO:2 by 1 to 70 amino acids, typically by 1 to 50 amino acids, more typically by 1 to 30 amino acids, even more typically by 1 to 20 amino acids, and most typically by 1 to 11 amino acids.

In this regard, engineering means that one or more amino acids in a given position are substituted with any other proteinogenic amino acid selected from the group consisting of Ala, Arg, Asn, Asp, Cys, Gln, Glu, Gly, His, Ile, Leu, Lys, Met, Phe, Pro, Ser, Thr, Trp Tyr, and Val. In a preferred embodiment, the substitution does not alter the sequence length, i.e. a single amino acid residue is replaced by another single amino acid residue. However, it is also possible to delete one or more amino acid residues without replacement and/or to insert one or more amino acid residues.

In principle, a substitution in any position of an enzyme may be a conservative substitution where such amino acid is substituted with an amino acid of comparable characteristics (e.g. substitution of a hydrophobic amino acid with another hydrophobic amino acid). In addition, a substitution in any position of an enzyme may be a non-conservative substitution where such amino acid is substituted with an amino acid of other characteristics (e.g. substitution of a hydrophobic amino acid with a hydrophilic amino acid).

The technique of enzyme engineering is reviewed in: S. Lutz, U. T. Bornscheuer, Protein Engineering Handbook, Wiley VCH, Weinheim, 2009.

Any substitution according to this invention excludes amino acid substitutions in positions of the ketoreductase according to the invention, which are indispensable for the catalytic activity of the ketoreductase, preferably positions N120, S148, Y161 and K165 of SEQ ID NO:2. It is furthermore known in the state of the art, that sequence positions participating in predictable protein structure elements, e.g. alpha helices, or beta sheets, or ionic interactions, are sensitive to mutagenesis and may require no substitution or only concomitant substitution with a counter-position.

The invention also relates to engineered ketoreductases that differ from the amino acid sequence of the wild type ketoreductase of SEQ ID NO:2 by 1 to 70 residue changes, preferably by 1 to 50 residue changes, more preferably by 1 to 30 residue changes, even more preferably by 1 to 20 residue changes, and most preferably by 1 to 11 residue changes, preferably including changes at one or more of the following positions of SEQ ID NO:2: Y21, V23, S33, L39, R40, A43, P68, V89, G95, P97, T98, D103, G109, V119, L121, V124, Y125, I149, L150, S154, E155, T157, A158, T163, H190, Y193, L198, L199, A201, A206, Y207, V229, and V247.

Preferably, the engineered ketoreductase according to the invention differs from the amino acid sequence of the wild type ketoreductase of SEQ ID NO:2 by 1 to 70, more preferably by 1 to 50, still more preferably by 1 to 30, even more preferably by 1 to 20, and most preferably by 1 to 11 residue changes, preferably including one or more of the following residue changes:

Y21Q;
V23T;
S33A;
L39V;
R40C;
A43E or G;
P68S;
V89F;
G95A, E, M, Q, S or V;
P97A, E, K, N, V or Y;
T98A or G;
D103E;
G109Y;
V119Y;
L121Q;
V124I;
Y125F;
I149A, G, L, M, Q, T or V;
L150A, F, H or S;
S154G;
E155A, D, F, G, K, L or S;
T157Y;

A158G, L, P, Q, S, V or W;
R163A or S;
H190C;
Y193A, F, G, P, T or V;
L198M;
L199A, F, I or T;
A201G;
A206G;
Y207R or L;
V229I; and/or
V247I.

Preferably, the engineered ketoreductases according to the invention are capable of reducing any aldehyde substrate or are capable of stereoselectively reducing any keto substrate, preferably the keto substrate of general formula (I); or the 3-aryl-3-ketopropanamine-derivatives according to general formula (II); or the 5-hydroxy-3-oxo-hexanoate-derivatives according to general formula (III); or the acetophenone-derivatives according to general formula (IV); or the benzoyl-derivatives according to general formula (V); or the secodione-derivatives according to general formula (VI); or 3-quinuclidone; or ethyl-3-oxo-3-phenyl-propanoate; or ethyl-4-chloro-3-oxo-butanoate; or ketose; or the aldehyde substrate accoding to general formula (I'); or 2-butanal; or 1-heptanal; and preferably exhibit an improved specific activity, temperature stability, and/or stereoselectivity compared to the wild type ketoreductase of SEQ ID NO:2.

Preferably, the engineered ketoreductases according to the invention are capable of reducing any aldehyde substrate or any keto substrate, preferably the keto substrate of general formula (I); or the 3-aryl-3-ketopropanamine-derivatives according to general formula (II); or the 5-hydroxy-3-oxo-hexanoate-derivatives according to general formula (III); or the acetophenone-derivatives according to general formula (IV); or the benzoyl-derivatives according to general formula (V); or the secodione-derivatives according to general formula (VI); or 3-quinuclidone; or ethyl-3-oxo-3-phenyl-propanoate; ethyl-4-chloro-3-oxo-butanoate; or ketose; or the aldehyde substrate accoding to general formula (I'); or 2-butanal; or 1-heptanal; and differ from the amino acid sequence of the wild type ketoreductase of SEQ ID NO:2 by 1 to 70 amino acids, preferably by 1 to 50 amino acids, more preferably by 1 to 30 amino acids, even more preferably by 1 to 20 amino acids, and most preferably by 1 to 11 residue changes, preferably including changes at one or more of the following positions: Y21, V23, S33, L39, R40, A43, P68, V89, G95, P97, T98, D103, G109, V119, L121, V124, Y125, I149, L150, 5154, E155, T157, A158, T163, H190, Y193, L198, L199, A201, A206, Y207, V229, and V247.

Preferably, the engineered ketoreductases according to the invention are capable of reducing any aldehyde substrate or are capable of stereoselectively reducing any keto substrate, preferably the keto substrate of general formula (I); or the 3-aryl-3-ketopropanamine-derivatives according to general formula (II); or the 5-hydroxy-3-oxo-hexanoate-derivatives according to general formula (III); or the acetophenone-derivatives according to general formula (IV); or the benzoyl-derivatives according to general formula (V); or the secodione-derivatives according to general formula (VI); or 3-quinuclidone; or ethyl-3-oxo-3-phenyl-propanoate; ethyl-4-chloro-3-oxo-butanoate; or ketose; or the aldehyde substrate accoding to general formula (I'); or 2-butanal; or 1-heptanal; and differ from the amino acid sequence of the wild type ketoreductase of SEQ ID NO:2 by 1 to 70, preferably by 1 to 50, more preferably by 1 to 30, even more preferably by 1 to 20, and most preferably by 1 to 11 residue changes, preferably including one or more of the following residue changes: Y21Q; V23T; S33A; L39V; R40C; A43E or G; P68S; V89F; G95A; E, M, Q, S or V; P97A, E, K, N, V or Y; T98A or G; D103E; G109Y; V119Y; L121Q; V124I; Y125F; I149A, G, L, M, Q, T or V; L150A, F, H or S; S154G; E155A, D, F, G, K, L or S; T157Y; A158G, L, P, Q, S, V or W; T163A or S; H190C; Y193A, F, G, P, T or V; L198M; L199A, F, I or T; A201G; A206G; Y207R or L; V229I; and V247I.

Preferably, the engineered ketoreductases according to the invention are capable of sterespecifically reducing one of the following substrates: N,N-dimethyl-3-keto-3-(2-thienyl)-1-ketopropanamine, N-monomethyl-3-keto-3-(2-thienye-1-ketopropanamine, tert-butyl (5R)-6-cyano-5-hydroxy-3-oxo-hexanoate, tert-butyl (5S)-6-chloro-5-hydroxy-3-oxo-hexanoate, 1-(4-chlorophenyl)ethanone, 1-(2-methoxyphenyl)ethanone, phenyl-(2-pyridyl)-methanone, ethylsecodion, ethyl 3-oxo-3-phenyl-propanoate, 3-quinuclidone, ethyl-4-chloro-3-oxo-butanoate; or ketose; or the aldehyde substrate accoding to general formula (I'); or 2-butanal; or 1-heptanal; and differ from the amino acid sequence of the wild type ketoreductase of SEQ ID NO:2 by 1 to 70 amino acids, preferably by 1 to 50 amino acids, more preferably by 1 to 30 amino acids, even more preferably by 1 to 20 amino acids, and most preferably by 1 to 11 residue changes, preferably including changes at one or more of the following positions: Y21, V23, S33, L39, R40, A43, P68, V89, G95, P97, T98, D103, G109, V119, L121, V124, Y125, I149, L150, S154, E155, T157, A158, T163, H190, Y193, L198, L199, A201, A206, Y207, V229, and V247.

Preferably, the engineered ketoreductases according to the invention are capable of sterespecifically reducing one of the following substrates: N,N-dimethyl-3-keto-3-(2-thienyl)-1-ketopropanamine, N-monomethyl-3-keto-3-(2-thienye-1-ketopropanamine, tert-butyl (5R)-6-cyano-5-hydroxy-3-oxo-hexanoate, tert-butyl (5S)-6-chloro-5-hydroxy-3-oxohexanoate, 1-(4-chlorophenyl)ethanone, 1-(2-methoxyphenyl)ethanone, phenyl-(2-pyridyl)-methanone, ethylsecodion, ethyl 3-oxo-3-phenyl-propanoate, 3-quinuclidone, ethyl-4-chloro-3-oxo-butanoate; or ketose; or the aldehyde substrate accoding to general formula (I'); or 2-butanal; or 1-heptanal; and differ from the amino acid sequence of the wild type ketoreductase of SEQ ID NO:2 by 1 to 70, preferably by 1 to 50, more preferably by 1 to 30, even more preferably by 1 to 20, and most preferably by 1 to 11 residue changes, preferably including one or more of the following residue changes: Y21Q; V23T; S33A; L39V; R40C; A43E or G; P68S; V89F; G95A, E, M, Q, S or V; P97A, E, K, N, V or Y; T98A or G; D103E; G109Y; V119Y; L121Q; V124I; Y125F; I149A, G, L, M, Q, T or V; L150A, F, H or S; S154G; E155A, D, F, G, K, L or S; T157Y; A158G, L, P, Q, S, V or W; T163A or S; H190C; Y193A, F, G, P, T or V; L198M; L199A, F, I or T; A201G; A206G; Y207R or L; V229I; and V247I.

Preferably, the engineered ketoreductase according to the invention that differs from the wild type ketoreductase of SEQ ID NO:2 comprises an amino acid sequence or essentially consists of an amino acid sequence having one of the following sets of amino acid substitutions compared to SEQ ID NO:2:

| No. | Amino acid exchanges to SEQ ID No: 2 | SEQ ID of mutant |
|---|---|---|
| 1. | V89F | SEQ ID NO: 4 |
| 2. | Y125F | SEQ ID NO: 5 |
| 3. | V229I | SEQ ID NO: 6 |
| 4. | G95Q, L150F, E155S, A158L, L199T | SEQ ID NO: 7 |
| 5. | G95S, L150A, E155S, Y193V, L199A | SEQ ID NO: 8 |
| 6. | G95E, L150H, A158L | SEQ ID NO: 9 |
| 7. | G95Q, P97A, A158Q, L199T | SEQ ID NO: 10 |
| 8. | G95M, P97V, L150F, E155S, A158V, Y193P, L199T | SEQ ID NO: 11 |
| 9. | G95S, P97Y, L150F, E155S, A158Q, L199I | SEQ ID NO: 12 |
| 10. | G95Q, P97K, L150F, E155S, A158L, Y193A, L199T | SEQ ID NO: 13 |
| 11. | G95M, P97K, L150F, E155L, A158S, Y193A, L199A | SEQ ID NO: 14 |
| 12. | G95M, P97Y, L150A, E155A, A158G, Y193A | SEQ ID NO: 15 |
| 13. | R40C, G95M, P97A, A158Q, L199I | SEQ ID NO: 16 |
| 14. | G95M, P97N, L150A, A158L, Y193A | SEQ ID NO: 17 |
| 15. | G95S, L150F, E155F, A158Q, Y193F, L199T | SEQ ID NO: 18 |
| 16. | G95M, P97L, L150A, E155L, A158Q, Y193F, L199A | SEQ ID NO: 19 |
| 17. | G95Q, P97A, L150F, E155S, A158V, Y193V, L199I | SEQ ID NO: 20 |
| 18. | P68S, G95M, P97Y, E155F, A158L, Y193A | SEQ ID NO: 21 |
| 19. | G95M, E155K, A158L, Y193F | SEQ ID NO: 22 |
| 20. | G95M, E155S, A158V, Y193F, L199T | SEQ ID NO: 23 |
| 21. | G95A, P97N, L150A, E155L, A158L, Y193P | SEQ ID NO: 24 |
| 22. | G95Q, P97V, L150S, E155G, A158P, Y193V, L199T | SEQ ID NO: 25 |
| 23. | G95M, L150A, E155F, A158S, Y193A, L199T | SEQ ID NO: 26 |
| 24. | G95S, P97E, L150A, E155L, A158L, Y193V, L199T | SEQ ID NO: 27 |
| 25. | G95S, A158L, Y193V, L199A | SEQ ID NO: 28 |
| 26. | L150F, A158Q, Y193P | SEQ ID NO: 29 |
| 27. | G95S, P97A, L150A, E155L, A158Q, Y193F, L199A | SEQ ID NO: 30 |
| 28. | G95S, A158L, Y193T | SEQ ID NO: 31 |
| 29. | L150F, E155K, A158S, Y193P, L199F | SEQ ID NO: 32 |
| 30. | G95E, L150A, E155S, A158L, Y193V, L199T | SEQ ID NO: 33 |
| 31. | G95M, L150A, A158L, Y193V | SEQ ID NO: 34 |
| 32. | G95A, P97L, L150F, E155A, Y193P | SEQ ID NO: 35 |
| 33. | G95A, Y193A | SEQ ID NO: 36 |
| 34. | G95A, P97V, A158S, Y193A, L199I | SEQ ID NO: 37 |
| 35. | G95V, A158Q, Y193A | SEQ ID NO: 38 |
| 36. | L150F, E155S, A158Q, Y193G | SEQ ID NO: 39 |
| 37. | E155D, A158Q, Y193G | SEQ ID NO: 40 |
| 38. | I149L, L150F, E155S, A158Q, Y193G | SEQ ID NO: 41 |
| 39. | I149M, L150F, E155S, A158Q, Y193G | SEQ ID NO: 42 |
| 40. | I149G, L150F, E155S, A158Q, Y193G | SEQ ID NO: 43 |
| 41. | I149T, L150F, E155S, A158Q, Y193G | SEQ ID NO: 44 |
| 42. | I149Q, L150F, E155S, A158Q, Y193G | SEQ ID NO: 45 |
| 43. | I149A, L150F, E155S, A158Q, Y193G | SEQ ID NO: 46 |
| 44. | I149V, L150F, E155S, A158Q, Y193G | SEQ ID NO: 47 |
| 45. | D103E, L150F, E155S, A158Q, Y193G | SEQ ID NO: 48 |
| 46. | L150F, E155S, A158Q, Y193G, L198M | SEQ ID NO: 49 |
| 47. | L150F, E155S, A158Q, Y193G, A201G | SEQ ID NO: 50 |
| 48. | L150F, E155S, A158Q, Y193G, Y207R | SEQ ID NO: 51 |
| 49. | L150F, E155S, T157Y, A158Q, Y193G | SEQ ID NO: 52 |
| 50. | L39V, L150F, E155S, A158Q, Y193G | SEQ ID NO: 53 |
| 51. | L150F, S154G, E155S, A158Q, Y193G | SEQ ID NO: 54 |
| 52. | L39V, A43G, I149V, L150F, S154G, E155S, A158Q, Y193G, A201G, Y207L | SEQ ID NO: 55 |
| 53. | L39V, I149V, L150F, S154G, E155S, T157Y, A158Q, Y193G, L198M, A201G, Y207R | SEQ ID NO: 56 |
| 54. | L39V, I149V, L150F, S154G, E155S, A158Q, Y193G, A201G, Y207L | SEQ ID NO: 57 |
| 55. | L39V, I149V, L150F, S154G, E155S, A158Q, Y193G, L198M, A201G, Y207R | SEQ ID NO: 58 |
| 56. | L39V, I149V, L150F, S154G, E155S, A158W, Y193G, L198M, A201G, Y207R | SEQ ID NO: 59 |
| 57. | Y193G | SEQ ID NO: 60 |
| 58. | I149V, Y193G | SEQ ID NO: 61 |
| 59. | T98G, I149V, A158Q, Y193G, L198M | SEQ ID NO: 62 |
| 60. | I149A | SEQ ID NO: 63 |
| 61. | I149V, A158Q, Y193G | SEQ ID NO: 64 |
| 62. | I149V, T163A, Y193G | SEQ ID NO: 65 |
| 63. | I149V, T163S, Y193G | SEQ ID NO: 66 |
| 64. | I149V, A158Q, T163A, Y193G | SEQ ID NO: 67 |
| 65. | I149V, A158Q, T163S, Y193G | SEQ ID NO: 68 |
| 66. | I149V, H190C, Y193G | SEQ ID NO: 69 |
| 67. | T98G, I149V, Y193G | SEQ ID NO: 70 |
| 68. | A43G, I149V, Y193G | SEQ ID NO: 71 |
| 69. | I149V, Y193G, L198M | SEQ ID NO: 72 |
| 70. | I149V, L150S, E155L, A158Q, Y193G | SEQ ID NO: 73 |
| 71. | I149V, L150S, E155D, A158S, Y193G | SEQ ID NO: 74 |
| 72. | I149V, E155L, A158Q, Y193G | SEQ ID NO: 75 |

| No. | Amino acid exchanges to SEQ ID No: 2 | SEQ ID of mutant |
|---|---|---|
| 73. | I149V, A158S, Y193G | SEQ ID NO: 76 |
| 74. | I149V, E155A, A158S, Y193G | SEQ ID NO: 77 |
| 75. | I149V, E155D, A158S, Y193G | SEQ ID NO: 78 |
| 76. | V23T, T98G, V119Y, V124I, I149V, A158Q, Y193G, L198M | SEQ ID NO: 79 |
| 77. | T98G, G109Y, L121Q, V124I, I149V, A158Q, Y193G, L198M, A206G | SEQ ID NO: 80 |
| 78. | T98G, G109Y, V124I, I149V, A158Q, Y193G, L198M, A206G, V247I | SEQ ID NO: 81 |
| 79. | V23T, S33A, T98G, G109Y, V124I, I149V, A158Q, Y193G, L198M, A206G, V247I | SEQ ID NO: 82 |
| 80. | V23T, S33A, T98G, V124I, I149V, A158Q, Y193G, L198M, A206G, V247I | SEQ ID NO: 83 |
| 81. | G95M, L150A, A158L, Y193T, L199I | SEQ ID NO: 84 |
| 82. | I149V, L150F, S154G, E155S, A158Q, Y193G, L198M, A201G, Y207R | SEQ ID NO: 85 |
| 83. | L39V, I149V, S154G, E155S, A158Q, Y193G, L198M, A201G, Y207R | SEQ ID NO: 86 |
| 84. | L39V, I149V, L150F, S154G, A158Q, Y193G, L198M, A201G, Y207R | SEQ ID NO: 87 |
| 85. | L39V, I149V, L150F, S154G, E155S, A158Q, Y193G, A201G, Y207R | SEQ ID NO: 88 |
| 86. | L39V, I149V, L150F, S154G, E155S, A158Q, Y193G, L198M, Y207R | SEQ ID NO: 89 |
| 87. | G95A, I149T, Y193G | SEQ ID NO: 90 |
| 88. | A43E, T98A, I149V, A158Q, Y193G, L198M | SEQ ID NO: 91 |
| 89. | V23T, T98G, G109Y, V124I, I149V, A158Q, Y193G, L198M | SEQ ID NO: 92 |
| 90. | Y21Q, T98G, G109Y, V124I, I149V, A158Q, Y193G, L198M, A206G | SEQ ID NO: 93 |

Preferably, the engineered ketoreductases according to the invention are capable of reducing any aldehyde substrate or are capable of stereoselectively reducing any keto substrate, preferably the keto substrate of general formula (I); or the 3-aryl-3-ketopropanamine-derivatives according to general formula (II); or the 5-hydroxy-3-oxo-hexanoate-derivatives according to general formula (III); or the acetophenone-derivatives according to general formula (IV); or the benzoyl-derivatives according to general formula (V); or the secodione-derivatives according to general formula (VI); or 3-quinuclidone; ethyl-3-oxo-3-phenyl-propanoate; or ethyl-4-chloro-3-oxo-butanoate; or ketose; or the aldehyde substrate accoding to general formula (I'); or 2-butanal; or 1-heptanal; and comprise or essentially consist of one of the following amino acid sequences: SEQ ID NO:4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93.

Preferably, the engineered ketoreductases according to the invention are capable of reducing any aldehyde substrate or are capable of stereoselectively reducing any keto substrate, preferably the keto substrate of general formula (I); or the 3-aryl-3-ketopropanamine-derivatives according to general formula (II); or the 5-hydroxy-3-oxo-hexanoate-derivatives according to general formula (III); or the acetophenone-derivatives according to general formula (IV); or the benzoyl-derivatives according to general formula (V); or the secodione-derivatives according to general formula (VI); or 3-quinuclidone; or ethyl-3-oxo-3-phenyl-propanoate; or ethyl-4-chloro-3-oxo-butanoate; or ketose; or the aldehyde substrate accoding to general formula (I'); or 2-butanal; or 1-heptanal; and exhibit an improved specific activity, temperature stability, and/or stereoselectivity compared to the wild type ketoreductase of SEQ ID NO:2, and comprise or essentially consist of one of the following amino acid sequences: SEQ ID NO:4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93.

Preferably, the engineered ketoreductase according to the invention is capable of stereoselectively reducing N,N-dimethyl-3-keto-3-(2-thienyl)-1-ketopropanamine to preferably (1S)-3-(dimethylamino)-1-(2-thienyl)-propan-1-ol and comprises or essentially consists of one of the following amino acid sequences: SEQ ID NO:47, 49, 50, 51, 52, 53, 54, 55, 56, 57, 58, 59, 62, 72, 85, 86, 87, 88, or 89; more preferably SEQ ID NO:55, 58, or 87; most preferably SEQ ID NO:58.

Preferably, the engineered ketoreductase according to the invention is capable of stereoselectively reducing substrate N-monomethyl-3-keto-3-(2-thienyl)-1-ketopropanamine to preferably (1S)-3-(methylamino)-1-(2-thienye-propan-1-ol and comprises or essentially consists of one of the following amino acid sequences: SEQ ID NO:19, 28, 40, 46, 47, 49, 50, 55, 56, 57, 58, 59, 62, 64, 67, 72, 81, 82, 83, 85, 86, 87, 88, 89, 92, or 93; more preferably SEQ ID NO:58, 87, or 92; most preferably SEQ ID NO:87.

Preferably, the engineered ketoreductase according to the invention is capable of stereoselectively reducing tert-butyl (5R)-6-cyano-5-hydroxy-3-oxo-hexanoate to preferably tert-butyl (3R,5R)-6-cyano-3,5-dihydroxy-hexanoate and comprises or essentially consists of one of the following amino acid sequences: SEQ ID NO:34, 36, 40, 49, 55, 60, 61, 62, 64, 65, 66, 67, 68, 69, 70, 71, 72, 73, 74, 75, 76, 77, 78, 81, 82, 83, 84, 91, 92, or 93; more preferably SEQ ID NO:62, 91, or 92; most preferably SEQ ID NO:91.

Preferably, the engineered ketoreductase according to the invention is capable of stereoselectively reducing tert-butyl (5S)-6-chloro-5-hydroxy-3-oxohexanoate to preferably tert-butyl (3R,5S)-6-chloro-3,5-dihydroxy-hexanoate and comprises or essentially consists of one of the following amino acid sequences: SEQ ID NO:34, 36, 40, 49, 53, 54, 55, 60, 61, 62, 64, 65, 66, 67, 68, 70, 72, 73, 74, 75, 76, 77, 78, 81, 82, 83, 92, or 93; more preferably SEQ ID NO:62, 91, or 92; most preferably SEQ ID NO:91.

Preferably, the engineered ketoreductase according to the invention is capable of stereoselectively reducing 1-(4-chlorophenyl)ethanone to 1-(4-chlorophenyl)ethanol and comprises or essentially consists of one of the following amino acid sequences: SEQ ID NO: 7, 9, 12, 15, 17, 18, 23, 24, 28, 31, 36, 38, 39, 47, 48, 49, 50, 51, 52, 53, 54, 55, 58, 62, 72, 81, 82, 83, 87, or 92; more preferably SEQ ID NO:7, 15, or 28; most preferably SEQ ID NO:28.

Preferably, the engineered ketoreductase according to the invention is capable of stereoselectively reducing 1-(2-methoxyphenyl)ethanone to 1-(2-methoxyphenyl)ethanol and comprises or essentially consists of one of the following amino acid sequences: SEQ ID NO:15, 17, 22, 24, 26, 36, 38, 40, 58, 60, 61, 62, 64, 65, 66, 67, 68, 69, 70, 71, 72, 73, 75, 76, 77, 78, 81, 82, 83, 86, 92, or 93; more preferably SEQ ID NO:17, 72, or 92; most preferably SEQ ID NO:72.

Preferably, the engineered ketoreductase according to the invention is capable of stereoselectively reducing phenyl-(2-pyridyl)-methanone to phenyl-(2-pyridyl)-methanol and comprises or essentially consists of one of the following amino acid sequences: SEQ ID NO:21, 24, 28, 36, 38, 39, 40, 44, 46, 47, 48, 49, 50, 51, 52, 53, 54, 55, 56, 57, 58, 59, 60, 61, 62, 64, 65, 66, 67, 68, 69, 70, 71, 72, 73, 74, 75, 76, 77, 78, 81, 82, 83, 85, 86, 87, 88, 89, 92, or 93; more preferably SEQ ID NO:72, 82, or 92; most preferably SEQ ID NO:72.

Preferably, the engineered ketoreductase according to the invention is capable of stereoselectively reducing ethylsecodion (ethyl-3-methoxy-8,14-seco-gona-1,3,5(10),9(11)-tetraen-14,17-dione) to preferably ethylseconol (ethyl-3-methoxy-8,14-seco-gona-1,3,5(10),9(11)-tetraen-14-on-17-β-ol) and comprises or essentially consists of one of the following amino acid sequences: SEQ ID NO:61, 62, 65, 66, 69, 70, 71, 75, 78, 82, 83, 86, 92, or 93; more preferably SEQ ID NO:69, 70, or 71; most preferably SEQ ID NO:70.

Preferably, the engineered ketoreductase according to the invention is capable of stereoselectively reducing ethyl 3-oxo-3-phenyl-propanoate to ethyl 3-hydroxy-3-phenyl-propanoate and comprises or essentially consists of one of the following amino acid sequences: SEQ ID NO: 17, 34, 36, 40, 46, 47, 52, 60, 61, 62, 64, 65, 66, 67, 68, 70, 71, 72, 73, 74, 75, 76, 77, 78, 81, 82, 83, 84, 92, or 93; more preferably SEQ ID NO:46, 76, or 78; most preferably SEQ ID NO:76.

Preferably, the engineered ketoreductase according to the invention is capable of stereoselectively reducing the keto substrate ethyl-4-chloro-3-oxo-butanoate to preferably ethyl (3S)-4-chloro-3-hydroxy-butanoate and comprises or essentially consists of one of the following amino acid sequences: SEQ ID NO:63 or 90.

Preferably, the engineered ketoreductase according to the invention is capable of stereoselectively reducing 3-Quinuclidone (synonymous to 1-azabicyclo[2.2.2]octan-3-one hydrochloride) to 3-Quinuclidinol (synonymous to 1-azabicyclo[2.2.2]octan-3-ol) and comprises or essentially consists of one of the following amino acid sequences: SEQ ID NO:17, 21, 26, 38, 40, 62, 72, 73, 81, 83, 86, 92, or 93; more preferably SEQ ID NO:17, 21, or 73; most preferably SEQ ID NO:17.

Preferably, the engineered ketoreductase according to the invention besides an improved specific activity, temperature stability, and/or stereoselectivity compared to the wild type ketoreductase of SEQ ID NO:2 furthermore exhibits a high cosubstrate activity and/or cosubstrate stability, in particular a high stability and/or activity with isoproyl alcohol, 2-butanol, 2-pentanol, 2-hexanol, or 2-heptanol.

Preferably, the engineered ketoreductase according to the invention exhibits an improved specific activity which is higher than the specific activity of the non-engineered ketoreductase. Preferably, the specific activity is at least 10%, at least 50%, at least 100%, at least 1.5 times, at least 2 times, at least 3 times, at least 5 times, at least 10 times, at least 20 times, at least 50 times, at least 100 times, at least 200 times, at least 300 times, at least 500 times, at least 700 times, at least 1000 times, at least 10.000 times, or at least 100.000 times higher than the specific activity of the non-engineered ketoreductase. The improved specific activity may also mean that the engineered ketoreductase does exhibit a certain activity towards the desired substrate, whereas the non-engineered ketoreductase has no significant activity towards said substrate.

Preferably, the engineered ketoreductase according to the invention exhibits a temperature stability that is higher than the temperature stability of the wild type ketoreductase of SEQ ID NO:2. Preferably, the engineered ketoreductase according to the invention exhibits an improved temperature stability which is elevated by 1° C. to 40° C., preferably 1° C. to 30° C., more preferably 1° C. to 20° C., even more preferably 3° C. to 15° C., and most preferably 15° C. compared to the wild type ketoreductase of SEQ ID NO:2.

Preferably, the engineered ketoreductase according to the invention provides an improved enantiomeric excess that preferably is relatively increased by at least 0.1% ee, at least 0.5% ee, at least 1% ee, at least 2% ee, at least 3% ee, at least 5% ee, at least 7% ee, at least 10% ee, at least 20% ee, at least 30% ee, at least 40% ee, at least 50% ee, at least 60% ee, at least 70% ee, at least 80% ee, at least 90% ee, at least 95% ee, at least 97% ee, at least 98% ee, or at least 99% ee compared to the non-engineered ketoreductase. The improved stereoselectivity may also mean that the engineered ketoreductase does have a certain stereoselectivity towards the desired chiral product, whereas the non-engineered ketoreductase has no significant stereoselectivity towards said chiral product.

Improved specific activity of the engineered ketoreductase compared to the non-engineered ketoreductase of SEQ ID NO:2 is preferably determined under standardized reaction conditions, typically at 30° C. in buffered aqueous solution, containing substrate, cofactor, optional supplements and ketoreductase. The buffer is preferably selected from the group consisting of 10-200 mM Tris/HCl at pH 7-9 containing 2 mM MgCl$_2$, 10-200 mM sodium phosphate/NaOH at pH 6-8, or 10-200 mM triethanoleamine/HCl at pH 7-9. The cofactor NADH is preferably added to a final concentration ranging from 0.05 to 10 mM. The substrate, which is preferably added to a final concentration ranging from 5 mM to 1 M, is preferably selected from the group consisting of ethyl-4-chloro-3-oxo-butanoate, 1-(4-chlorophenyl)ethanone, 1-(2-methoxyphenyl)ethanol, tert-butyl (5R)-6-cyano-5-hydroxy-3-oxo-hexanoate, N,N-dimethyl-3-keto-3-(2-thienyl)-1-ketopropanamine, ethylsecodion (ethyl-3-methoxy-8,14-seco-gona-1,3,5(10),9(11)-tetraen-14,17- dione), tert-butyl (5S)-6-chloro-5-hydroxy-3-oxo-hexanoate, and N-monomethyl-3-keto-3-(2-thienyl)-1-ketopropanamine, phenyl-(2-pyridyl)-methanone, ethyl 3-oxo-3-phenyl-propanoate, 3-quinuclidone, 2-butanal and 1-heptanal. Optional other supplements are preferably selected from the group consisting of 1-5% Triton™ X-100 (v/v), and 0.5 to 10% DMSO (v/v). The ketoreductase is preferably added as crude extract supernatant. The crude extract is obtained by disruption of the expression host containing the ketoreductase and subsequent centrifugation to separate the cell debris and the ketoreductase containing supernatant of the crude extract. The specific activity is preferably determined by measuring product formation, depletion of the reduced cofactor NADH, and/or substrate depletion. In case the specific activity is determined by measuring product formation or substrate depletion, a cofactor regeneration system (isopropanol or GDH/glucose) may be applied in the standard reaction. No cofactor regeneration system is applied, in case the specific activity is determined by measuring depletion of the reduced cofactor NADH. In case a cofactor regeneration system is applied the reduced cofactor NADH can be substituted by the oxidized cofactor NAD⁺, which is reduced by the cofactor regeneration system.

Improved stereoselectivity of the engineered ketoreductase compared to the non-engineered ketoreductase of SEQ ID NO:2 is preferably determined under standardized reaction conditions as described above for the determination of the improved specific activity. A chiral analytic is applied to analyze the product formed in the reaction.

Improved temperature stability of the engineered ketoreductase compared to the non-engineered ketoreductase of SEQ ID NO:2 is preferably determined by incubation of the ketoreductase containing crude extract for 15 minutes at a given temperature (preferably the temperature, at which the non-engineered ketoreductase of SEQ ID NO:2 exhibits a residual activity of 10%) in a PCR cycler. Afterwards the crude extract is incubated on ice for 30 minutes. Insoluble proteins are separated by centrifugation and the supernatant is analyzed regarding its remaining ketoreductase activity in a standard ketoreductase assay. In this standard assay a suitable substrate for the ketoreductase, e.g. isopropyl alcohol is oxidized e.g. to acetone, by the ketoreductase with concomitant reduction of NAD⁺ to NADH (since no other ketoreductase substrate is present in this standard assay, isopropyl alcohol functions as substrate for the ketoreductase and is not applied for cofactor regeneration). The increase of NADH is monitored by measuring the absorption at 340 nm in a standard photometer. The assay is carried out under standardized reaction conditions, i. e. typically at 30° C. in buffered aqueous solution, containing substrate (e.g. isopropyl alcohol), cofactor and ketoreducase. The ketoreductase is preferably added as crude extract supernatant. The crude extract is obtained by disruption of the expression host containing the ketoreductase and subsequent centrifugation to separate the cell debris and the ketoreductase containing supernatant of the crude extract.The buffer is preferably selected from the group consisting of 10-200 mM Tris/HCl at pH 7-9 containing 2 mM MgCl₂, 10-200 mM sodium phosphate/NaOH at pH 6-8, or 10-200 mM triethanoleamine/HCl at pH 7-9. The cofactor NAD⁺ is preferably added to a final concentration ranging from 0.05 to 10 mM. The ketoreductase is preferably added as crude extract supernatant. The crude extract is obtained by disruption of the expression host containing the ketoreductase and subsequent centrifugation to separate the cell debris and the ketoreductase containing supernatant of the crude extract.

In a preferred embodiment the engineered ketoreductase exhibiting an improved thermal stability differs from the amino acid sequence of the wild type ketoreductase of SEQ ID NO:2 by a residue change of at least one of the following positions: V89, Y125, or V229.

In another preferred embodiment the engineered ketoreductase exhibiting an improved thermal stability differs from the amino acid sequence of the wild type ketoreductase of SEQ ID NO:2 by an amino acids substitution in one, two or three positions selected from the positions V89, Y125, or V229, and by at least one further amino acids substitution in a different position.

In a more preferred embodiment the engineered ketoreductase exhibiting an improved thermal stability differs from the amino acid sequence of the wild type ketoreductase of SEQ ID NO:2 by one of the following residue changes: V89F, Y125F, or V229I.

In another preferred embodiment the engineered ketoreductase exhibiting an improved thermal stability differs from the amino acid sequence of the wild type ketoreductase of SEQ ID NO:2 by an amino acids substitution in one, two or three positions selected from the positions V89F, Y125F, or V229I, and by at least one further amino acids substitution in a different position.

In a most preferred embodiment the engineered ketoreductase exhibiting an improved thermal stability differs from the amino acid sequence of the wild type ketoreductase of SEQ ID NO:2 by the residue change V89F.

In another most preferred embodiment the engineered ketoreductase exhibiting an improved thermal stability differs from the amino acid sequence of the wild type ketoreductase of SEQ ID NO:2 by the residue change V89F and by at least one further amino acids substitution in a different position.

In another preferred embodiment the engineered ketoreductase according to the invention differing from the amino acid sequence of the wild type ketoreductase of SEQ ID NO:2 by one, two or three positions selected from the positions V89, Y125, or V229; most preferably by one, two, or three positions selected from the positions V89F, Y125F, or V229I; exhibits a temperature stability which is elevated for 1° C. to 40° C., preferably 1° C. to 30° C., more preferably 1° C. to 20° C., even more preferably 3° C. to 15° C., and most preferably 15° C. compared to the wild type ketoreductase of SEQ ID NO:2.

In another embodiment the engineered ketoreductase according to the invention differing from the amino acid sequence of the wild type ketoreductase of SEQ ID NO:2 by one, two or three positions selected from the positions V89, Y125, or V229, and by at least one further amino acids substitution in a different position; most preferably by one, two, or three positions selected from the positions V89F, Y125F, or V229I, and at least one further amino acids substitution in a different position; exhibits a temperature stability which is elevated for 1° C. to 40° C., preferably 1° C. to 30° C., more preferably 1° C. to 20° C., even more preferably 3° C. to 15° C., and most preferably 15° C. compared to the wild type ketoreductase of SEQ ID NO:2.

Preferably, the ketoreductase according to the invention comprises or essentially consists of an amino acid sequence of at least 85% homology, preferably at least 86% or at least 87%, more preferably at least 88% or at least 89%, still more preferably at least 90% or at least 91%, yet more preferably at least 92% or at least 93%, even more preferably at least 94% or at least 95%, most preferably at least 96% or at least 97%, and in particular at least 98% or at least 99% to the SEQ ID NO: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93.

In a preferred embodiment, the ketoreductase according to the invention is a variant of the polypeptide of SEQ ID NO:2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93 comprising a substitution, deletion and/or insertion of 1 to 36 amino acids, e.g. 1 to 6 amino acids, 7 to 12 amino acids, 13 to 18 amino acids, 19 to 24 amino acids, 25 to 30 amino acids, or 31 to 36 amino acids.

In a preferred embodiment, the ketoreductase according to the invention is a fragment of at least 220 amino acid residues, more preferably at least 225 amino acid resides, still more preferably at least 230 amino acid residues, yet more preferably at least 235 amino acid residues, even more preferably at least 240 amino acid residues, most preferably at least 245 amino acid residues, most preferably at least 250 amino acid residues, most preferably at least 251 amino acids, most preferably at least 252 amino acid residues, and in particular at least 253 amino acid residues of the polypeptide of SEQ ID NO:2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93. In this regard, "fragment" refers to a consecutive subsequence of the respective SEQ ID NO but that is shortened at the N-terminus and/or the C-terminus.

In a preferred embodiment, the ketoreductase according to the invention is a fusion protein of the amino acid sequence of SEQ ID NO:2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93, with any other amino acid, oligo- or polypeptide, which is fused to the N-terminus and/or the C-terminus.

In a preferred embodiment, the ketoreductase according to the invention comprises the amino acid sequence of SEQ ID NO:2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93, and additionally, at least 10 amino acid residues, more preferably at least 20 amino acid residues, even more preferably at least 30 amino acid residues, and most preferably at least 40 amino acid residues, independently selected from the group consisting of Ala, Arg, Asn, Asp, Cys, Gln, Glu, Gly, His, Ile, Leu, Lys, Met, Phe, Pro, Ser, Thr, Trp Tyr, and Val.

In some embodiments the ketoreductase according to the invention is capable of oxidizing aldehyde substrates to carboxylic acids, wherein the aldehyde substrates are preferably selected from the group consisting of aliphatic, aromatic and hetero-aromatic aldehyde substrates.

Another aspect of the invention relates to a method for the stereoselective reduction of a keto substrate to a secondary alcohol comprising the step of reacting the keto substrate and a suitable cofactor in the presence of a ketoreductase according to the invention. Preferably, said suitable cofactor is NADH or NADPH. All preferred embodiments that have been defined above with respect to the ketoreductase according to the invention also apply to the method according to the invention and thus, are not reiterated hereinafter.

Another aspect of the invention relates to a method for reducing aldehydes to primary alcohols comprising the step of reacting the aldehyde and a suitable cofactor in the presence of a ketoreductase according to the invention. Preferably, said suitable cofactor is NADH or NADPH. All preferred embodiments that have been defined above with respect to the ketoreductase according to the invention also apply to the method according to the invention and thus, are not reiterated hereinafter.

Preferably, the method involves to concomitant conversion of a cosubstrate for cofactor regeneration by the respective ketoreductase at a high specific activity, such cosubstrates preferably being selected according their specific activity from the group consisting of isopropyl alcohol, 2-butanol, 2-pentanol, 2-hexanol, and 2-heptanol, and most preferably converting isopropyl alcohol to acetone at a high specific activity. In a preferred embodiment of the method according to the invention, the oxidized cofactor NAD(P)$^+$ is regenerated by use of NADPH:NADH oxidase (NOX), e.g. from *Lactobacillus sanfranciscensis* (Lountos et al., Acta Cryst. (2004), D60, 2044-2047), and a suitable cosubstrate, e.g. isopropyl alcohol.

Another aspect of the invention relates to a method for stereoselective oxidation of secondary alcohols to keto products comprising the step of reacting the secondary alcohol and a suitable cofactor in the presence of a ketoreductase according to the invention. Preferably, said suitable cofactor is NAD$^+$ or NADP$^+$. All preferred embodiments that have been defined above with respect to the ketoreductase according to the invention also apply to the method according to the invention and thus, are not reiterated hereinafter.

Another aspect of the invention relates to a method for oxidizing primary alcohols to aldehydes comprising the step of reacting the primary alcohol and a suitable cofactor in the presence of a ketoreductase according to the invention. Preferably, said suitable cofactor is NAD$^+$ or NADP$^+$. All preferred embodiments that have been defined above with respect to the ketoreductase according to the invention also apply to the method according to the invention and thus, are not reiterated hereinafter.

Preferably, the method involves to concomitant conversion of a cosubstrate for cofactor regeneration by the respective ketoreductase at a high specific activity, such cosubstrates preferably being selected according their specific activity from the group consisting of isopropyl alcohol, 2-butanol, 2-pentanol, 2-hexanol, and 2-heptanol, and most preferably converting isopropyl alcohol to acetone at a high specific activity. In a preferred embodiment of the method according to the invention, the reduced cofactor NAD(P)H is regenerated by use of NADPH:NADH oxidase (NOX), e.g. from *Lactobacillus sanfranciscensis* (Lountos et al., Acta Cryst. (2004), D60, 2044-2047), and a suitable cosubstrate, e.g. acetone.

Preferably, in the method according to the invention for the stereoselective reduction of keto substrates to secondary alcohols, and for the reduction of aldehyde substrates to primary alcohols, respectively, the aldehyde substrate and the keto substrate may be any aldehyde substrate or any keto substrate, preferably the keto substrate of general formula (I) or the aldehyde substrate of general formula (I'); or the 3-aryl-3-ketopropanamine-derivatives according to general formula (II); or the 5-hydroxy-3-oxo-hexanoate-derivatives according to general formula (III); or the acetophenone-derivatives according to general formula (IV); or the benzoyl-derivatives according to general formula (V); or the secodione-derivatives according to general formula (VI); or 3-quinuclidone; or ethyl 3-oxo-3-phenyl-propanoate; or ethyl-4-chloro-3-oxo-butanoate; or ketose; or 2-butanal; or 1-heptanal.

All preferred embodiments that have been defined above with respect to the keto substrates and the aldehyde substrates according to the invention also apply to the method according to the invention and thus, are not reiterated hereinafter.

Another aspect of the invention relates to a method for oxidizing aldehyde substrates to carboxylic acids comprising the step of reacting the aldehyde substrate and a suitable cofactor in the presence of a ketoreductase according to the invention. Preferably, said suitable cofactor is NAD$^+$ or NADP$^+$. All preferred embodiments that have been defined above with respect to the ketoreductase according to the invention also apply to the method according to the invention and thus, are not reiterated hereinafter.

Preferably, the aldehyde substrate is of general formula (VII)

wherein Z is selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged to the CO-moiety through a saturated or unsaturated, unsubstituted or mono- or polysubstituted aliphatic $C_{1-12}$-hydrocarbon residue; and unsubstituted or mono- or polysubstituted heteroaromatic hydrocarbon residues, optionally being bridged to the CO-moiety through a saturated or unsaturated, unsubstituted or mono- or polysubstituted aliphatic $C_{1-12}$-hydrocarbon residue, wherein mono- or polysubstituted means independently substituted with one or more functional groups selected from -halo,
—OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl,
—$SC_{6-10}$-aryl, —S-heteroaryl, —$S(=)_{1-2}$OH, —NO, —$NO_2$, —$N_3$, —$NH_2$, —$NH(C_{1-12}$-alkyl), —$N(C_{1-12}$-alkyl)$_2$, —$NH(C_{6-10}$-aryl), —$N(C_{6-10}$-aryl)$_2$, —NH(heteroaryl), —N(heteroaryl)$_2$, —CN, —CHO, —$CO_2H$, CO—$C_{1-2}$-alkyl, —CO—$C_{6-10}$-aryl and —CO-heteroaryl.

Preferably, the method involves to concomitant conversion of a cosubstrate for cofactor regeneration by the respective ketoreductase at a high specific activity, such cosubstrates preferably being selected according their specific activity from the group consisting of isopropyl alcohol, 2-butanol, 2-pentanol, 2-hexanol, and 2-heptanol, and most preferably converting isopropyl alcohol to acetone at a high specific activity. In a preferred embodiment of the method according to the invention, the reduced cofactor NAD(P)H is regenerated by use of NADPH:NADH oxidase (NOX), e.g. from *Lactobacillus sanfranciscensis* (Lountos et al., Acta Cryst. (2004), D60, 2044-2047), and a suitable cosubstrate, e.g. acetone.

Thus, the present invention also relates to a method for the
preparation of a secondary alcohol involving the preferably stereoselective reduction of a keto substrate to said secondary alcohol;
preparation of a primary alcohol involving the reduction of an aldehyde substrate to said primary alcohol;
preparation of a keto product involving the oxidation of a secondary alcohol substrate to said keto product;
preparation of an aldehyde involving the oxidation of a primary alcohol substrate to said aldehyde; and/or
preparation of a carboxylic acid involving the oxidation of an aldehyde substrate to said carboxylic acid;
wherein the method comprises the step of reacting the substrate and a suitable cofactor in the presence of a ketoreductase according to the invention. For a reduction reaction catalyzed by ketoreductase (reduction of keto substrate to corresponding secondary alcohol, reduction of aldehyde to corresponding primary alcohol) the suitable cofactor is required in its reduced form as electron donor. For an oxidation reaction catalyzed by ketoreductase (oxidation of secondary alcohol to corresponding ketone, oxidation of primary alcohol to corresponding aldehyde, oxidation of aldehyde to corresponding carboxylic acid) the suitable cofactor is required in its oxidized form as electron acceptor.

When the substrate is chiral, the reaction may proceed stereospecifically and thus, may be used e.g. for kinetic racemic resolution.

In setting up processes, e. g. reduction of ketones, in a preparative scale, the method according to the invention can be performed under consideration of specific further reaction conditions, considering one or more of the parameters selected from the following paramters: The preparative scale reduction can either be performed e.g. with isopropanol or with glucose/GDH for cofactor regeneration. The method according to the invention can be performed in an aqueous environment, in a non-aqueous environment, or in a 2-phase system. The method according to the invention can be carried out at pH-values ranging from 4-11, and/or at temperatures between 5° C. and 90° C., and/or at substrate concentrations ranging from 1-800 g/L. The method according to the invention can be performed with free or with immobilized enzyme. The method according to the invention can be performed as batch process or with continuous removal of product. The method according to the invention can be performed with high substrate feed, and/or by binding (e. g. by adsorption) of product to a solid phase in the reaction vessel, and/or with the addition of water miscible solvents and/or under high shear forces Another aspect of the invention relates to a method for increasing the thermo stability of a ketoreductase having an amino acid sequence that is alignable to SEQ ID NO:2 which method involves the engineering of the ketoreductase, preferably of the ketoreductase of SEQ ID NO:2, in at least one amino acid position selected from the group consisting of the positions that correspond to positions V89, Y125, and/or V229 of SEQ ID NO:2. In this regard "alignable" means that a meaningful comparison and alignment of both sequences can be made so that amino acid residues can be identified that correspond to positions V89, Y125, and/or V229 of SEQ ID NO:2. Typically, amino acid sequences belonging to the SDR family (protein family PF00106 in the Protein Families Database (The Pfam protein families database: M. Punta, P. C. Coggill, R. Y. Eberhardt, J. Mistry, J. Tate, C. Boursnell, N. Pang, K. Forslund, G. Ceric, J. Clements, A. Heger, L. Holm, E. L. L. Sonnhammer, S. R. Eddy, A. Bateman, R. D. Finn Nucleic Acids Research (2012) Database Issue 40:D290-D301), version Pfam 27.0) and/or comprising keto reductase activity (reduction of aldehydes and ketones to the corresponding primary and secondary alcohols, respectively and/or oxidation of primary and secondary alcohols to the corresponding aldehydes and ketones, respectively) and/or having a homology to SEQ ID NO:2 of at least 30% can be regarded as being "alignable". Preferably, the method involves the engineering of the ketoreductase in one, two or three amino acid positions selected from the group consisting of the positions corresponding to positions V89, Y125, and/or V229 of SEQ ID NO:2, and by further engineering of such amino acids sequence, i.e. by replacing the respective amino acid residue by any other proteinogenic amino acid residue.

Preferably, the method is for increasing the thermo stability of ketoreductases according to any SEQ ID NO:2, or of any ketoreductase with a homology of at least 72% to the ketoreductase of SEQ ID NO:2, by engineering of the ketoreductase in at least one amino acid position selected from the group consisting of the positions V89, Y125, and/or V229. Preferably, the method involves the engineering of the ketoreductase in one, two or three amino acid positions selected from the group consisting of the positions corresponding to positions V89, Y125, and/or V229, and by further engineering of such amino acids sequence.

Another aspect of the invention relates to a process for the preparation of a product, preferably of a chiral product, comprising
the method for the stereoselective reduction of a keto substrate to a secondary alcohol according to the invention;
the method for reducing aldehydes to primary alcohols according to the invention;
the method for stereoselective oxidation of secondary alcohols to keto products according to the invention;
the method for oxidizing primary alcohols to aldehydes according to the invention; and/or
the method for oxidizing aldehyde substrates to carboxylic acids according to the invention.

All preferred embodiments that have been defined above with respect to the various methods according to the invention including the ketoreductase according to the invention, the keto substrates according to the invention, the secondary alcohol substrates according to the invention, the aldehyde substrates according to the invention, the primay alcohol substrates according to the invention also apply to the process according to the invention and thus, are not reiterated hereinafter.

Another aspect of the invention relates to the use of a ketoreductase according to the invention for the stereoselective reduction of a keto substrate to a secondary alcohol.

Another aspect of the invention relates to the use of a ketoreductase according to the invention for the reduction of an aldehyde to a primary alcohol.

Another aspect of the invention relates to the use of a ketoreductase according to the invention for the oxidation of a secondary alcohol to a keto product.

Another aspect of the invention relates to the use of a ketoreductase according to the invention for the oxidation of a primary alcohol to an aldehyde product.

Another aspect of the invention relates to the use of a ketoreductase according to the invention for the oxidation of an aldehyde to a carboxylic acid.

Preferably, in the use according to the invention for the stereoselective reduction of keto substrates to secondary alcohols, and for the reduction of aldehyde substrates to primary alcohols, respectively, the aldehyde substrate and the keto substrate may be any aldehyde substrate or any keto substrate, preferably the keto substrate of general formula (I); or the 3-aryl-3-ketopropanamine-derivatives according to general formula (II); or the 5-hydroxy-3-oxo-hexanoate-derivatives according to general formula (III); or the acetophenone-derivatives according to general formula (IV); or the benzoyl-derivatives according to general formula (V); or the secodione-derivatives according to general formula (VI); or 3-quinuclidone; or ethyl-4-chloro-3-oxo-butanoate; or 2-butanal; or 1-heptanal.

All preferred embodiments that have been defined above with respect to the keto substrates and the aldehyde substrates according to the invention also apply to the method according to the invention and thus, are not reiterated hereinafter.

The following examples further illustrate the invention but are not to be construed as limiting its scope.

EXAMPLE 1

Detection of the New Ketoreductase Gene Corresponding to SEQ ID NO:1

The gene of the new ketoreductase was detected during a screening for new ketoreductases in a genomic library derived from microbial communities living in deadwood on the top of small-leaved lime tree (*Tilia cordada*). The DNA of microorganisms selectively grown in a 96-well format was isolated, mechanically fragmented to the desired size range and cloned into the two-promoter expression vector system pF2F4 (WO2010/075956 A1). The resulting plasmids were transformed to *E. coli* BL21(DE3)placI(+) cells. Screening of the library was done with cluster screening (WO2005/040376 A2) with cluster sizes of 5,000 to 350,000 clones per plate.

For expression of the genomic library cells were cultivated in ZYM505 medium (F. William Studier, Protein Expression and Purification 41 (2005) 207-234) supplemented with kanamycin (50 mg/l) and chloramphenicol (34 mg/l)). Expression of the genes of the genomic library was induced at logarithmic phase either by IPTG (0.1 mM) or arabinose (0.1 (v/v)). Cultivations were carried out at 30° C. for 16 hours.

Cells were harvested by centrifugation (3220× g, 20 min, 4° C.) and disrupted with cell lysis buffer (50 mM Tris-HCl pH 7.0; 2 mM $MgCl_2$, 1× CelLytic B (Sigma); DNA nuclease 0.02 U, lysozyme 0.5 mg/ml). The crude extracts were separated from cell debris by centrifugation (3220× g 30 min, 4° C.).

The crude extracts of the genomic library were investigated regarding their ability to reduce the mixture of substrates: ethyl-4-chloro-3-oxo-butanoate and 1-(4-chlorophenyl)ethanone by measuring a decrease in absorbance at 340 nm resulting from the oxidation of NAD(P)H.

EXAMPLE 2

Expression of the New Ketoreductase Gene Corresponding to SEQ ID NO:1

The gene of the newly found ketoreductase corresponding to SEQ ID NO:1 was cloned into the expression vector pLE1A23 (derivative of pRSF-1b, Novagen). The gene was moreover codon optimized for *E. coli* expression while simultaneously decreasing the GC-content (see SEQ ID NO:2). The gene was cloned into the expression vector pLE1A27 (derivative of pRSF-1b, Novagen). The resulting plasmid was used for transformation of *E. coli* BL21(DE3) cells.

For expression of the new ketoreductase gene corresponding to SEQ ID NO:1 cells were cultivated in ZYM505 medium (F. William Studier, Protein Expression and Purification 41 (2005) 207-234) supplemented with kanamycin (50 mg/l) at 37° C. Expression of the gene was induced at logarithmic phase by IPTG (0.1 mM) and carried out at 30° C. for 16-18 hours.

Cells were harvested by centrifugation (3220× g, 20 min, 4° C.) and disrupted with cell lysis buffer (50 mM Tris-HCl pH 7.0; 2 mM $MgCl_2$, 1× CelLytic B (Sigma); DNA nuclease 0.02 U, lysozyme 0.5 mg/ml). The crude extracts were separated from cell debris by centrifugation (3220× g 30 min, 4° C.).

The crude extract was investigated regarding the level of ketoreductase expression via denaturing SDS-PAGE and its ability to reduce ethyl-4-chloro-3-oxo-butanoate by measuring a decrease in absorbance at 340 nm resulting from the oxidation of NAD(P)H.

EXAMPLE 3

Preparative Scale Reduction of Ethyl-4-chloro-3-oxo-butanoate to Ethyl (3S)-4-chloro-3-hydroxy-butanoate by the New Ketoreductase of SEQ ID NO:2

24.08 g D(+)-Glucose monohydrate was dissolved in 0.1 M sodium phosphate buffer pH 6.5 to a final volume of 45 ml in a 250 ml round bottom flask equipped with a magnetic stirrer. The pH of the solution was adjusted to pH 6.5-6.6 with NaOH. 10.7 mg of the new ketoreductase of SEQ ID NO:2, 22.9 mg glucose dehydrogenase (GDH-03, commercially available at c-LEcta GmbH) and 39.8 mg NAD$^+$, each dissolved in 5 ml 0.1 M sodium phosphate buffer pH 6.5 were added. The flask was connected to a pH Stat titration device and tempered to 35° C. while stirring. The reaction was started by a stepwise controlled addition of a solution of 18.18 g ethyl-4-chloro-3-oxo-butanoate in 9.375 ml n-butyl acetate. During the complete reaction time the mixture was stirred and tempered to 35° C. The pH was automatically controlled by NaOH addition by the pH-stat device (setpoint: pH=6.5). Reaction progress is controlled by tracking the amount of 5 M NaOH that was titrated automatically by pH Stat. After 22 hours the reaction is completed resulting in an overall conversion of ≥99.9% analyzed by GC analytics. The reduction product was shown to have an enantiomeric excess of ≥99 for the ethyl (3S)-4-chloro-3-hydroxy-butanoate.

EXAMPLE 4

Evaluation of Ketoreductase Variants Regarding their Thermal Stability

Several ketoreductase variants that had been generated were analyzed regarding their thermal stability. Melting profiles were recorded by incubation of the ketoreductase containing crude extract for 15 minutes at different temperatures in a PCR cycler. Afterwards the crude extracts were incubated on ice for 30 minutes. Insoluble proteins were separated by centrifugation and the supernatants were analyzed regarding their remaining ketoreductase activity in a standard ketoreductase assay. In this standard assay isopropyl alcohol is oxidized to acetone by the ketoreductase with concomitant reduction of NAD$^+$ to NADH. The increase of ketoreductase is monitored by measuring the absorption at 340 nm in a standard photometer.

It was found, that the ketoreductase corresponding to SEQ ID NO:4 exhibits a melting temperature (Tm), that is 15° C. higher than the Tm of the wild type ketoreductase of SEQ ID NO:2

EXAMPLE 5

Reduction of Tert-butyl (5R)-6-cyano-5-hydroxy-3-oxo-hexanoate by Engineered Ketoreductases Derived from Ketoreductase of SEQ ID NO:2

Numerous engineered ketoreductases that had been generated were analyzed regarding their capacity to reduce the substrate tert-butyl (5R)-6-cyano-5-hydroxy-3-oxo-hexanoate to tert-butyl (5R)-6-cyano-3,5-dihydroxy-hexanoate. Screening assays were performed in a 96-well plate scale with a final volume of 150 µl per well in 0.1 M sodium phosphate buffer pH 6.5 and a final concentration of 0.1 M purified tert-butyl (5R)-6-cyano-5-hydroxy-3-oxo-hexanoate and 1 mM cofactor NAD$^+$. Reactions were started by adding 10 µl of a 1 to 300 dilution of crude extract in 0.05 M Tris-HCl buffer pH 7.0, 2 mM MgCl$_2$ to each well. Activities of the ketoreductase variants were determined by measuring the decrease of absorbance at 340 nm in a microplate reader at 30° C. It was found that the ketoreductase variant corresponding to SEQ ID NO:91 reduced the substrate tert-butyl (5R)-6-cyano-5-hydroxy-3-oxo-hexanoate at a 55 fold higher rate than ketoreductase of SEQ ID NO:2.

EXAMPLE 6

Preparative Scale Reduction of Tert-butyl (5R)-6-cyano-5-hydroxy-3-oxo-hexanoate by Engineered Ketoreductase Derived from Ketoreductase of SEQ ID NO:2

4.3 g of a crude batch of tert-butyl (5R)-6-cyano-5-hydroxy-3-oxo-hexanoate (purity ~70%) was weighed in a glass beaker (corresponds to 3 g of pure tert-butyl (5R)-6-cyano-5-hydroxy-3-oxo-hexanoate). A solution of 3.7 g D(+)-Glucose monohydrate in water (final volume 6.8 ml), 1.5 ml of 1 M sodium phosphate buffer pH 6.5 and 10 mg of NAD$^+$ dissolved in water were added. The pH of the solution was adjusted to 6.5-6.6 with NaOH. The reaction mixture was connected to a pH Stat titration device and tempered to 30° C. while stirring. The reaction was started by addition of a solution of the engineered ketoreductase corresponding to SEQ ID NO:91 (21 mg) and glucose dehydrogenase (GDH-03, 10 mg) in water. During the complete reaction time the mixture was stirred and tempered to 30° C. The pH was automatically controlled by NaOH addition by the pH-stat device (setpoint: pH=6.5). Reaction progress was controlled by tracking the amount of 5 M NaOH that was titrated automatically by pH Stat. After 12 hours reaction is finished resulting in an overall conversion of ≥95% analyzed by HPLC analytics (detection at 212 nm and 200 nm, quantification by calibration curves of substrate and product). The reduction product was shown to have a diastereomeric excess of ≥99 for the syn product (tert-butyl (3R,5R)-6-cyano-3,5-dihydroxy-hexanoate) over the corresponding anti product (tert-butyl (3S,5R)-6-cyano-3,5-dihydroxy-hexanoate) as measured by chiral HPLC.

EXAMPLE 7

Reduction of N,N-dimethyl-3-keto-3-(2-thienyl)-1-ketopropanamine by Engineered Ketoreductases Derived from ADH97

Numerous engineered ketoreductases that had been generated were analyzed regarding their capacity to reduce the substrate N,N-dimethyl-3-keto-3-(2-thienyl)-1-ketopropanamine to N,N-dimethyl-3-hydroxy-3-(2-thienyl)-1-propanamine. Screening assays were performed in a 96-well plate scale with a final volume of 300 µl per well in 0.1 M Triethanolamine/HCl buffer pH 9.0; 50 isopropanol (v/v) and a final concentration of 0.5 M N,N-dimethyl-3-keto-3-(2-thienyl)-1-ketopropanamine and 1 mM cofactor NAD$^+$. Reactions were started by adding 10 µl of a 1 to 10 dilution of crude extract in 0.1 M Triethanolamine-HCl buffer per well. Reactions were incubated at 30° C. for 20 h. Activities of the ketoreductase variants were determined by HPLC analysis (detection at 230 nm/245 nm; determination of conversion by calibration curves of substrates and product) of substrate and product. It was found that the ketoreductase variant corresponding to SEQ ID NO:58 was able to reduce the substrate N,N-dimethyl-3-keto-3-(2-thienyl)-1-ketopropanamine. After 20 hours of reaction a conversion of 23% was achieved. Ketoreductase of SEQ ID NO:2 showed no conversion under the given conditions.

EXAMPLE 8

Preparative Scale Reduction of N,N-dimethyl-3-keto-3-(2-thienyl)-1-ketopropanamine by Engineered Ketoreductase Derived from Ketoreductase of SEQ ID NO:2

A solution of 25% NaOH (110 ml), isopropanol (41.5 ml) and N,N-dimethyl-3-keto-3-(2-thienyl)-1-ketopropanamine hydrochloride (60 g) were added to a 500 ml round bottom flask equipped with a magnetic stirrer. The resulting slurry was stirred at room temperature until complete dissolution and phase separation occurred. Water (40 ml) was added to 27.3 ml of the upper layer in a glass beaker. The pH of the solution was adjusted to 9.0 by addition of concentrated sulfuric acid. 37.5 ml isopropanol was added to the mixture, which was subsequently mixed with 66.5 mg of $NAD^+$ in a 250 ml round bottom flask. The flasks neck was connected to a rotary evaporator and the solution was tempered to 40° C. by rotating the flask in a preheated (40° C.) oil bath. A solution of the engineered ketoreductase corresponding to SEQ ID NO:58 (1.35 g) dissolved in 22.5 ml water was added to start the reaction. During the complete reaction time the flask was rotated and tempered to 40° C. in an oil bath and vacuum (110 mbar, 82.5 mm Hg) was applied to remove mainly acetone and isopropanol. A preheated (40° C.) mixture of isopropanol and water (80:20) was added periodically every half hour to the reaction mixture. Samples were taken every hour for control of the reaction progress and analyzed by HPLC (detection at 230 nm/245 nm; determination of conversion by calibration curves of substrates and product). After 8 hours the reaction is completed resulting in an overall conversion of ≥98%. The reduction product was shown to have an enantiomeric excess of ≥99.5 in favor of the enantiomer (1S)-3-(dimethylamino)-1-(2-thienyl)-propan-1-ol.

EXAMPLE 9

Reduction of ethylsecodion (ethyl-3-methoxy-8,14-seco-gona-1,3,5(10),9(11)-tetraen-14,17-dione) by Engineered Ketoreductases Derived from Ketoreductase of SEQ ID NO:2

Numerous engineered ketoreductases that had been generated were analyzed regarding their capacity to reduce the substrate ethylsecodion (ethyl-3-methoxy-8,14-seco-gona-1,3,5(10),9(11)-tetraen-14,17-dione). Screening assays were performed in a 96-well plate scale with a final volume of 500 μl per well in 0.1 M Triethanolamine/HCl buffer pH 7.0; 2 mM $MgCl_2$, 50% isopropanol (v/v), 1% Triton™ X-100 (v/v), 3% DMSO (v/v) and a final concentration of 10 g/l ethylsecodion (ethyl-3-methoxy-8,14-seco-gona-1,3,5(10),9(11)-tetraen-14,17-dione) and 1 mM cofactor $NAD^+$. Reactions were started by adding 100 μl of a 1 to 10 dilution of crude extract per well. Reactions were incubated at 30° C. for 4 h while stirring. Activities of the ketoreductase variants were determined by HPLC analysis (detection at 265 nm; determination of conversion by calibration curves of substrate and product). It was found that the ketoreductase variant corresponding to SEQ ID NO:70 was able to reduce the substrate ethylsecodion (ethyl-3-methoxy-8,14-seco-gona-1,3,5(10),9(11)-tetraen-14,17-dione) with a conversion of 94% and a stereomeric excess for the 17-β-Seconol (ethyl-3-methoxy-8,14-seco-gona-1,3,5(10),9(11)-tetraen-14-on-17-β-ol) of ≥99.5% under given conditions. Ketoreductase of SEQ ID NO:2 showed no conversion under the given conditions.

The engineered ketoreductase corresponding to SEQ ID NO:70 may also be used for preparative scale reduction of ethylsecodion (ethyl-3-methoxy-8,14-seco-gona-1,3,5(10),9 (11)-tetraen-14,17-dione) under similar conditions as described in this example, wherein a substrate feed is applied.

EXAMPLE 10

Reduction of Tert-butyl (5S)-6-chloro-5-hydroxy-3-oxohexanoate by Engineered Ketoreductases Derived from Ketoreductase of SEQ ID NO:2

Numerous engineered ketoreductases that had been generated were analyzed regarding their capacity to reduce the substrate (5S)-6-chloro-5-hydroxy-3-oxohexanoate to tert-butyl (5S)-6-chloro-3,5-dihydroxy-hexanoate. Screening assays were performed in a 96-well plate scale with a final volume of 150 μl per well in 0.1 M sodium phosphate buffer pH 6.5 and a final concentration of 25 mM purified tert-butyl (5S)-6-chloro-5-hydroxy-3-oxohexanoate and 1 mM cofactor $NAD^+$. Reactions were started by adding 10 μl of several dilutions of crude extract in 0.05 M Tris-HCl buffer pH 7.0, 2 mM $MgCl_2$ to each well. Activities of the ketoreductase variants were determined by measuring the decrease of absorbance at 340 nm in a microplate reader at 30° C. It was found that ketoreductase variants corresponding to SEQ ID NO:62 and 91 reduced the substrate (5S)-6-chloro-5-hydroxy-3-oxohexanoate at a 3 fold higher rate than ketoreductase of SEQ ID NO:2.

The engineered ketoreductases corresponding to SEQ ID NO:62 and 91 may also be used for preparative scale reduction of (5S)-6-chloro-5-hydroxy-3-oxohexanoate to tert-butyl (3R,5S)-6-chloro-3,5-dihydroxy-hexanoate under conditions comparable to the conditions described in example 6.

EXAMPLE 11

Reduction of N-monomethyl-3-keto-3-(2-thienyl)-1-ketopropanamine by Engineered Ketoreductases Derived from Ketoreductase of SEQ ID NO:2

Numerous engineered ketoreductases that had been generated were analyzed regarding their capacity to reduce the substrate N-monomethyl-3-keto-3-(2-thienyl)-1-ketopropanamine to N-monomethyl-3-hydroxy-3-(2-thienyl)-1-propanamine. Screening assays were performed in a 96-well plate scale with a final volume of 200 μl per well in 0.1 M Triethanolamine/HCl buffer pH 7.0; 10 isopropanol (v/v) and a final concentration of 0.1 M N-monomethyl-3-keto-3-(2-thienyl)-1-ketopropanamine and 1 mM cofactor $NAD^+$. Reactions were started by adding 10 μl crude extract per well. Reactions were incubated at 30° C. for 4 h and 24 h. Activities of the ketoreductase variants were determined by HPLC analysis (detection at 230 nm/245 nm; determination of conversion by calibration curves of substrates and product) of substrate and product. It was found that the ketoreductase variants corresponding to SEQ ID NO:58 and SEQ ID NO:87 were able to reduce the substrate N-monomethyl-3-keto-3-(2-thienyl)-1-ketopropanamine best. After 4 hours and 24 hours of reaction conversions of 40-43% and 87-89%, respectively were achieved. Ketoreductase of SEQ ID NO:2 showed no conversion under the given conditions.

The engineered ketoreductases corresponding to SEQ ID NO:58 and 87 may also be used for preparative scale reduction of N-monomethyl-3-keto-3-(2-thienyl)-1-ketopropanamine to (1S)-3-(methylamino)-1-(2-thienyl)-propan-1-ol under conditions comparable to the conditions described in example 6 or example 8.

The invention claimed is:

1. A method for reduction and/or oxidation of substrates comprising:
providing a keto substrate, an aldehylde substrate, a primary or a secondary alcohol substrate;
further providing a ketoreductase comprising an amino acid sequence with at least 84% sequence identity to SEQ ID NO:2 and a cofactor, and, in presence of the ketoreductase and the cofactor
reducing the keto substrate to a secondary alcohol;
reducing the aldehyde substrate to a primary alcohol;

oxidizing the secondary alcohol substrate to a keto product;
oxidizing the primary alcohol substrate to an aldehyde; and/or
oxidizing the aldehyde substrate to a carboxylic acid.

2. The method according to claim 1,
wherein the keto substrate is a keto substrate of general formula (I)

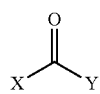
(I)

and the keto substrate is reduced to a secondary alcohol; or
wherein the aldehyde substrate is an aldehyde substrate of general formula (I')

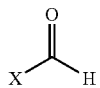
(I')

and the aldehyde substrate is reduced to a primary alcohol;
wherein X and Y are each independently selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged to the CO-moiety through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged to the CO-moiety through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;
wherein mono- or polysubstituted means independently substituted with one or more functional groups selected from
halo, —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —$S(=O)_{1-2}OH$, —NO, —$NO_2$, —$N_3$, —$NH_2$, —NH($C_{1-12}$-alkyl), —N($C_{1-12}$-alkyl)$_2$, NH($C_{6-10}$-aryl), —N($C_{6-10}$-aryl)$_2$, —NH(heteroaryl), —N(heteroaryl)$_2$, —CN, —CHO, —$CO_2H$, CO—$C_{1-2}$-alkyl, —CO—$C_{6-10}$-aryl and —CO-heteroaryl.

3. The method according to claim 2, wherein the keto substrate is selected from the group consisting of
(i) 3-aryl-3-ketopropanamine-derivatives according to general formula (II)

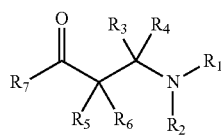
(II)

wherein
$R_1$ and $R_2$ are each independently selected from the group consisting of —H; unsubstituted or mono- or polysubstituted —$C_{1-12}$-alkyl; unsubstituted or mono- or polysubstituted —$C_{3-8}$-cycloalkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; or unsubstituted or mono- or polysubstituted heteroaryl, optionally being bridged through a saturated or unsaturated, unsubstituted or mono- or polysubstituted aliphatic $C_{1-12}$-hydrocarbon residue; or alternatively, wherein
$R_1$ and $R_2$ together with the nitrogen atom to which they are attached form an unsubstituted or mono- or polysubstituted $C_{2-8}$-heterocycloalkyl ring or an unsubstituted or mono- or polysubstituted heteroaryl ring;
$R_3$, $R_4$, $R_5$, and $R_6$ are each independently selected from —H; unsubstituted or mono- or polysubstituted —$C_{1-12}$-alkyl; or wherein $R_3$ and $R_4$ together are =O;
$R_7$ is unsubstituted or mono- or polysubstituted —$C_{6-10}$-aryl; or unsubstituted or mono- or polysubstituted -heteroaryl;
(ii) 5-hydroxy-3-oxo-hexanoate-derivatives according to general formula (III)

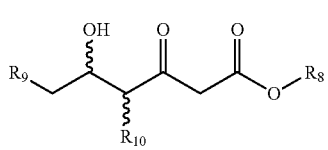
(III)

wherein
$R_8$ is unsubstituted or mono- or polysubstituted —$C_{1-12}$-alkyl; or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue;
$R_9$ is —H; -halo; —CN; or —$OR_{11}$, wherein $R_{11}$ is hydrogen or a protecting group;
$R_{10}$ is —H; unsubstituted or mono- or polysubstituted —$C_{1-12}$-alkyl; or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue;
(iii) acetophenone-derivatives according to general formula (IV)

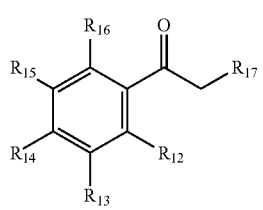
(IV)

wherein

R$_{12}$, R$_{13}$, R$_{14}$, R$_{15}$, and R$_{16}$ are each independently selected from the group consisting of —H; -halo; unsubstituted or mono- or polysubstituted —C$_{1-12}$-alkyl; unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue; unsubstituted or mono- or polysubstituted -heteroaryl, optionally being bridged through a saturated or unsaturated, unsubstituted or mono- or polysubstituted aliphatic C$_{1-12}$-hydrocarbon residue; and OR$_{18}$, wherein R$_{18}$ is —H, unsubstituted or mono- or polysubstituted —C$_{1-12}$-alkyl, or unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue;

R$_{17}$ is —H; -halo; unsubstituted or mono- or polysubstituted —C$_{1-12}$-alkyl; unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue; unsubstituted or mono- or polysubstituted—heteroaryl, optionally being bridged through a saturated or unsaturated, unsubstituted or mono- or polysubstituted aliphatic C$_{1-12}$-hydrocarbon residue; —OR$_{19}$, —NH$_2$, —NHR$_{19}$, or —NR$_{19}$R$_{20}$, wherein R$_{19}$ and R$_{20}$ are each independently selected from unsubstituted or mono- or polysubstituted —C$_{1-12}$-alkyl; unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue; or unsubstituted or mono- or polysubstituted -heteroaryl, optionally being bridged through a saturated or unsaturated, unsubstituted or mono- or polysubstituted aliphatic C$_{1-12}$-hydrocarbon residue;

(iv) benzoyl-derivatives according to general formula (V)

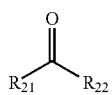

(V)

wherein

R$_{21}$ and R$_{22}$ are each independently selected from unsubstituted or mono- or polysubstituted C$_{6-10}$-aryl and unsubstituted or mono- or polysubstituted heteroaryl;

(v) secodione-derivatives according to general formula (VI)

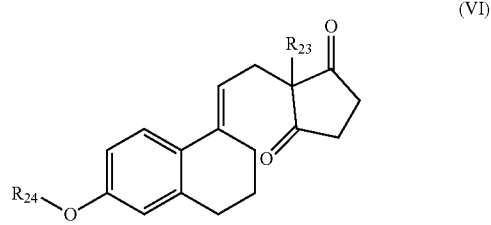

(VI)

wherein

R$_{23}$ and R$_{24}$ are each independently selected from the group consisting of —H and —C$_{1-12}$-alkyl; and (vi) 3-quinuclidone;
(vii) ethyl-4-chloro-3-oxo-butanoate; and
(viii) ethyl-3-oxo-3-phenyl-propanoate;
(ix) ketose;
or wherein the aldehyde substrate is selected from the group consisting of
(x) 2-butanal; and
(xi) 1-heptanal;
wherein in each case mono- or polysubstituted means independently substituted with one or more functional groups selected from -halo, =O, —OH, —OC$_{1-12}$-alkyl, —OC$_{6-10}$-aryl, —O-heteroaryl, —OCOC$_{1-12}$-alkyl, —OCOC$_{6-10}$-aryl, —OCO-heteroaryl, —SH, —SC$_{1-12}$-alkyl, —SC$_{6-10}$-aryl, —S-heteroaryl, —S(=O)$_{1-2}$OH, —NO, —NO$_2$, —N$_3$, —NH$_2$, —NH(C$_{1-12}$-alkyl), N(C$_{1-12}$-alkyl)$_2$, —NH(C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO— heteroaryl.

4. The method according to claim 1 wherein the ketoreductase
(i) converts isopropyl alcohol to acetone at a rate of 0.01-100 U/mg lyophilisate of the ketoreductase; and/or
(ii) after incubation for 48 h in 50% of aqueous isopropyl alcohol at 30° C. exhibits a residual activity of at least 1%, relative to its activity before incubation.

5. The method according to claim 1, wherein the ketoreductase is not identical with the peptide of SEQ ID NO:2 and which exhibits improved specific activity, temperature stability, and/or stereoselectivity compared to the peptide of SEQ ID NO:2.

6. The method according to claim 5 wherein SEQ ID NO: 2 is engineered in at least one or more positions selected from the group consisting of positions

| | | |
|---|---|---|
| Y21Q; | D103E; | T163A or S; |
| V23T; | G109Y; | H190C; |
| S33A; | V119Y; | Y193A, F, G, P, T or V; |
| L39V; | L121Q; | L198M; |
| R40C; | V124I; | L199A, F, I or T; |
| A43E or G; | Y125F; | A201G; |
| P68S; | I149A, G, L, M, Q, T or V; | A206G; |
| V89F; | L150A, F, H or S; | Y207R or L; |
| G95A, E, M, Q, S or V; | S154G; E155A, D, F, G, K, L or S; | V229I; and |
| P97A, E, K, N, V or Y; | T157Y; | V247I. |
| T98A or G; | A158G, L, P, Q, S, V or W; | |

7. The method according to claim 5
(i) wherein the specific activity of the ketoreductase is higher than the specific activity of the wild type ketoreductase of SEQ ID NO:2; and/or
(ii) wherein the temperature stability of the ketoreductase is higher than the temperature stability of the wild type ketoreductase of SEQ ID NO:2; and/or
(iii) wherein the stereoselectivity of the ketoreductase is higher than the stereoselectivity of the wild type ketoreductase of SEQ ID NO:2.

8. The method according to claim 1, which comprises an amino acid sequence of at least 85% homology to the SEQ ID NO:4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, or 93.

9. The method according to claim 1, wherein the substrate is:
(i) ethyl-4-chloro-3-oxo-butanoate which is reduced to ethyl (3S)-4-chloro-3-hydroxy-butanoate; or
(ii) 3-quinuclidone (1-azabicyclo[2.2.2]octan-3-one hydrochloride) which is reduced to 3-Quinuclidinol (synonymous to 1-azabicyclo[2.2.2]octan-3-ol); or
(iii) 1-(2-methoxyphenyl)ethanone, which is reduced to 1-(2-methoxyphenyl)ethanol.

10. The method according to claim 1, wherein
(i) the substrate is ethyl-4-chloro-3-oxo-butanoate which is stereoselectively reduced to ethyl (3S)-4-chloro-3-hydroxy-butanoate with a ketoreductase comprising the amino acid sequence of SEQ ID NO:2;
(ii) the substrate is tert-butyl (5R)-6-cyano-5-hydroxy-3-oxo-hexanoate which is stereoselectively reduced to tert-butyl (3R,5R)-6-cyano-3,5-dihydroxy-hexanoate with a ketoreductase comprising the amino acid sequence of SEQ ID NO:91;
(iii) the substrate is N,N-dimethyl-3-keto-3-(2-thienyl)-1-ketopropanamine which is stereoselectively reduced to (1 S)-3-(dimethylamino)-1-(2-thienyl)-propan-1-ol with a ketoreductase comprising the amino acid sequence of SEQ ID NO:58;
(iv) the substrate is tert-butyl (5S)-6-chloro-5-hydroxy-3-oxohexanoate which is stereoselectively reduced to tert-butyl (3R,5S)-6-chloro-3,5-dihydroxy-hexanoate with a ketoreductase comprising the amino acid sequence of SEQ ID NO:62 or 91;
(v) the substrate is ethylsecodion (ethyl-3-methoxy-8,14-seco-gona 1,3,5(10),9(11)-tetraen-14,17-dione) which is stereoselectively reduced to 17-β-Seconol (ethyl-3-methoxy-8,14-seco-gona-1,3,5(10),9(11)-tetraen-14-on-17-β-ol) with a ketoreductase comprising the amino acid sequence of SEQ ID NO:70; or
(vi) the substrate is N-monomethyl-3-keto-3-(2-thienyl)-1-ketopropanamine which is stereoselectively reduced to (1 S)-3-(methylamino)-1-(2-thienyl)-propan-1-ol with a ketoreductase comprising the amino acid sequence of SEQ ID NO: 58 or 87.

11. The method of claim 1, wherein the ketoreductase comprises the SEQ ID NO: 2.

12. The method of claim 11, wherein the ketoreductase consists essentially of the SEQ ID NO: 2.

13. The method of claim 3, wherein the ketoreductase consists of the SEQ ID NO: 2.

14. A method of comprising:
providing the ketoreductase comprising the SEQ ID NO:2;
providing a keto substrate of general formula (I)

and stereoselectively reducing the keto substrate of general formula (I) with the ketoreductase to a secondary alcohol or
providing a aldehyde substrate of general formula (I')

and reducing the aldehyde substrate of general formula (I') with the ketoreductase to a primary alcohol;
wherein X and Y are each independently selected from saturated or unsaturated, unsubstituted or mono- or polysubstituted aliphatic or alicyclic $C_{1-12}$-hydrocarbon residues; unsubstituted or mono- or polysubstituted $C_{6-10}$-aromatic hydrocarbon residues, optionally being bridged to the CO-moiety through a saturated or unsaturated, unsubstituted or mono- or polysubstituted aliphatic $C_{1-12}$-hydrocarbon residue; unsubstituted or mono- or polysubstituted heteroaromatic hydrocarbon residues, optionally being bridged to the CO-moiety through a saturated or unsaturated, unsubstituted or mono- or polysubstituted aliphatic $C_{1-12}$-hydrocarbon residue; and sugar residues or desoxysugar residues in each case comprising mono-, di- or oligosaccharides;
wherein mono- or polysubstituted means independently substituted with one or more functional groups selected from -halo, —OH, =O, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —S(=O)$_{1-2}$OH, —NO, —$NO_2$, —$N_3$, —$NH_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —$CO_2$H, CO—$C_{1-2}$-alkyl, —CO—$C_{6-10}$-aryl and —CO— heteroaryl.

15. The method of claim 14, wherein the keto substrate is selected from the group consisting of
(i) 3-aryl-3-ketopropanamine-derivatives according to general formula (II)

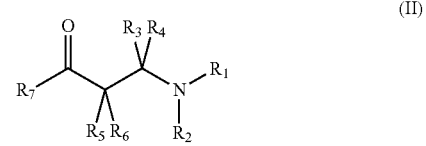

wherein
$R_1$ and $R_2$ are each independently selected from the group consisting of —H; unsubstituted or mono- or polysubstituted —$C_{1-12}$-alkyl; unsubstituted or mono- or polysubstituted —$C_{3-8}$-cycloalkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; or unsubstituted or mono- or polysubstituted heteroaryl, optionally being bridged through a saturated or unsaturated, unsubstituted or mono- or polysubstituted aliphatic $C_{1-12}$-hydrocarbon residue; or alternatively, wherein $R_1$ and $R_2$ together with the nitrogen atom to which they are attached form an unsubstituted or mono- or polysubstituted $C_{2-8}$-heterocycloalkyl ring or an unsubstituted or mono- or polysubstituted heteroaryl ring;

$R_3$, $R_4$, $R_5$, and $R_6$ are each independently selected from —H; unsubstituted or mono- or polysubstituted —$C_{1-12}$-alkyl; or wherein $R_3$ and $R_4$ together are =O;

$R_7$ is unsubstituted or mono- or polysubstituted —$C_{6-10}$-aryl; or unsubstituted or mono- or polysubstituted -heteroaryl;

(ii) 5-hydroxy-3-oxo-hexanoate-derivatives according to general formula (III)

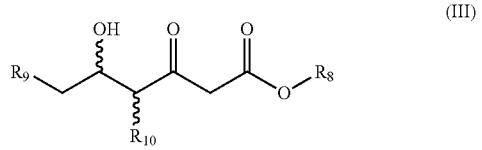

(III)

wherein $R_8$ is unsubstituted or mono- or polysubstituted —$C_{1-12}$-alkyl; or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue;

$R_9$ is —H; -halo; —CN; or —$OR_{11}$, wherein $R_{11}$ is hydrogen or a protecting group;

$R_{10}$ is —H; unsubstituted or mono- or polysubstituted —$C_{1-12}$-alkyl; or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue;

(iii) acetophenone-derivatives according to general formula (IV)

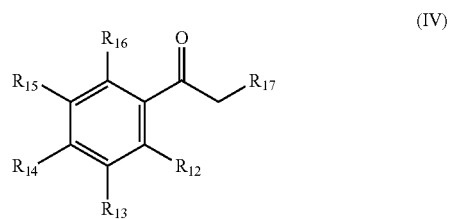

(IV)

wherein $R_{12}$, $R_{13}$, $R_{14}$, $R_{15}$, and $R_{16}$ are each independently selected from the group consisting of —H; -halo; unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; unsubstituted or mono- or polysubstituted -heteroaryl, optionally being bridged through a saturated or unsaturated, unsubstituted or mono- or polysubstituted aliphatic $C_{1-12}$-hydrocarbon residue; and —$OR_{18}$, wherein $R_{18}$ is —H, unsubstituted or mono- or polysubstituted —$C_{1-12}$-alkyl, or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue;

$R_{17}$ is —H; -halo; unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; unsubstituted or mono- or polysubstituted—heteroaryl, optionally being bridged through a saturated or unsaturated, unsubstituted or mono- or polysubstituted aliphatic $C_{1-12}$-hydrocarbon residue; —$OR_{19}$, —$NH_2$, —$NHR_{19}$, or —$NR_{19}R_{20}$, wherein $R_{19}$ and $R_{20}$ are each independently selected from unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; or unsubstituted or mono- or polysubstituted -heteroaryl, optionally being bridged through a saturated or unsaturated, unsubstituted or mono- or polysubstituted aliphatic $C_{1-12}$-hydrocarbon residue;

(iv) benzoyl-derivatives according to general formula (V)

(V)

wherein $R_{21}$ and $R_{22}$ are each independently selected from unsubstituted or mono- or polysubstituted $C_{6-10}$-aryl and unsubstituted or mono- or polysubstituted heteroaryl;

(v) secodione-derivatives according to general formula (VI)

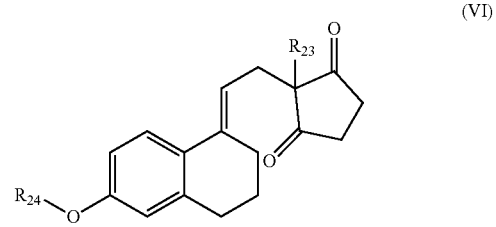

(VI)

wherein $R_{23}$ and $R_{24}$ are each independently selected from the group consisting of —H and —$C_{1-12}$-alkyl; and (vi) 3-quinuclidone;
(vii) ethyl-4-chloro-3-oxo-butanoate; and
(viii) ethyl-3-oxo-3-phenyl-propanoate;
(ix) ketose;

or wherein the aldehyde substrate is selected from the group consisting of (x) 2-butanal; and
(xi) 1-heptanal;

wherein in each case mono- or polysubstituted means independently substituted with one or more functional groups selected from -halo, =O, —OH, —OC$_{1-12}$-alkyl, —OC$_{6-10}$-aryl, —O-heteroaryl, —OCOC$_{1-12}$-alkyl, —OCOC$_{6-10}$-aryl, —OCO-heteroaryl, —SH, —SC$_{1-12}$-alkyl, —SC$_{6-10}$-aryl, —S-heteroaryl, —S(=O)$_{1-20}$H, —NO, —NO$_2$, —N$_3$, —NH$_2$, —NH(C$_{1-12}$-alkyl), —N(C$_{1-12}$-alkyl)$_2$, —NH(C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO— heteroaryl.

16. The method of claim 15, wherein the ketoreductase converts isopropyl alcohol to acetone at a rate of 0.01-100 U/mg lyophilisate of the ketoreductase; and/or
after incubation for 48 h in 50% of aqueous isopropyl alcohol at 30° C. exhibits a residual activity of at least 1%, relative to its activity before incubation.

17. The method according to claim 1, wherein the ketoreductase is capable of stereoselectively reducing the keto reductase substrate of general formula (I)

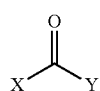

(I)

and the keto substrate is reduced to a secondary alcohol; or wherein the ketoreductase is capable of stereoselectively oxidizing an aldehyde substrate of general formula (I')

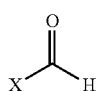

(I')

and the aldehyde substrate is reduced to a primary alcohol;
wherein X and Y are each independently selected from saturated or unsaturated, unsubstituted or mono- or polysubstituted aliphatic or alicyclic C$_{1-12}$-hydrocarbon residues; unsubstituted or mono- or polysubstituted C$_{6-10}$-aromatic hydrocarbon residues, optionally being bridged to the CO-moiety through a saturated or unsaturated, unsubstituted or mono- or polysubstituted aliphatic C$_{1-12}$-hydrocarbon residue; unsubstituted or mono- or polysubstituted heteroaromatic hydrocarbon residues, optionally being bridged to the CO-moiety through a saturated or unsaturated, unsubstituted or mono- or polysubstituted aliphatic C$_{1-12}$-hydrocarbon residue; and sugar residues or desoxysugar residues in each case comprising mono-, di- or oligosaccharides;

wherein mono- or polysubstituted means independently substituted with one or more functional groups selected from
halo, —OH, =O, —OC$_{1-12}$-alkyl, —OC$_{6-10}$-aryl, —O-heteroaryl, —OCOC$_{1-12}$-alkyl, —OCOC$_{6-10}$-aryl, —OCO-heteroaryl, —SH, —SC$_{1-12}$-alkyl, —SC$_{6-10}$-aryl, —S-heteroaryl, —S(=O)$_{1-2}$OH, —NO, —NO$_2$, —N$_3$, —NH$_2$, —NH(C$_{1-12}$-alkyl), —N(C$_{1-12}$-alkyl)$_2$, —NH(C$_{6-10}$-aryl), —N(C$_{6-10}$-aryl)$_2$, —NH(heteroaryl), —N(heteroaryl)$_2$, —CN, —CHO, —CO$_2$H, CO—C$_{1-2}$-alkyl, —CO—C$_{6-10}$-aryl and —CO-heteroaryl.

18. The method according to claim 1, wherein the ketoreductase is capable of stereoselectively reducing the keto reductase substrates selected from the group consisting of
(i) 3-aryl-3-ketopropanamine-derivatives according to general formula (II)

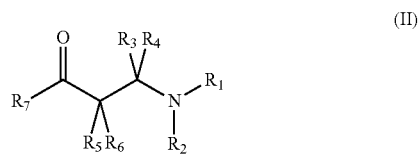

(II)

wherein
R$_1$ and R$_2$ are each independently selected from the group consisting of —H; unsubstituted or mono- or polysubstituted —C$_{1-12}$-alkyl; unsubstituted or mono- or polysubstituted —C$_{3-8}$-cycloalkyl; unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue; or unsubstituted or mono- or polysubstituted heteroaryl, optionally being bridged through a saturated or unsaturated, unsubstituted or mono- or polysubstituted aliphatic C$_{1-12}$-hydrocarbon residue; or alternatively, wherein
R$_1$ and R$_2$ together with the nitrogen atom to which they are attached form an unsubstituted or mono- or polysubstituted C$_{2-8}$-heterocycloalkyl ring or an unsubstituted or mono- or polysubstituted heteroaryl ring;
R$_3$, R$_4$, R$_5$, and R$_6$ are each independently selected from —H; unsubstituted or mono- or polysubstituted —C$_{1-12}$-alkyl; or wherein R$_3$ and R$_4$ together are =O;
R$_7$ is unsubstituted or mono- or polysubstituted —C$_{6-10}$-aryl; or unsubstituted or mono- or polysubstituted -heteroaryl;
(ii) 5-hydroxy-3-oxo-hexanoate-derivatives according to general formula (III)

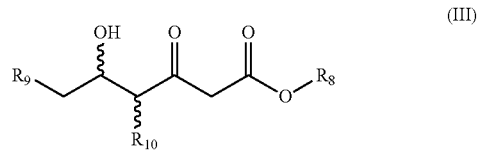

(III)

wherein
R$_8$ is unsubstituted or mono- or polysubstituted —C$_{1-12}$-alkyl; or unsubstituted or mono- or polysubstituted —C$_{6-10}$-aryl, optionally being bridged through a saturated or unsaturated, unsubstituted or mono- or polysubstituted aliphatic C$_{1-12}$-hydrocarbon residue;
R$_9$ is —H; -halo; —CN; or —OR$_{11}$, wherein R$_{11}$ is hydrogen or a protecting group;
R$_{10}$ is —H; unsubstituted or mono- or polysubstituted —C$_{1-12}$-alkyl; or unsubstituted or mono- or polysubstituted —C$_{6-10}$-aryl, optionally being bridged through a saturated or unsaturated, unsubstituted or mono- or polysubstituted aliphatic $C_{1-12}$-hydrocarbon residue;

(iii) acetophenone-derivatives according to general formula (IV)

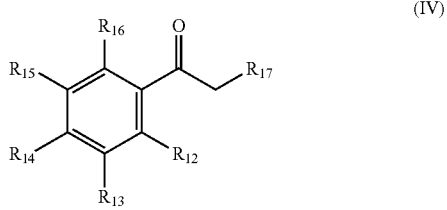

wherein $R_{12}$, $R_{13}$, $R_{14}$, $R_{15}$, and $R_{16}$ are each independently selected from the group consisting of —H; -halo; unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; unsubstituted or mono- or polysubstituted -heteroaryl, optionally being bridged through a saturated or unsaturated, unsubstituted or mono- or polysubstituted aliphatic $C_{1-12}$-hydrocarbon residue; and $OR_{18}$, wherein $R_{18}$ is —H, unsubstituted or mono- or polysubstituted —$C_{1-12}$-alkyl, or unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue;

$R_{17}$ is —H; -halo; unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; unsubstituted or mono- or polysubstituted—heteroaryl, optionally being bridged through a saturated or unsaturated, unsubstituted or mono- or polysubstituted aliphatic $C_{1-12}$-hydrocarbon residue; —$OR_{19}$, —$NH_2$, —$NHR_{19}$, or —$NR_{19}R_{20}$, wherein $R_{19}$ and $R_{20}$ are each independently selected from unsubstituted or mono- or polysubstituted —$C_{1-12}$-alkyl; unsubstituted or mono- or polysubstituted —$C_{6-10}$-aryl, optionally being bridged through a saturated or unsaturated, unsubstituted or mono- or polysubstituted aliphatic $C_{1-12}$-hydrocarbon residue; or unsubstituted or mono- or polysubstituted -heteroaryl, optionally being bridged through a saturated or unsaturated, unsubstituted or mono- or polysubstituted aliphatic $C_{1-12}$-hydrocarbon residue;

(iv) benzoyl-derivatives according to general formula (V)

wherein $R_{21}$ and $R_{22}$ are each independently selected from unsubstituted or mono- or polysubstituted $C_{6-10}$-aryl and unsubstituted or mono- or polysubstituted heteroaryl;

(v) secodione-derivatives according to general formula (VI)

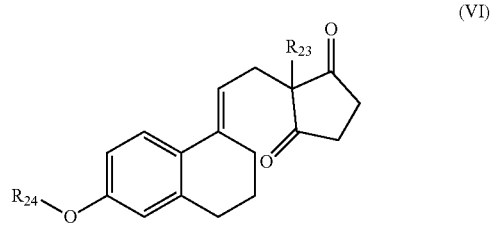

wherein $R_{23}$ and $R_{24}$ are each independently selected from the group consisting of —H and —$C_{1-12}$-alkyl; and (vi) 3-quinuclidone;

(vii) ethyl-4-chloro-3-oxo-butanoate; and (viii) ethyl-3-oxo-3-phenyl-propanoate;

(ix) ketose;

or wherein the aldehyde substrate is selected from the group consisting of (x) 2-butanal; and (xi) 1-heptanal;

wherein in each case mono- or polysubstituted means independently substituted with one or more functional groups selected from -halo, =O, —OH, —$OC_{1-12}$-alkyl, —$OC_{6-10}$-aryl, —O-heteroaryl, —$OCOC_{1-12}$-alkyl, —$OCOC_{6-10}$-aryl, —OCO-heteroaryl, —SH, —$SC_{1-12}$-alkyl, —$SC_{6-10}$-aryl, —S-heteroaryl, —S(=O)$_{1-2}$OH, —NO, —$NO_2$, —$N_3$, —$NH_2$, —NH($C_{1-12}$-alkyl), —N($C_{1-12}$-alkyl)$_2$, —NH($C_{6-10}$-aryl), —N($C_{6-10}$-aryl)$_2$, —NH(heteroaryl), —N(heteroaryl)$_2$, —CN, —CHO, —$CO_2$H, CO—$C_{1-2}$-alkyl, —CO—$C_{6-10}$-aryl and —CO— heteroaryl.

19. The method according to claim 1, wherein the ketoreductase is capable of stereoselectively reducing the keto reductase substrates selected from the group consisting of (i) ethyl-4-chloro-3-oxo-butanoate which is reduced to ethyl (3S)-4-chloro-3-hydroxy-butanoate; or (ii) 3-Quinuclidone (1-azabicyclo[2.2.2]octan-3-one hydrochloride) which is stereoselectively reduced to 3-Quinuclidinol (synonymous to 1-azabicyclo-[2.2.2]octan-3-ol); or (iii) 1-(2-methoxyphenyl)ethanone, which is reduced to 1-(2-ethoxyphenyl)ethanol.

20. The method according to claim 1, wherein the ketoreductase is capable of stereoselectively reducing the keto reductase substrate ethyl-4-chloro-3-oxo-butanoate which is reduced to ethyl (3S)-4-chloro-3-hydroxy-butanoate.

21. The method according to claim 1, wherein the ketoreductase comprises an amino acid sequence with at least 86% sequence identity to SEQ ID NO:2.

22. The method according to claim 1, wherein the ketoreductase comprises an amino acid sequence with at least 88% sequence identity to SEQ ID NO:2.

* * * * *

UNITED STATES PATENT AND TRADEMARK OFFICE
CERTIFICATE OF CORRECTION

PATENT NO. : 10,724,008 B2
APPLICATION NO. : 16/117296
DATED : July 28, 2020
INVENTOR(S) : Ramona Schmiedel et al.

It is certified that error appears in the above-identified patent and that said Letters Patent is hereby corrected as shown below:

In the Specification

In Column 1, Line 11, after "2014" insert -- . --.

In Column 6, Line 27, delete "-OCCOC$_{6-10}$-aryl" and insert -- -OCOC$_{6-10}$-aryl --, therefore.

In the Claims

In Column 179, Line 40, in Claim 10, delete "(1 S)" and insert -- (1S) --, therefore.

In Column 183, Line 15, in Claim 16, delete "claim 15," and insert -- claim 14, --, therefore.

Signed and Sealed this
Twenty-ninth Day of December, 2020

Andrei Iancu
*Director of the United States Patent and Trademark Office*